(12) United States Patent
Pawson et al.

(10) Patent No.: US 6,218,356 B1
(45) Date of Patent: *Apr. 17, 2001

(54) NEURAL RECEPTOR TYROSINE KINASE

(75) Inventors: Anthony Pawson; Mark Henkemeyer, both of Toronto; Kenneth Letwin, Willowdale, all of (CA)

(73) Assignee: Mount Sinai Hospital Corporation, Toronto (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/542,635

(22) Filed: Oct. 13, 1995

Related U.S. Application Data

(63) Continuation-in-part of application No. PCT/CA95/00254, filed on Apr. 28, 1995, which is a continuation-in-part of application No. 08/235,407, filed on Apr. 29, 1994, now abandoned.

(51) Int. Cl.$^7$ ........................ A01N 37/18; C07K 14/705; C12N 15/12

(52) U.S. Cl. ............................ 514/2; 435/69.1; 530/350; 536/23.5

(58) Field of Search ............................... 435/69.1, 252.3, 435/320.1; 530/350; 536/23.5; 514/2

(56) References Cited

FOREIGN PATENT DOCUMENTS

WO 93/00425    7/1993   (WO) .

OTHER PUBLICATIONS

Lai et al, Neuron 6:681–704, May 1991.*
Kramer et al., Nature 352:207–212, 1991.
Pawson and Bernstein, Trends in Genetics 6:350–356, 1990.
Nieto et al., Development 116:1137–1150, 1992.
Elkins et al., Cell 60:565–575, 1990.
Hynes and Lander, Cell 68:303–322, 1992.
Gertler et al., Cell 58:103–113, 1989.
Henkemeyer et al., Cell 63:949–960, 1990.
Martin–Zanca, Dionisio et al., Genes & Dev., 4:683–694, 1990.
Koch et al., Science 252:668, 1991.
Frohman et al., Proc. Nat. Acad. Sci. USA 85:8998–9002, 1988.
Klein, Rudiger et al., Development, 109:845–850, 1990.
Lamballe, Fabienne et al., Cell., 66:967–979, 1991.
Marchionni, M.A., et al., Nature 362:312–318, 1993.
Ben–David, Y. et al., The EMBO Journal, 10:317–325, 1991.
Bothwell, Mark, Cell., 65:915–918, 1991.
Lyman et al., 1993, Cell 75:1157–1167.
Greenwald and Rubin, Cell 68:271–281, 1992.
Sprenger et al., Nature 338:478–483, 1989.
Hirai et al., Science 238:1717–1720, 1987.
Letwin et al., Oncogene 3:621–627, 1988.
Lindberg et al., Mol. Cell. Biol. 10:6316–6324, 1990.
Chan and Watt, Oncogene 6:1057–1061, 1991.
Pasquale, Cell Regulation 2:523–534, 1991.
Sajjadi et al., New Biologist 3:769–778, 1991.
Wicks et al., PNAS 89:1611–1615, 1992.
Gilardi–Hebenstreit et al., Oncogene 7:2499–2506, 1992.
Bohme et al., Oncogene 8:2857–2862, 1993.
Sajjadi and Pasquale, Oncogene 8:1807–1813, 1993.
Dodd J. and Jessell T.M., Science 242:692–699, 1988.
Jessell, T.M., Neuron 1:3–13, 1988.
Furley, A.J. et al., Cell 61:157–170, 1990.
Burns, F.R. et al., Neuron 7:209–220, 1991.
Bastiani et al., Cell 48:745–755, 1987.
Grenningloh et al., Cold Spring Harb. Symp. Quant. Biol. 55, 327–340, 1991.
Nose et al., Cell 70:553–567, 1992.
Edelman and Thiery, In The Cell in Contact: Adhesions and Junctions as Morphogenetic Determinants, Wiley, New York, 1985.
Hatta et al., Dev. Biol. 120:215–227, 1987.
Takeichi, Development 102:639–655, 1988.
Takeichi, Annu. Rev. Biochem. 59:237–252, 1990.
Takeichi, Science 251:1451–1455, 1991.
Edelman, Biochemistry 27:3533–3543, 1988.
Grumet, Curr. Opin. Neurobiol. 1:370–376, 1991.
Detrick et al., Neuron 4:493–506, 1990.
Fujimori et al., Development 110:97–104, 1990.
Goodman and Shatz, Cell 72:77–98, 1993.
Van De Water and Represa, Van De Water, T.R. and Represa, J. (1991). Ann. NY Acad. 630:116–128, 1991.
Guild, Amer. J. Anat. 39:57–81, 1927.
Rugh, The Mouse: Its reproduction and Development. Minneapolis: Burgess, 1968; Sher, 1971, pp. 154–251.
Hendriks, D.M. and Toerien, M.J., S.Afr. Med. J. 47:2294–2298, 1973.
Theiler, K., The House Mouse. Development and Normal Stages from Fertilization to 4 Weeks of Age. Berlin: Springer–Verlag. pp. 44, 45, 48, 53–61, 66, 67, 72–75, 78, 79 and 83.

(List continued on next page.)

Primary Examiner—John Ulm
(74) Attorney, Agent, or Firm—Merchant & Gould P.C.

(57) ABSTRACT

Novel receptor tyrosine kinase protein and isoforms thereof which are expressed in migrating axons, and nucleic acid molecules encoding the novel protein isoforms and parts thereof are disclosed. The invention also relates to methods for identifying substances which are capable of binding to the receptor protein and methods for screening for agonists or antagonists of the binding of the protein and substance. Diagnostic and therapeutic methods using the protein and nucleic acid molecules are also described.

1 Claim, 54 Drawing Sheets

(20 of 54 Drawing Sheet(s) Filed in Color)

OTHER PUBLICATIONS

Kaufman, In Postimplantation Mammalian Embryos: a Practical Approach (ed. A.J. Copp and D.L. Cockroft) pp. 81–91. New York: Oxford University Press, 1990.

Tian et al., Cell 67:675–685, 1991.

Henkemeyer et al., Abstract, Mouse Molecular Genetics Meeting, Aug., 1993, Neural Kinase: A Novel Murine Receptor–like Tyrosine Kinase is localized in Embryos at Sites of Cellular Intereactions During Segmental Patterning of the Neural Tube and in Pioneer Axons.

Henkemeyer et al., J. Cell. Biochem. Suppl. 16F, p. 106, 1992.

Henkemeyer et al., J. Cell. Biochem. Suppl. 16B, p. 195, 1992.

Kazlauskas and Cooper, EMBO J., 9: 3279–3286, 1990.

Henkemeyer et al., Oncogene, 9:1001–1014, 1994.

Henkemeyer and Pawson, Abstract, Keystone Symposium, 1994, The Receptor Tyrosine Kinase NUK in the Developing Brain and Early Axon.

Tessier–Lavigne, Marc, Cell. 82:345–348, 1995.

Fox et al., Oncogene, 10:897–905, 1995.

Ullrich and Schlessinger, Cell, 61:203–212, 1990.

Cheng et al., Cell, 82:371–381, 1995.

Drescher et al., 82;359–370, 1995.

Iwase et al., Biochem. Biophys. Res. Comm. 194:698–705. 1993.

Henkemeyer, M., EMBL Rodents Database, Mus Musculus Nuk Receptor Tyrosine Kinase mRNA, Nov., 1993.

* cited by examiner

FIGURE 1

| Sequence | Position |
|---|---|
| ATGGGAGCCCGGGTCCCCGTTCTGCCCGGGCTGGATGGCTCATTCTGCTGGCTGCTGCTG | 60 |
| CTGCCGCTGCTAGCCGCCGTGGAAGAAACCCTGATGGACTCTACGACAGCAACGGCTGAG | 120 |
| CTGGGCTGGATGGTACATCCCCCATCAGGGTGGGAAGAGGTGAGCGGCTACGACGAGAAC | 180 |
| ATGAACACTATCCGTACCTACCAGGTGTGCAATGTCTTTGAGTCAAGCCAGAACAACTGG | 240 |
| CTGCGGACCAAATTCATCCGGCGCCGTGGCGCCCACCGTATCCACGTGGAGATGAAGTTC | 300 |
| TCGGTGCGTGACTGCAGCAGCATTCCCAGCGTGCCGGGCTCCTGCAAGGAGACCTTCAAC | 360 |
| CTCTACTACTATGAGGCTGATTTTGACTTAGCCACCAAAACCTTTCCCAACTGGATGGAG | 420 |
| AATCCGTGGGTGAAGGTGGACACCATCGCGGCCGATGAGAGCTTCTCTCAGGTGGACCTG | 480 |
| GGTGGCCGCGTCATGAAAATCAACACTGAGGTGCGAAGCTTCGGTCCTGTGTCCCGCAAT | 540 |
| GGTTTCTACCTGGCCTTCCAGGACTACGGCGGCTGTATGTCCCTCATTGCTGTGCGCGTC | 600 |
| TTCTACCGGAAGTGCCCCCGAATCATCCAGAATGGTGCCATCTTCCAGGAGACACTATCG | 660 |
| GGGGCTGAGAGCACTTCGCTGGTGGCAGCTCGGGGCAGCTGCATCGCCAATGCTGAAGAA | 720 |
| GTGGACGTGCCCATCAAACTCTACTGTAACGGGGACGGCGAATGGCTGGTGCCCATCGGT | 780 |
| CGCTGCATGTGCAAGGCGGGCTTCGAGGCTGTGGAGAACGGCACCGTCTGCCGAGGTTGT | 840 |
| CCATCAGGAACCTTCAAGGCCAACCAAGGGGACGAAGCCTGCACCCACTGTCCCATCAAC | 900 |
| AGCCGCACCACCTCTGAGGGTGCCACCAACTGTGTATGCCGCAACGGCTACTACAGGGCC | 960 |
| GACCTGGACCCCTTAGACATGCCTTGCACAACCATCCCCTCTGCGCCCCAGGCTGTGATC | 1020 |
| TCCAGCGTCAACGAGACATCCCTCATGCTAGAGTGGACCCCACCCCGAGACTCCGGGGGT | 1080 |
| CGCGAGGATCTTGTTTACAACATCATCTGCAAGAGCTGTGGCTCCGGCCGGGGCGCATGC | 1140 |
| ACGCGCTGCGGGGACAACGTGCAGTACGCGCCCCGCCAGCTGGGCCTGACTGAGCCGCGC | 1200 |
| ATCTACATCAGTGACCTGCTGGCACACACGCAGTACACCTTCGAGATCCAGGCCGTGAAT | 1260 |
| GGTGTGACCGACCAGAGTCCCTTCTCACCTCAGTTCGCCTCTGTGAACATCACCACCAAC | 1320 |
| CAAGCAGCACCATCGGCCGTGTCCATCATGCACCAGGTGAGCCGCACTGTGGACAGCATC | 1380 |
| ACCCTGTCGTGGTCCCAGCCAGACCAGCCCAACGGTGTGATCCTGGACTACGAGCTGCAG | 1440 |
| TACTATGAGAAGGAGCTCAGTGAGTACAACGCCACGGCCATAAAAAGCCCCACCAACACA | 1500 |
| GTCACTGTGCAGGGCCTCAAAGCCGGCGCCATCTATGTCTTCCAGGTGCGGGCACGCACC | 1560 |

FIGURE 1 (CONT'D)

```
GTTGCAGGCTATGGGCGCTACAGTGGCAAGATGTACTTCCAAACCATGACAGAAGCCGAG     1620
TACCAGACCAGCATCAAGGAAAAGCTACCCCTCATCGTTGGCTCCTCCGCCGCCGGCTTA     1680
GTCTTCCTCATCGCTGTGGTCGTCATTGCCATCGTATGTAACAGACGGGGGTTTGAGCGT     1740
GCCGACTCAGAGTACACGGACAAGCTACAGCACTACACCAGCGGACACATGACCCCAGGC     1800
ATGAAGATCTATATAGATCCTTTCACCTATGAAGATCCTAATGAGGCAGTGCGGGAGTTT     1860
GCCAAGGAAATTGACATCTCCTGTGTCAAGATTGAGCAGGTGATTGGAGCAGGGGAATTT     1920
GGTGAGGTCTGCAGTGGCCATTTGAAGCTGCCAGGCAAGAGAGAGATCTTTGTAGCCATC     1980
AAGACCCTCAAGTCAGGATACACGGAGAAACAGCGCCGGGACTTCCTGAGTGAGGCATCC     2040
ATCATGGGCCAGTTCGACCACCCCAATGTCATCCATCTGGAAGGGGTTGTCACCAAGAGC     2100
ACACCTGTCATGATCATCACTGAATTCATGGAGAATGGATCTCTGGACTCCTTCCTCCGG     2160
CAAAATGATGGGCAGTTCACAGTCATCCAACTGGTGGGCATGCTGAGGGGCATTGCAGCC     2220
GGCATGAAGTACCTGGCGGACATGAACTACGTGCACCGTGACCTTGCTGCTCGAAACATC     2280
CTCGTCAACAGTAACCTGGTGTGTAAGGTGTCTGACTTTGGGCTCTCACGCTTCCTGGAG     2340
GATGACACGTCTGAGCCCACCTATACCAGCGCTCTGGGTGGGAAGATCCCCATCCGTTGG     2400
ACGGCACCGGAAGCCATCCAGTACCGGAAATTCACCTCGGCCAGTGATGTGTGGAGCTAT     2460
GGCATCGTCATGTGGGAGGTGATGTCCTACGGGGAACGACCCTACTGGGACATGACCAAT     2520
CAAGACGTAATCAACGCCATTGAACAGGACTACAGACTACCTCCGCCCATGGACTGCCCT     2580
AGCGCCCTGCACCAGCTCATGCTGGACTGCTGGCAGAAGGACCGCAACCACCGGCCCAAG     2640
TTCGGCCAGATTGTCAACACGCTGGACAAGATGATCCGAAACCCCAACAGCCTCAAAGCC     2700
ATGGCACCCCTGTCCTCTGGCATCAACCTGCCACTGCTGGACCGCACGATACCGGACTAC     2760
ACCAGCTTTAACACAGTGGATGAGTGGCTAGAGGCCATCAAGATGGGCCAGTACAAGGAG     2820
AGCTTTGCCAACGCCGGCTTCACCTCTTTCGACGTTGTATCTCAGATGATGATGGAGGAC     2880
ATTCTCCGCGTTGGGGTCACTCTAGCTGGCCACCAGAAAAAAATCCTGAACAGTATCCAG     2940
GTGATGCGGGCCCAGATGAACCAGATCCAGTCTGTAGAGGTTTGACATTCGCCTGCCTCG     3000
GTTCTCCTCTTCCTCCACGCCGCCCCTGAGCCCCTACGTCGGTCCCTGCTGCTCTGTCAC     3060
TGCAGGTCAGCACTGCCAGGAGGCCACAGACAACAGGAAGACCAA                   3105
```

FIGURE 2

```
MGARVPVLPGLDGSFCWLLLLPLLAAVEETLMDSTTATAELGWMVHPPSG
WEEVSGYDENMNTIRTYQVCNVFESSQNNWLRTKFIRRRGAHRIHVEMKF  100
SVRDCSSIPSVPGSCKETENLYYYEADFDLATKTFPNWMENPWVKVDTIA
ADESFSQVDLGGRVMKINTEVRSFGPVSRNGFYLAFQDYGGCMSLIAVRV  200
FYRKCPRIQNGAIFQETLSGAESTSLVAARGSCIANAEEVDVPIKLYCN
GDGEWLVPIGRCMCKAGFEAVENGTVCRGCPSGTFKANQGDEACTHCPIN  300
SRTTSEGATNCVCRNGYYRADLDPLDMPCTTIPSAPQAVISSVNETSLML
EWTPPRDSGGREDLVYNIICKSCGSGRGACTRCGDNVQYAPRQLGLTEPR  400
IYISDLLAHTQYTFEIQAVNGVTDQSPFSPQFASVNITTNQAAPSAVSIM
HQVSRTVDSITLSWSQPDQPNGVILDYELQYYEKELSEYNATAIKSPTNT  500
VTVQGLKAGAIYVFQVRARTVAGYGRYSGKMYFQTMTEAEYQTSIKEKLP
LIVGSSAAGLVFLIAVVVIAIVCNRRGFERADSEYTDKLQHYTSGHMTPG  600
MKIYIDPFTYEDPNEAVREFAKEIDISCVKIEQVIGAGEFGEVCSGHLKL
PGKREIFVAIKTLKSGYTEKQRRDFLSEASIMGQFDHPNVIHLEGVVTKS  700
TPVMIITEFMENGSLDSFLRQNDGQFTVIQLVGMLRGIAAGMKYLADMNY
VHRDLAARNILVNSNLVCKVSDFGLSRFLEDDTSDPTYTSALGGKIPIRW  800
TAPEAIQYRKFTSASDVWSYGIVMWEVMSYGERPYWDMTNQDVINAIEQD
YRLPPPMDCPSALHQLMLDCWQKDRNHRPKFGQIVNTLDKMIRNPNSLKA  900
MAPLSSGINLPLLDRTIPDYTSFNTVDEWLEAIKMGQYKESFANAGFTSF
DVVSQMMMEDILRVGVTLAGHQKKILNSIQVMRAQMNQIQSVEV        994
```

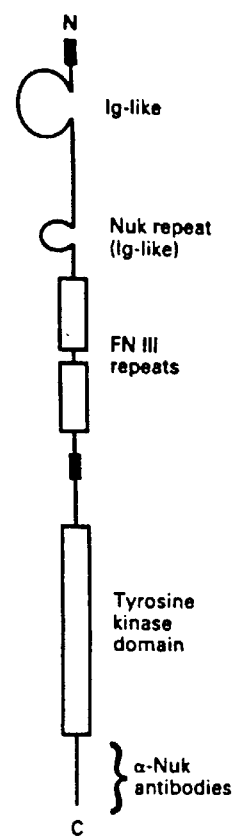

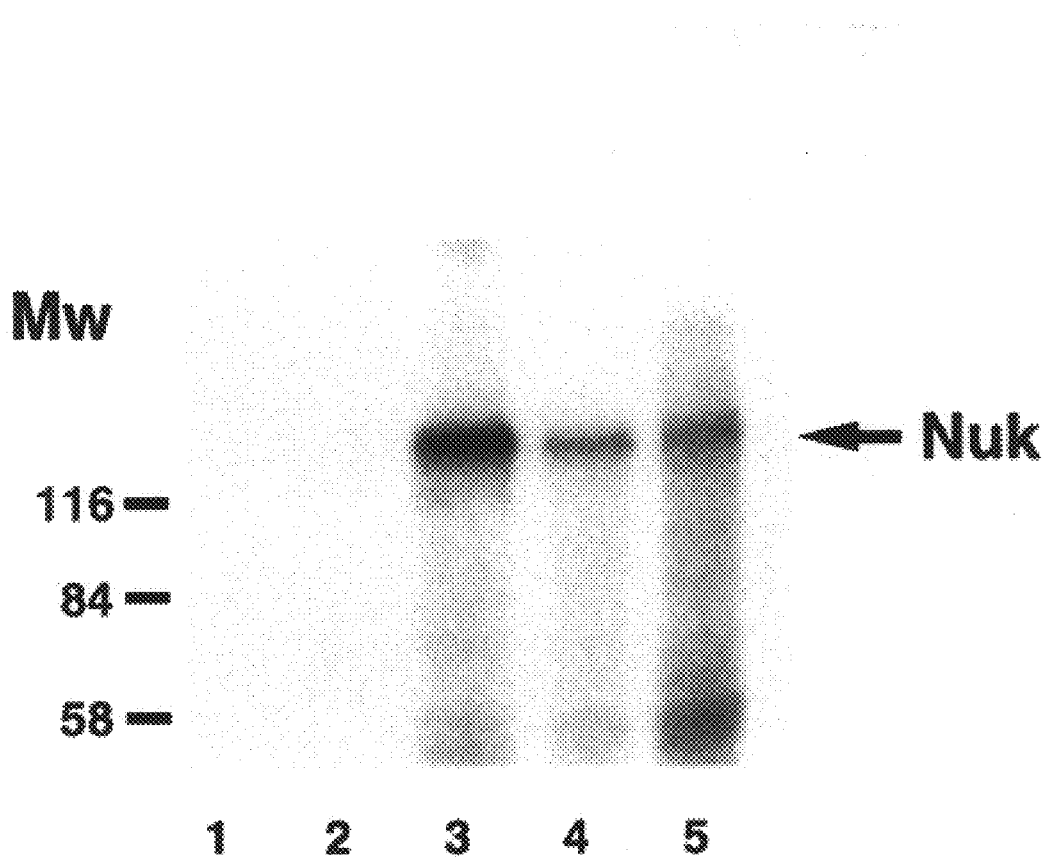

Nuk gene targeting: deletion of exon 2 (codons 29 to 50).

FIGURE 9B
Nuk protein is not detected in *Nuk¹/Nuk¹* embryos
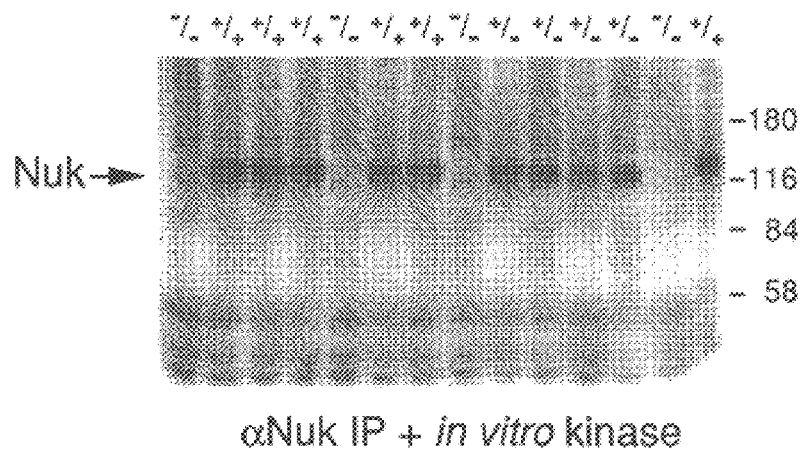
αNuk IP + *in vitro* kinase
Nuk protein is not detected in *Nuk¹/Nuk¹* embryos
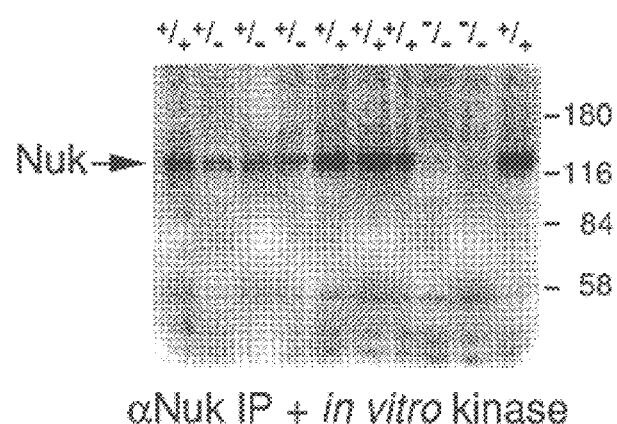
αNuk IP + *in vitro* kinase pPNT-LOX-Nuk 2 gene trap knockout vector deletes the GXGXXG ATP binding region of the kinase domain (a.a. 623-707) and creates a Nuk-lac z fusion receptor Frequency of homologous recombination: 3/118

Peptide competition

Blot: αGST (αp85)

Fast Blue dye tracing of the temporal lobe

In normal mice and Nuk2/Nuk2 homozygotes the dye traces to the contralateral temporal lobe and to the thalamus.
In Nuk1/Nuk1 homozygotes, the dye fails to trace into the contralateral lobe. The dye does trace, however, to the thalamus indicating that this axon pathway is not affected.

Axon pathways affected in Nuk;Sek4 double homozygotes

A.C. Anterior commisure
H.I.P. Habenular-interpeduncle tract

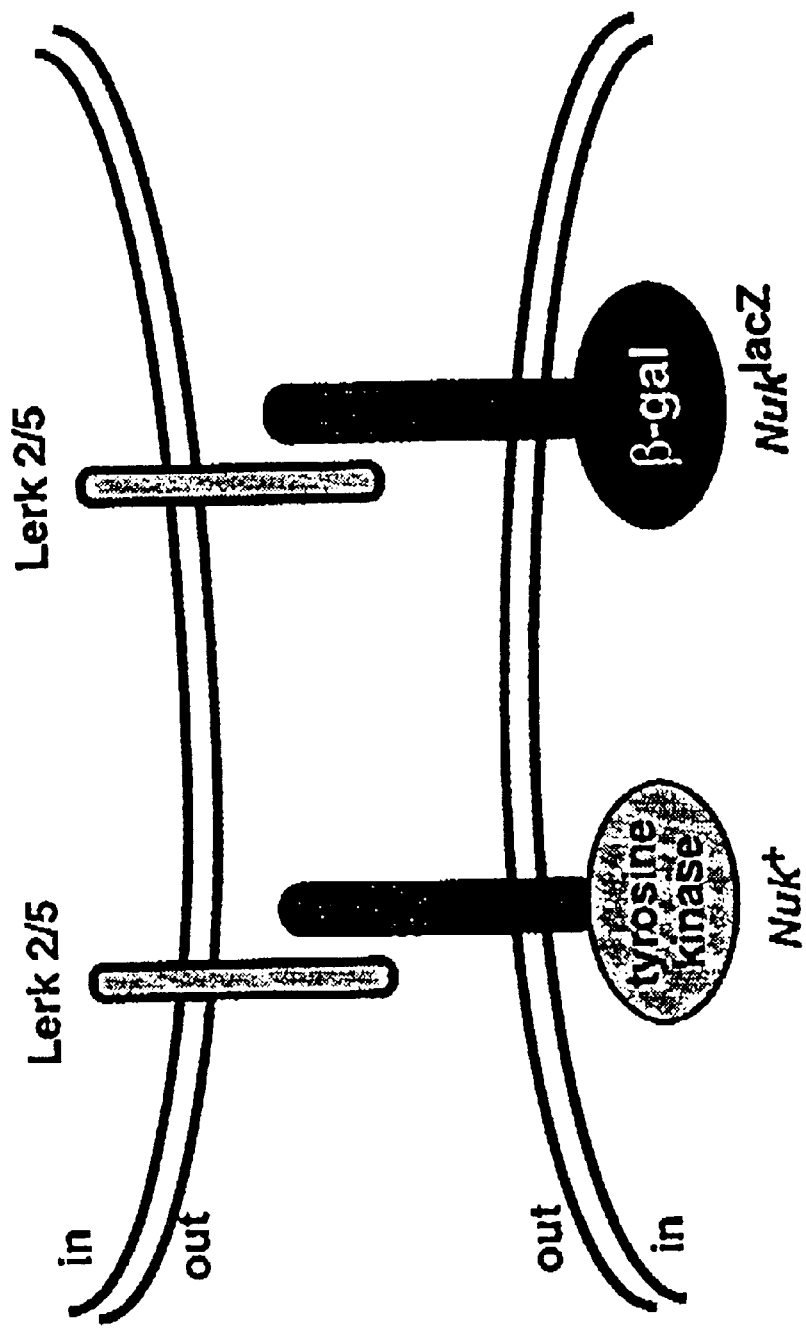

```
                              SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
          (A) LENGTH: 3105 base pairs
          (B) TYPE: nucleic acid
          (C) STRANDEDNESS: single
          (D) TOPOLOGY: linear (ii) MOLECULE TYPE: cDNA (vi) ORIGINAL SOURCE:
          (A) ORGANISM: Mus musculus
          (D) DEVELOPMENTAL STAGE: Embryo (vii) IMMEDIATE SOURCE:
          (A) LIBRARY: lambda gt10 cDNA library
          (B) CLONE: Combined PnUKRACE A2 and K2 AND cDNA clones (viii) POSITION IN GENOME:
          (A) CHROMOSOME/SEGMENT: Distal end of chromosome 4
          (B) MAP POSITION: near the ahd-1 mutation (xi) SEQUENCE DESCRIPTION: SEQ ID NO:1:

ATGGGAGCCC GGGTCCCCGT TCTGCCCGGG CTGGATGGCT CATTCTGCTG GCTGCTGCTG         60
```

```
CTGCCGCTGC TAGCCGCCGT GGAAGAAACC CTGATGGACT CTACGACAGC AACGGCTGAG    120

CTGGGCTGGA TGGTACATCC CCCATCAGGG TGGGAAGAGG TGAGCGGCTA CGACGAGAAC    180

ATGAACACTA TCCGTACCTA CCAGGTGTGC AATGTCTTTG AGTCAAGCCA GAACAACTGG    240

CTGCGGACCA AATTCATCCG GCGCCGTGGC GCCCACCGTA TCCACGTGGA GATGAAGTTC    300

TCGGTGCGTG ACTGCAGCAG CATTCCCAGC GTGCCGGGCT CCTGCAAGGA GACCTTCAAC    360

CTCTACTACT ATGAGGCTGA TTTTGACTTA GCCACCAAAA CCTTTCCCAA CTGGATGGAG    420

AATCCGTGGG TGAAGGTGGA CACCATCGCG GCCGATGAGA GCTTCTCTCA GGTGGACCTG    480

GGTGGCCGCG TCATGAAAAT CAACACTGAG GTGCGAAGCT TCGGTCCTGT GTCCCGCAAT    540

GGTTTCTACC TGGCCTTCCA GGACTACGGC GGCTGTATGT CCCTCATTGC TGTGCGCGTC    600

TTCTACCGGA AGTGCCCCCG AATCATCCAG AATGGTGCCA TCTTCCAGGA GACACTATCG    660

GGGGCTGAGA GCACTTCGCT GGTGGCAGCT CGGGGCAGCT GCATCGCCAA TGCTGAAGAA    720

GTGGACGTGC CCATCAAACT CTACTGTAAC GGGGACGGCG AATGGCTGGT GCCCATCGGT    780

CGCTGCATGT GCAAGGCGGG CTTCGAGGCT GTGGAGAACG GCACCGTCTG CCGAGGTTGT    840

CCATCAGGAA CCTTCAAGGC CAACCAAGGG GACGAAGCCT GCACCCACTG TCCCATCAAC    900

AGCCGCACCA CCTCTGAGGG TGCCACCAAC TGTGTATGCC GCAACGGCTA CTACAGGGCC    960

GACCTGGACC CCTTAGACAT GCCTTGCACA ACCATCCCCT CTGCGCCCCA GGCTGTGATC    1020

TCCAGCGTCA ACGAGACATC CCTCATGCTA GAGTGGACCC CACCCCGAGA CTCCGGGGGT    1080

CGCGAGGATC TTGTTTACAA CATCATCTGC AAGAGCTGTG GCTCCGGCCG GGGCGCATGC    1140

ACGCGCTGCG GGGACAACGT GCAGTACGCG CCCCGCCAGC TGGGCCTGAC TGAGCCGCGC    1200

ATCTACATCA GTGACCTGCT GGCACACACG CAGTACACCT TCGAGATCCA GGCCGTGAAT    1260

GGTGTGACCG ACCAGAGTCC CTTCTCACCT CAGTTCGCCT CTGTGAACAT CACCACCAAC    1320

CAAGCAGCAC CATCGGCCGT GTCCATCATG CACCAGGTGA GCCGCACTGT GGACAGCATC    1380

ACCCTGTCGT GGTCCCAGCC AGACCAGCCC AACGGTGTGA TCCTGGACTA CGAGCTGCAG    1440

TACTATGAGA AGGAGCTCAG TGAGTACAAC GCCACGGCCA TAAAAAGCCC CACCAACACA    1500

GTCACTGTGC AGGGCCTCAA AGCCGGCGCC ATCTATGTCT TCCAGGTGCG GGCACGCACC    1560

GTTGCAGGCT ATGGGCGCTA CAGTGGCAAG ATGTACTTCC AAACCATGAC AGAAGCCGAG    1620

TACCAGACCA GCATCAAGGA AAAGCTACCC CTCATCGTTG GCTCCTCCGC CGCCGGCTTA    1680

GTCTTCCTCA TCGCTGTGGT CGTCATTGCC ATCGTATGTA ACAGACGGGG GTTTGAGCGT    1740

GCCGACTCAG AGTACACGGA CAAGCTACAG CACTACACCA GCGGACACAT GACCCCAGGC    1800

ATGAAGATCT ATATAGATCC TTTCACCTAT GAAGATCCTA ATGAGGCAGT GCGGGAGTTT    1860

GCCAAGGAAA TTGACATCTC CTGTGTCAAG ATTGAGCAGG TGATTGGAGC AGGGGAATTT    1920

GGTGAGGTCT GCAGTGGCCA TTTGAAGCTG CCAGGCAAGA GAGAGATCTT TGTAGCCATC    1980

AAGACCCTCA AGTCAGGATA CACGGAGAAA CAGCGCCGGG ACTTCCTGAG TGAGGCATCC    2040

ATCATGGGCC AGTTCGACCA CCCCAATGTC ATCCATCTGG AAGGGGTTGT CACCAAGAGC    2100

ACACCTGTCA TGATCATCAC TGAATTCATG GAGAATGGAT CTCTGGACTC CTTCCTCCGG    2160

CAAAATGATG GCAGTTCAC AGTCATCCAA CTGGTGGGCA TGCTGAGGGG CATTGCAGCC    2220

GGCATGAAGT ACCTGGCGGA CATGAACTAC GTGCACCGTG ACCTTGCTGC TCGAAACATC    2280

CTCGTCAACA GTAACCTGGT GTGTAAGGTG TCTGACTTTG GCCTCTCACG CTTCCTGGAG    2340

GATGACACGT CTGACCCCAC CTATACCAGC GCTCGGGTG GGAAGATCCC CATCCGTTGG    2400

ACGGCACCGG AAGCCATCCA GTACCGGAAA TTCACCTCGG CCAGTGATGT GTGGAGCTAT    2460
```

-continued

```
GGCATCGTCA TGTGGGAGGT GATGTCCTAC GGGGAACGAC CCTACTGGGA CATGACCAAT    2520

CAAGACGTAA TCAACGCCAT TGAACAGGAC TACAGACTAC CTCCGCCCAT GGACTGCCCT    2580

AGCGCCCTGC ACCAGCTCAT GCTGGACTGC TGGCAGAAGG ACCGCAACCA CCGGCCCAAG    2640

TTCGGCCAGA TTGTCAACAC GCTGGACAAG ATGATCCGAA ACCCCAACAG CCTCAAAGCC    2700

ATGGCACCCC TGTCCTCTGG CATCAACCTG CCACTGCTGG ACCGCACGAT ACCGGACTAC    2760

ACCAGCTTTA ACACAGTGGA TGAGTGGCTA GAGGCCATCA AGATGGGCCA GTACAAGGAG    2820

AGCTTTGCCA ACGCCGGCTT CACCTCTTTC GACGTTGTAT CTCAGATGAT GATGGAGGAC    2880

ATTCTCCGCG TTGGGGTCAC TCTAGCTGGC CACCAGAAAA AAATCCTGAA CAGTATCCAG    2940

GTGATGCGGG CCCAGATGAA CCAGATCCAG TCTGTAGAGG TTTGACATTC GCCTGCCTCG    3000

GTTCTCCTCT TCCTCCACGC CGCCCCTGAG CCCCTACGTC GGTCCCTGCT GCTCTGTCAC    3060

TGCAGGTCAG CACTGCCAGG AGGCCACAGA CAACAGGAAG ACCAA                   3105
```

(2) INFORMATION FOR SEQ ID NO:2:

(i) SEQUENCE CHARACTERISTICS:
        (A) LENGTH: 994 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Mus musculus
        (D) DEVELOPMENTAL STAGE: Embryo (vii) IMMEDIATE SOURCE:
        (A) LIBRARY: lamda gt10 cDNA library
        (B) CLONE: Combined pNukRACE A2 and K2 and cDNA clones (viii) POSITION IN GENOME:
        (A) CHROMOSOME/SEGMENT: Distal end of chromosome 4
        (B) MAP POSITION: near the ahd-1 mutation (xi) SEQUENCE DESCRIPTION: SEQ ID NO:2:

```
Met Gly Ala Arg Val Pro Val Leu Pro Gly Leu Asp Gly Ser Phe Cys
1               5                   10                  15

Trp Leu Leu Leu Pro Leu Leu Ala Ala Val Glu Glu Thr Leu Met
            20                  25                  30

Asp Ser Thr Thr Ala Thr Ala Glu Leu Gly Trp Met Val His Pro Pro
            35                  40                  45

Ser Gly Trp Glu Glu Val Ser Gly Tyr Asp Glu Asn Met Asn Thr Ile
    50                  55                  60

Arg Thr Tyr Gln Val Cys Asn Val Phe Glu Ser Ser Gln Asn Asn Trp
65                  70                  75                  80

Leu Arg Thr Lys Phe Ile Arg Arg Gly Ala His Arg Ile His Val
                85                  90                  95

Glu Met Lys Phe Ser Val Arg Asp Cys Ser Ser Ile Pro Ser Val Pro
            100                 105                 110

Gly Ser Cys Lys Glu Thr Phe Asn Leu Tyr Tyr Glu Ala Asp Phe
            115                 120                 125

Asp Leu Ala Thr Lys Thr Phe Pro Asn Trp Met Glu Asn Pro Trp Val
130                 135                 140

Lys Val Asp Thr Ile Ala Ala Asp Glu Ser Phe Ser Gln Val Asp Leu
145                 150                 155                 160

Gly Gly Arg Val Met Lys Ile Asn Thr Glu Val Arg Ser Phe Gly Pro
                165                 170                 175
```

```
                            -continued

Val Ser Arg Asn Gly Phe Tyr Leu Ala Phe Gln Asp Tyr Gly Gly Cys
            180                 185                 190

Met Ser Leu Ile Ala Val Arg Val Phe Tyr Arg Lys Cys Pro Arg Ile
            195                 200                 205

Ile Gln Asn Gly Ala Ile Phe Gln Glu Thr Leu Ser Gly Ala Glu Ser
            210                 215                 220

Thr Ser Leu Val Ala Ala Arg Gly Ser Cys Ile Ala Asn Ala Glu Glu
225                 230                 235                 240

Val Asp Val Pro Ile Lys Leu Tyr Cys Asn Gly Asp Gly Glu Trp Leu
                245                 250                 255

Val Pro Ile Gly Arg Cys Met Cys Lys Ala Gly Phe Glu Ala Val Glu
                260                 265                 270

Asn Gly Thr Val Cys Arg Gly Cys Pro Ser Gly Thr Phe Lys Ala Asn
            275                 280                 285

Gln Gly Asp Glu Ala Cys Thr His Cys Pro Ile Asn Ser Arg Thr Thr
            290                 295                 300

Ser Glu Gly Ala Thr Asn Cys Val Cys Arg Asn Gly Tyr Tyr Arg Ala
305                 310                 315                 320

Asp Leu Asp Pro Leu Asp Met Pro Cys Thr Thr Ile Pro Ser Ala Pro
                325                 330                 335

Gln Ala Val Ile Ser Ser Val Asn Glu Thr Ser Leu Met Leu Glu Trp
                340                 345                 350

Thr Pro Pro Arg Asp Ser Gly Gly Arg Glu Asp Leu Val Tyr Asn Ile
                355                 360                 365

Ile Cys Lys Ser Cys Gly Ser Gly Arg Gly Ala Cys Thr Arg Cys Gly
            370                 375                 380

Asp Asn Val Gln Tyr Ala Pro Arg Gln Leu Gly Leu Thr Glu Pro Arg
385                 390                 395                 400

Ile Tyr Ile Ser Asp Leu Leu Ala His Thr Gln Tyr Thr Phe Glu Ile
                405                 410                 415

Gln Ala Val Asn Gly Val Thr Asp Gln Ser Pro Phe Ser Pro Gln Phe
            420                 425                 430

Ala Ser Val Asn Ile Thr Thr Asn Gln Ala Ala Pro Ser Ala Val Ser
            435                 440                 445

Ile Met His Gln Val Ser Arg Thr Val Asp Ser Ile Thr Leu Ser Trp
450                 455                 460

Ser Gln Pro Asp Gln Pro Asn Gly Val Ile Leu Asp Tyr Glu Leu Gln
465                 470                 475                 480

Tyr Tyr Glu Lys Glu Leu Ser Glu Tyr Asn Ala Thr Ala Ile Lys Ser
                485                 490                 495

Pro Thr Asn Thr Val Thr Val Gln Gly Leu Lys Ala Gly Ala Ile Tyr
            500                 505                 510

Val Phe Gln Val Arg Ala Arg Thr Val Ala Gly Tyr Gly Arg Tyr Ser
            515                 520                 525

Gly Lys Met Tyr Phe Gln Thr Met Thr Glu Ala Glu Tyr Gln Thr Ser
            530                 535                 540

Ile Lys Glu Lys Leu Pro Leu Ile Val Gly Ser Ala Ala Gly Leu
545                 550                 555                 560

Val Phe Leu Ile Ala Val Val Ile Ala Ile Val Cys Asn Arg Arg
                565                 570                 575

Gly Phe Glu Arg Ala Asp Ser Glu Tyr Thr Asp Lys Leu Gln His Tyr
                580                 585                 590
```

-continued

```
Thr Ser Gly His Met Thr Pro Gly Met Lys Ile Tyr Ile Asp Pro Phe
        595                 600                 605
Thr Tyr Glu Asp Pro Asn Glu Ala Val Arg Glu Phe Ala Lys Glu Ile
        610                 615                 620
Asp Ile Ser Cys Val Lys Ile Glu Gln Val Ile Gly Ala Gly Glu Phe
625                 630                 635                 640
Gly Glu Val Cys Ser Gly His Leu Lys Leu Pro Gly Lys Arg Glu Ile
                645                 650                 655
Phe Val Ala Ile Lys Thr Leu Lys Ser Gly Tyr Thr Glu Lys Gln Arg
                660                 665                 670
Arg Asp Phe Leu Ser Glu Ala Ser Ile Met Gly Gln Phe Asp His Pro
            675                 680                 685
Asn Val Ile His Leu Glu Gly Val Val Thr Lys Ser Thr Pro Val Met
        690                 695                 700
Ile Ile Thr Glu Phe Met Glu Asn Gly Ser Leu Asp Ser Phe Leu Arg
705                 710                 715                 720
Gln Asn Asp Gly Gln Phe Thr Val Ile Gln Leu Val Gly Met Leu Arg
                725                 730                 735
Gly Ile Ala Ala Gly Met Lys Tyr Leu Ala Asp Met Asn Tyr Val His
                740                 745                 750
Arg Asp Leu Ala Ala Arg Asn Ile Leu Val Asn Ser Asn Leu Val Cys
            755                 760                 765
Lys Val Ser Asp Phe Gly Leu Ser Arg Phe Leu Glu Asp Asp Thr Ser
770                 775                 780
Asp Pro Thr Tyr Thr Ser Ala Leu Gly Gly Lys Ile Pro Ile Arg Trp
785                 790                 795                 800
Thr Ala Pro Glu Ala Ile Gln Tyr Arg Lys Phe Thr Ser Ala Ser Asp
                805                 810                 815
Val Trp Ser Tyr Gly Ile Val Met Trp Glu Val Met Ser Tyr Gly Glu
                820                 825                 830
Arg Pro Tyr Trp Asp Met Thr Asn Gln Asp Val Ile Asn Ala Ile Glu
            835                 840                 845
Gln Asp Tyr Arg Leu Pro Pro Met Asp Cys Pro Ser Ala Leu His
850                 855                 860
Gln Leu Met Leu Asp Cys Trp Gln Lys Asp Arg Asn His Arg Pro Lys
865                 870                 875                 880
Phe Gly Gln Ile Val Asn Thr Leu Asp Lys Met Ile Arg Asn Pro Asn
                885                 890                 895
Ser Leu Lys Ala Met Ala Pro Leu Ser Ser Gly Ile Asn Leu Pro Leu
                900                 905                 910
Leu Asp Arg Thr Ile Pro Asp Tyr Thr Ser Phe Asn Thr Val Asp Glu
            915                 920                 925
Trp Leu Glu Ala Ile Lys Met Gly Gln Tyr Lys Glu Ser Phe Ala Asn
        930                 935                 940
Ala Gly Phe Thr Ser Phe Asp Val Val Ser Gln Met Met Glu Asp
945                 950                 955                 960
Ile Leu Arg Val Gly Val Thr Leu Ala Gly His Gln Lys Lys Ile Leu
                965                 970                 975
Asn Ser Ile Gln Val Met Arg Ala Gln Met Asn Gln Ile Gln Ser Val
                980                 985                 990
Glu Val
```

NEURAL RECEPTOR TYROSINE KINASE

FIELD OF THE INVENTION

This is a continuation-in-part of International Application PCT/CA95/00254, with an international filing date of Apr. 28, 1995, which in turn is a continuation-in-part of U.S. Ser. No. 08/235,407, filed Apr. 29, 1994, now abandoned, which applications are incorporated herein by reference. The invention relates to a novel receptor tyrosine kinase protein and isoforms and parts thereof, nucleic acid molecules encoding the novel protein and fragments thereof, and uses of the protein and nucleic acid molecules.

BACKGROUND OF THE INVENTION

Embryonic development of multicellular organisms is a highly ordered process that requires coordination of individual cells. Every cell must decipher the numerous signals it receives and then properly execute commands in order to achieve the correct position and differentiated state in the animal. The exquisite controls over cell growth, determination, migration and adhesion are mediated by molecules located on the plasma membrane surface.

A class of membrane associated molecules known to regulate cellular interactions are receptor tyrosine kinase proteins. The evolutionary conservation of genes encoding receptor tyrosine kinase proteins and their targets has emphasized the importance of these proteins in intracellular communication, and has also provided model systems for genetic analysis of tyrosine kinase signalling pathways. Such studies have shown that some tyrosine kinases function to specify a particular cell fate, such as the sevenless (sev) receptor in Drosophila R7 photoreceptor cells and the Let-23 receptor in nematode vulval cells (reviewed by Greenwald and Rubin, *Cell* 68:271–281, 1992). The binding of sev with its ligand, boss, results in cell clustering suggesting a role in cell—cell adhesion for these molecules (Kramer et al., *Nature* 352:207–212, 1991). The receptor tyrosine kinase encoded by torso functions in pattern formation by specifying the terminal poles of Drosophila embryos (Sprenger et al., *Nature* 338:478–483, 1989). Genetic analysis has recently provided insight into the functions of a small number of receptor tyrosine kinases in mouse development, including the α-platelet-derived growth factor receptor, the colony stimulating factor-1 receptor, and c-Kit/W (Pawson and Bernstein, *Trends in Genetics* 6:350–356, 1990).

A growing number of closely related transmembrane receptor tyrosine kinase proteins containing cell adhesion-like domains on their extracelluar surface have recently been identified. Collectively, this group of proteins defines the Eph/Elk/Eck subfamily, which is made up of at least fifteen related but unique gene sequences in higher vertebrates (Hirai et al., *Science* 238:1717–1720, 1987; Letwin et al., *Oncogene* 3:621–627, 1988; Lindberg et al., *Mol. Cell. Biol.* 10:6316–6324, 1990; Lhotak et al., *Mol. Cell. Biol.* 11:2496–2502, 1991; Chan and Watt, *Oncogene* 6:1057–1061, 1991; Lai and Lemke, *Neuron* 6:691–704, 1991; Pasquale, *Cell Regulation* 2:523–534, 1991; Sajjadi et al., *New Biologist* 3:769–778, 1991; Wicks et al., *PNAS* 89:1611–1615, 1992; Gilardi-Hebenstreit et al., *Oncogene* 7:2499–2506, 1992; Bohme et al., *Oncogene* 8:2857–2862, 1993; Sajjadi and Pasquale, *Oncogene* 8:1807–1813, 1993). Eph family members encode a structurally related cysteine rich extracelluar domain containing a single immunoglobulin (Ig)-like loop near the N-terminus and two fibronectin III (FN III) repeats adjacent to the plasma membrane. Examples of Eph family members include Cek5 (Pasquale, *Cell Regulation* 2:523–534, 1991) and Erk; (Chan and Watt, *Oncogene* 6:1057–1061 1991). Another Eph family member, Sek, has been shown to be segmentally expressed in specific rhombomeres of the mouse hindbrain (Nieto et al., *Development* 116:1137–1150, 1992). The presence of cell adhesion-like domains in this family of tyrosine kinases suggests that these proteins function in cell-cell interactions.

The other major families of proteins implicated in cell adhesion include the cadherins, selecting, integrins, and those of the immunoglobulin superfamily (reviewed by Hynes, R. O. and Landers, A. D., Cell 68, 303–322, 1992). The extracelluar regions of cell adhesion molecules frequently contain peptide repeats, such as FN III motifs, epidermal growth factor (EGF) repeats, or Ig loops that may direct protein-protein interactions at the cell surface. A number of cell adhesion molecules in both vertebrates (Dodd, J. and Jessell, T. M., Science, 242, 692–699, 1988; Jessell, T. M., Neuron, 1, 3–13, 1988; Furley et al., Cell 61, 157–170, 1990; Burns et al., Neuron, 7, 209–220, 1991) and invertebrates (Bastiani et al., *Cell* 48:745–755, 1987; Elkins et al., *Cell* 60:565–575, 1990; Grenningloh et al., *Cold Spring Harb, Symp. Quant. Biol.* 55, 327–340, 1991; Nose et al., *Cell* 70:553–567, 1992) have been implicated in axonal growth cone guidance and pathway/target recognition. Other aspects of neuronal morphogenesis involving cell-cell interactions may also require the activities of cell adhesion molecules (Edelman and Thiery, In *The Cell in Contact: Adhesions and Junctions as Morphogenetic Determinants*, Wiley, New York, 1985; Hatta et al., *Dev. Biol.* 120:215–227, 1987; Takeichi, *Development* 102:639–655, 1988; Takeichi, *Annu. Rev. Biochem.* 59:237–252 1990; Takeichi, *Science* 251:1451–1455, 1991; Edelman, *Biochemistry* 27:3533–3543, 1988; Grumet, *Curr. Opin. Neurobiol.* 1:370–376, 1991; Hynes and Lander, *Cell* 68:303–322, 1992). For example, ectopic N-cadherin expression during gastrulation stage Xenopus embryos has been shown to interfere with segregation of the neural tube from the ectoderm (Detrick et al., *Neuron* 4:493–506, 1990; Fujimori et al., *Development* 110:97–104, 1990). Although many different types of cell adhesion molecules have been identified, little is known about how these adhesive interactions are regulated and how they function in cell signalling pathways during normal development.

A critical stage in the development of the nervous system is the projection of axons to their targets. Navigational decisions are made at the growth cones of the migrating axons. As axons grow their growth cones extend and retract filopodia and lamellipodia processes which are implicated in the navigational decisions and pathfinding abilities of migrating axons. Like peripheral nervous system axons, the growth cones of neurons associated with the central nervous system follow stereotyped pathways and apparently can selectively chose from a number of possible routes (reviewed by Goodman and Shatz, *Cell* 72:77–98, 1993). Early pathways in the vertebrate embryonic brain are thought to be arranged as a set of longitudinal tracts connected by commissures. However, the molecular mechanisms that underly growth cone navigation and axon pathfinding in development are poorly understood (Hynes, R. O. and Lander, A. D., 1992, Cell 68:303).

Evidence indicates that the development of the endolymphatic duct is under the control of neuronal induction (Van De Water and Represa, Van De Water, T. R. and Represa, J. (1991). *Ann. NY Acad.* 630:116–128, 1991). The endolymphatic duct pinches off from the otic vesicle and elongates to form a tube that apparently functions in regulating the endolymph fluid pressure in the membranous labyrinth of the internal ear (Guild, *Amer. J. Anat.* 39:57–81, 1927; Rugh, *The Mouse: Its reproduction and Development*. Minneapolis: Burgess, 1968; Sher, 1971; Hendriks and Toerien, 1973; Theiler, 1989; Kaufman, In *Postimplantation Mammalian Embryos: a Practical Approach* (ed. A. J. Copp and D. L. Cockroft) pp. 81–91. New York: Oxford University Press, 1990).

The developmental function of tyrosine kinases during axonogenesis has been studied in Drosophila. A function in axonal pathfinding is evident for the Drosophila abl tyrosine kinase when abl mutations are combined with mutations in other genes including the neural cell adhesion molecule, fasciclin I (fas I, Elkins et al., *Cell* 60:565–575, 1990) or disabled (dab, Gertler et al., *Cell* 58:103–113, 1989). These studies have shown that the abl tyrosine kinase is specifically localized to the axonal compartment of the embryonic Central Nervous System (CNS) (Gertler et al., *Cell* 58:103–113, 1989). Moreover, genetic analysis has indicated that subcellular localization to axons is essential for abl function during development (Henkemeyer et al., *Cell* 63:949–960, 1990) and that mutations in second-site modifier genes including fas I and dab can reveal a role for abl in axonogenesis (Elkins et al., *Cell* 60:565–575, 1990; Gertler et al., *Cell* 58:103–113 1989). The requirement for tyrosine phosphorylation in axonal outgrowth and adhesion in Drosophila is strengthened by the identification in CNS axons of three transmembrane tyrosine phosphatases containing FN III motifs (Tian et al., *Cell* 67:675–685, 1991; Yang et al., *Cell* 67:661–673, 1991).

SUMMARY OF THE INVENTION

The present inventors have identified and characterized a receptor tyrosine kinase protein that plays an important role in cell—cell interactions and axonogenesis in the development of the nervous system. In particular, the present inventors have cloned a novel murine gene, designated neural kinase (Nuk). The gene encodes a new member of the Eph subfamily of receptor tyrosine kinases, designated Nuk protein. The murine Nuk locus was mapped to the distal end of mouse chromosome 4 near the ahd-1 mutation.

The biological function of Nuk protein was investigated using antibodies having anti-Nuk protein specificity. A detailed immunohistochemical analysis of its subcellular localization in whole-mount mouse embryos indicated that during early embryogenesis Nuk protein is confined to the developing nervous system, where it marks segments along the axis of the neural tube in the hindbrain (rhombomeres r2, r3, and r5) and specific morphological bulges of the midbrain and forebrain.

Nuk protein was also found to be concentrated at sites of cell—cell contact, often involving migrating neuronal cells or their extensions. Most notably, high levels of Nuk protein were found within initial axon outgrowths and associated nerve fibers, including most if not all peripheral nervous system (PNS) axons. The axonal localization of Nuk protein was also found to be transient and was not detected after migrations have ceased.

In newborn and adult mice, Nuk protein was found to be expressed at high levels in the axons of sensory and motor ganglia, including the retinal cells of the eyes, the olfactory receptor neurons, and the trigeminal ganglia, including sensory fibers from the whiskers.

The subcellular localization of Nuk protein, as well as the presence of fibronectin type III and immunoglobulin-like adhesive domains on the extracelluar region, indicates that this receptor tyrosine kinase functions to regulate specific cell—cell interactions during early development of the nervous system and that it has a role during the early pathfinding and/or fasciculation stages of axonogenesis in animals.

Importantly, the present inventors have shown that the expression of Nuk protein is essential for axonogenesis of at least one major central nervous system axon tract. In Nuk null mutant mice, which do not express Nuk protein, it was found that the pars posterior medial tract of the anterior commissure failed to develop. Surprisingly, in Nuk-lac Z fusion chimeric receptor mutant mice, expressing Nuk protein lacking in a catalytic kinase domain, the anterior commissure was present, demonstrating a vital role for the Nuk protein which is independent from the kinase domain and which may be mediated by the extracellular domain. A novel role for the extracellular domain of Nuk protein is disclosed.

The present invention therefore provides a purified and isolated nucleic acid molecule containing a sequence encoding a receptor tyrosine kinase protein which is expressed in migrating axons, or an oligonucleotide fragment of the sequence which is unique to the receptor tyrosine kinase protein. In a preferred embodiment of the invention, the purified and isolated nucleic acid molecule comprises (a) a nucleic acid sequence encoding a protein having the amino acid sequence as shown in SEQ ID NO:2 and FIG. 2; (b) nucleic acid sequences complementary to (a); (c) nucleic acid sequences which are at least 97% identical to (a); or, (d) a fragment of (a) or (b) that is at least 15 bases and which will hybridize to (a) or (b) under stringent hybridization conditions.

Most preferably, the purified and isolated nucleic acid molecule comprises (a) a nucleic acid sequence as shown in SEQ ID NO:1 and FIG. 1A and FIG. 1B, wherein T can also be U; (b) nucleic acid sequences complementary to (a); (c) nucleic acid sequences which are at least 85% identical to (a); or, (d) a fragment of (a) or (b) that is at least 15 bases and which will hybridize to (a) or (b) under stringent hybridization conditions.

The present invention also contemplates an isolated and purified nucleic acid molecule comprising a nucleic acid sequence encoding the amino acid sequence as shown in SEQ ID NO:2 or an amino acid sequence having at least 98%, preferably 99%, most preferably 99.5% homology thereto, or an isoform or a part of the protein having at least 20 contiguous amino acids. In an embodiment, the nucleic acid molecule may comprise a nucleic acid sequence encoding a protein having substantially the amino acid sequence as shown in SEQ ID NO:2. In a further embodiment, the nucleic acid molecule may encode an extracellular domain of a tyrosine kinase having about at least the amino acid sequence as shown in SEQ ID NO: 2 from amino acid number 26 to 548, preferably from 26 to 544. In a still further embodiment, the nucleic acid molecule may comprise a nucleic acid sequence encoding a phosphorylation site which, when phosphorylated, may associate with SH2 domains, preferably at least the amino acid sequence as shown in SEQ ID NO:2 from amino acid number 604 to 613, having the sequence YIDPFTYEDP.

It is contemplated that a nucleic acid molecule of the invention may be prepared having deletion and insertion mutations. For example, the extracelluar domain or parts thereof, such as the FN III and Ig domains; the transmembrane region or parts thereof; the tyrosine kinase domain or parts thereof, such as the ATP binding site and; the carboxy terminal tail may be deleted. In a preferred embodiment, the deletions are in a portion of the nucleic acid molecule of the invention encoding the extracelluar domain of Nuk protein, most preferably the portion comprising codons 29 to 50 in SEQ ID NO:1. In another preferred embodiment, the deletions are in a portion of the nucleic acid sequence of the invention encoding the kinase domain of Nuk protein, most preferably the portion comprising the ATP-binding site amino acid number 623–707.

The invention further contemplates a purified and isolated double stranded nucleic acid molecule containing a nucleic acid molecule of the invention or a fragment thereof, hydrogen bonded to a complementary nucleic acid base sequence.

The nucleic acid molecules of the invention, or fragments thereof may be inserted into an appropriate expression vector, i.e. a vector which contains the necessary elements for the transcription and translation of the inserted protein-coding sequence. Accordingly, recombinant DNA molecules adapted for transformation of a host cell may be constructed which comprise a nucleic acid molecule of the invention and one or more transcription and translation elements operatively linked to the nucleic acid molecule.

In an embodiment of the invention, a recombinant molecule is provided which contains a nucleic acid molecule of the invention having a deletion or insertion mutation. Such a recombinant molecule may further comprise a reporter gene.

The recombinant molecule can be used to prepare transformed host cells expressing the protein or part thereof encoded by a nucleic acid molecule of the invention. Therefore, the invention further provides host cells containing a recombinant molecule of the invention. The invention also contemplates transgenic non-human mammals whose germ cells and somatic cells contain a recombinant molecule of the invention.

The invention further provides a method for preparing a novel receptor tyrosine kinase protein or isoforms or parts thereof utilizing the purified and isolated nucleic acid molecules of the invention.

The invention further broadly contemplates a purified and isolated receptor tyrosine kinase protein which is expressed in migrating axons, or an isoform or a part of the protein. In a preferred embodiment, a purified receptor tyrosine kinase protein is provided which has substantially the amino acid sequence as shown in SEQ ID NO:2 or FIG. 2, or a sequence having between 97 and 100, preferably at least 99, most preferably at least 99.5 percent identity thereto. The receptor tyrosine kinase protein of the invention may also be phosphorylated.

Conjugates of Nuk protein of the invention, or parts thereof, with other molecules, such as proteins or polypeptides, may be prepared. This may be accomplished, for example, by the synthesis of N-terminal or C-terminal fusion proteins. In a preferred embodiment a fusion protein is provided comprising a part of the protein of the invention, preferably the extracellular domain, morepreferably having the amino acid sequence as shown in SEQ ID NO: 2 from amino acid number 26 to 548, most preferably from amino acid number 26 to 544, or amino acids 600 to 618, preferably amino acids 604 to 613; or the carboxy terminal, most preferably having the amino acid sequence as shown in SEQ ID NO:2 from amino acid number 601 to 994; or the catalytic domain, most preferably having the amino acid sequence as shown in SEQ ID NO:2 from amino acid number 623 to 888; or sequences having at least 97%, preferably at least 99%, most preferably at least 99.5% identity thereto; or portions of the catalytic domain, preferably phosphorylation sites.

The invention also permits the construction of nucleotide probes which are unique to the nucleic acid molecules of the invention and accordingly to the novel receptor tyrosine kinase protein of the invention or a part of the protein. Thus, the invention also relates to a probe comprising a nucleotide sequence coding for a protein which displays the properties of the novel receptor tyrosine kinase of the invention or a part which is unique to the protein. The probe may be labelled, for example, with a detectable substance and it may be used to select from a mixture of nucleotide sequences a nucleotide sequence coding for a protein which displays the properties of the novel receptor tyrosine kinase protein of the invention, or a part thereof.

The invention still further provides a method for identifying a substance which is capable of binding to the novel receptor tyrosine kinase protein of the invention, or an isoform or part of the protein, comprising reacting the novel receptor tyrosine kinase protein of the invention, or part of the protein, with at least one substance which potentially can bind with the receptor tyrosine kinase protein, isoform or part of the protein, under conditions which permit the formation of substance-receptor kinase protein complexes, and assaying for substance-receptor kinase protein complexes, for free substance, for non-complexed receptor kinase proteins, or for activation of the receptor tyrosine kinase protein or the substance.

In an embodiment of the method, ligands are identified which are capable of binding to and activating the novel receptor tyrosine kinase protein of the invention. The extracellular ligands which bind to and activate the novel receptor tyrosine kinase protein of the invention may be identified by assaying for protein tyrosine kinase activity.

In a further embodiment, substances are identified which are capable of binding to and themselves being activated by the novel receptor tyrosine kinase protein of the invention. Such substances may be identified by biochemical assays for activation of the substance, for example by phosphorylation of the substance or through genetic analysis of the effect of mutant Nuk proteins on the development of specific organs or brain structures such as the anterior commissure. In an embodiment of the method, the substance is provided attached to or inserted through the plasma membrane at the surface of a cell and the substance is identified by assaying for a biological affect on the cell, such as inhibition or stimulation of proliferation, differentiation, migration or pathfinding.

Still further, the invention provides a method for assaying a medium for the presence of an agonist or antagonist of the interaction of a receptor tyrosine kinase protein of the invention and a substance which binds to the receptor tyrosine kinase protein, preferably a ligand. In an embodiment, the method comprises providing a known concentration of a receptor tyrosine kinase protein of the invention, isoforms thereof, or part of the protein, preferably the extracelluar domain of the protein, incubating the receptor tyrosine kinase protein with a substance which is capable of binding to the receptor tyrosine kinase protein, isoforms thereof, or part of the protein, and a suspected agonist or antagonist substance under conditions which permit the formation of substance-receptor protein complexes, and assaying for substance-receptor protein complexes, for free substance, for non-complexed proteins, or for activation of the receptor tyrosine kinase protein or of the substance. The methods of the invention permit the identification of potential stimulators or inhibitors of axonal migration and nerve cell interactions in development and regeneration, which will be useful in the treatment of nerve disorders and nerve damage.

The invention also contemplates a method for identifying a substance which is capable of binding to an activated receptor tyrosine kinase protein of the invention, or an isoform or part of the activated protein, comprising reacting the activated receptor tyrosine kinase protein of the invention, or part of the protein, with at least one substance which potentially can bind with the receptor tyrosine kinase protein, isoform or part of the protein, under conditions which permit the formation of substance-receptor kinase protein complexes, and assaying for substance-receptor kinase protein complexes, for free substance, for non-complexed receptor kinase proteins, for phosphorylation or activation of the substance or for a biological affect in cells having the substance-receptor kinase complexes on their surfaces. In an embodiment of the method, intracellular ligands such as Src homology region 2 (SH2)-containing proteins which are capable of binding to a phosphorylated receptor tyrosine kinase protein of the invention, or intracellular ligands which may be phosphorylated directly or indirectly by the novel receptor tyrosine kinase of the invention may be identified.

The invention further contemplates antibodies having specificity against an epitope of the receptor tyrosine kinase protein of the invention or part of the protein which is unique to the receptor tyrosine kinase protein. Antibodies may be labelled with a detectable substance and they may be used to detect the novel receptor tyrosine kinase of the invention in tissues and cells. The antibodies may accordingly be used to monitor axonal migration and nerve cell interactions.

Substances which affect axonal migration may be identified using the methods of the invention by comparing the pattern and level of expression of the novel receptor tyrosine kinase protein of the invention in tissues and cells in the presence and in the absence of the substance. Thus the invention provides a method for screening for substances having pharmaceutical utility in the treatment and diagnosis of nerve disorders and nerve damage.

The invention still further contemplates a pharmaceutical composition which comprises a purified and isolated receptor tyrosine kinase protein having an amino acid sequence as shown in SEQ ID NO:2 or a sequence having at least 99% homology thereto, or an isoform or a part of the protein having at least 20 contiguous amino acids of the protein effective for affecting neuronal development, in particular for stimulating or inhibiting axonogenesis and a pharmaceutically acceptable carrier, diluent or excipient. In an embodiment, the part of the protein comprises about at least the amino acid sequence as shown in SEQ ID NO: 2 from amino acid number 26 to 548, preferably from 26 to 544. In another embodiment, the part of the protein may contain at least one of the extracellular, transmembrane and juxtamembrane domains, preferably, at least the extracellular domain, of Nuk protein.

A method for affecting neuronal development, in particular for stimulating or inhibiting axonogenesis in a mammal is provided which comprises administering to a mammal in need of such stimulation or inhibition an effective amount of a purified and isolated receptor tyrosine kinase protein having an amino acid sequence as shown in SEQ ID NO:2 or a sequence having at least 99% homology thereto, or an isoform or a part of the protein having at least 20 contiguous amino acids of the protein effective for stimulating or inhibiting axonogenesis. In an embodiment, the part of the protein comprises about at least the amino acid sequence as shown in SEQ ID NO: 2 from amino acid number 26 to 548, preferably from 26 to 544.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The applications contains at least one drawing executed in color.

The invention will be better understood with reference to the drawings in which:

FIG. 1A shows nucleotides 1 to 1680 of the nucleotide sequence encoding the novel receptor tyrosine kinase protein of the invention as shown in SEQ ID NO: 1;

FIG. 1B shows nuclcotides 1681 to 3105 of the nucloctide sequence encoding the novel receptor tyrosine kinase protein of the invention as shown in SEQ ID NO:1;

FIG. 2 shows the amino acid sequence of the novel receptor tyrosine kinase protein of the invention as shown in SEQ ID NO:2 and a schematic diagram of the regions of the novel receptor tyrosine kinase protein of the invention;

FIG. 3A shows immunoprecipitation of the novel receptor tyrosine kinase protein of the invention;

FIG. 9B shows the results of an in vitro kinase assay demonstrating that Nuk protein is not produced in $Nuk^1/Nuk^1$ embryos;

FIG. 27 is a diagram showing a potential signalling role for lerks.

DETAILED DESCRIPTION OF THE INVENTION

Figure 3B:
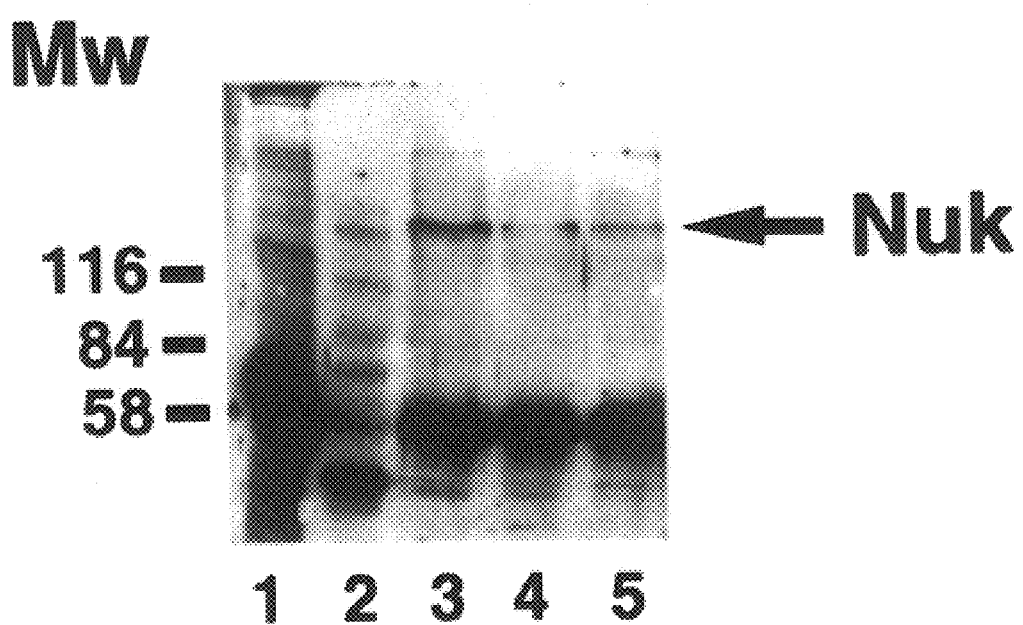
FIG. 3B shows Western Blot analysis of immunoprecipitates of the novel receptor tyrosine kinase protein of the invention.

I. Characterization of Nucleic Acid Molecules and Proteins of the Invention

As hereinbefore mentioned, the present inventors have identified and sequenced a nucleic acid molecule encoding a novel receptor tyrosine kinase protein with a unique expression pattern as described herein. The receptor tyrosine kinase protein of the invention is also referred to herein as Neural Kinase (Nuk) protein.

The Nuk coding region was cloned using a λgt10 expression library constructed from mouse embryo mRNA. The library was probed with a partial λQ1 Nuk cDNA insert. Additional 5'Nuk coding sequences were obtained by rapid amplification of cDNA ends (RACE). Translation of combined RACE and cDNA clones revealed a single open reading frame of 994 codons.

The Nuk locus mapped to the distal end of mouse chromosome 4 near the ahd-1 mutation. The Nuk protein belongs to the Eph/Elk/Eck family, of which many members are expressed in the developing nervous system. The protein encoded by the deduced amino acid sequence of Nuk has all the hallmarks of an Eph family member, including a number of conserved residues of the Eph family, for example the 20 cysteine residues whose position is conserved in the extracelluar domain of Eph family members (bold type, FIG. 2), an immunoglobulin-like domain near the amino terminus (Ig-like), and two fibronectin type III repeats (FN III); between Nuk residues 330–420 and 444–534. The Ig-like domain of Nuk protein contains specific residues (Cys$^{70}$, Trp$^{80}$, Cys$^{115}$) known to be conserved in the Ig superfamily (Williams and Barclay, *Ann. Rev. Immunol.* 6:381–405, 1988). When compared to other known members of the Eph family, Nuk protein was found to be most highly related to the full length amino acid sequence of chicken Cek5 (96% identity).

In accordance with an embodiment of the invention a purified and isolated nucleic acid molecule is provided containing a sequence encoding a protein having the amino acid sequence as shown in SEQ ID NO:2 and FIG. 2. Most preferably, the purified and isolated nucleic acid molecule of the invention contains a nucleic acid sequence as shown in SEQ ID NO:1 and FIG. 1A and FIG. 1B.

Fragments of the nucleic acid molecules are contemplated by the present invention. In a preferred embodiment, the fragments include fragments of the nucleotide sequence as shown in SEQ. ID. NO. 1 and in FIG. 1A and FIG. 1B that have at least 15 bases to 18 bases, preferably at least 15 bases, and which are capable of hybridizing to the nucleotide sequence as shown in SEQ ID NO. 1 and FIG. 1A and FIG. 1B under stringent hybridization conditions as described herein. These fragments may encode, for example, the extracellular domain (amino acids 26 to 548, SEQ ID NO:2) or the carboxy tail (amino acids 601 to 994, SEQ ID NO:2).

It will also be appreciated that a double stranded nucleotide sequence comprising a nucleic acid molecule of the invention or a fragment thereof, hydrogen bonded to a complementary nucleotide base sequence, and an RNA made by transcription of this double stranded nucleotide sequence are contemplated by the present invention.

Further, it will be appreciated that the invention includes nucleic acid or amino acid sequences which have substantial sequence identity with the nucleic acid and amino acid sequences shown in SEQ ID NOS:1 and 2 and in FIG. 1A and FIGS. 1B and 2, and fragments thereof. The term "sequences having substantial sequence identity" means those nucleic acid and amino acid sequences which have slight or inconsequential sequence variations from the sequences disclosed in FIGS. 1A and FIGS. 1B and 2 and SEQ ID NOS: 1 and 2, i.e. the homologous sequences function in substantially the same manner to produce substantially the same polypeptides as the actual sequences. The variations may be attributable to local mutations or structural modifications.

Nucleic acid sequences having substantial identity include nucleic acid sequences which encode proteins having at least 97%, preferably 99%, most preferably 99.5% sequence identity with the amino acid sequences as shown in SEQ. ID. NO:2 and in FIG. 2; nucleic acid sequences having at least 85%, preferably at least 90%, most preferably at least 95% identity with the nucleic acid sequence as shown in SEQ. ID. NO.:1 and in FIG. 1A and FIG. 1B; and fragments thereof having at least 15 to 18, preferably at least 15 bases which will hybridize to these sequences under stringent hybridization conditions. Stringent hybridization conditions are those which are stringent enough to provide specificity, reduce the number of mismatches and yet are sufficiently flexible to allow formation of stable hybrids at an acceptable rate. Such conditions are known to those skilled in the art and are described, for example, in Sambrook, et al, (1989, Molecular Cloning, A Laboratory Manual, Cold Spring Harbor). By way of example only, stringent hybridization with short nucleotides may be carried out at 5–10° below the $T_m$ using high concentrations of probe such as 0.01–1.0 pmole/ml.

The invention further provides amino acid sequences which have substantial identity with the amino acid sequence shown in SEQ ID NO:2 and in FIG. 2. Substantially identical sequences include sequences having at least 97%, preferably at least 99%, most preferably at least 99.5% sequence identity. The invention still further provides peptides which are unique to the receptor tyrosine kinase protein of the invention. Preferably, the peptides have at least 10 to 20 amino acids, preferably at least 20 contiguous amino acids.

The sequence of the nucleic acid molecule of the invention or a fragment thereof, may be inverted relative to its normal presentation for transcription to produce antisense nucleic acid molecules. The antisense nucleic acid molecules may be constructed using chemical synthesis and enzymatic ligation reactions using procedures known in the art. The antisense nucleic acid molecules may be used in gene therapy to treat inherited disorders of the nervous system.

A number of unique restriction sequences for restriction enzymes are incorporated in the nucleic acid sequence identified in SEQ ID NO: 1 and in FIG. 1A and FIG. 1B and these provide access to nucleic acid sequences which code for polypeptides unique to the receptor tyrosine kinase protein of the invention. Nucleic acid sequences unique to the receptor tyrosine kinase protein of the invention or isoforms or parts thereof, can also be constructed by chemical synthesis and enzymatic ligation reactions carried out by procedures known in the art.

The invention contemplates isoforms of the receptor tyrosine kinase protein of the invention. An isoform contains the same number and kinds of amino acids as the protein of the invention, but the isoform has a different molecular structure. The isoforms contemplated by the present invention are those having the same functional properties as the novel receptor tyrosine kinase protein of the invention as described herein.

The present invention also includes conjugates of the receptor tyrosine kinase protein of the invention, or parts thereof. For example, the receptor tyrosine kinase protein or portions thereof may be conjugated with a selected protein or marker protein to produce fusion proteins.

The present invention also includes a receptor tyrosine kinase protein of the invention or part thereof, preferably the catalytic domain, which is enzymatically active. The catalytically active form of the protein or part thereof is also referred to herein as an "activated receptor tyrosine kinase protein or part thereof".

II. Expression Pattern of the Receptor Tyrosine Kinase Protein of the Invention

The expression of Nuk protein has been localized during early embryogenesis. The restricted expression of Nuk imposes constraints on the cellular range of activity of putative Nuk ligands, and indicates that the Nuk locus plays unique and important roles in the determination, migration and pathfinding of axons, in axogenesis and fasciculation, in neural tube formation, and in the regulation of specific cell—cell interactions during early development of the nervous system. As many features of regeneration in the peripheral nervous system recapitulate development, for example, following injury and wallerian degeneration, axons regrow and migrate to reinervate their targets, the Nuk locus also plays an important role in axonal migration during regeneration following injury to the peripheral nervous system.

The present inventors have shown that, in the early stages of embryonic development, Nuk protein is confined to the developing nervous system, where it marks segments along the axis of the neural tube in the hindbrain and specific morphological bulges of the midbrain and forebrain. Nuk is expressed in a rhombomere-specific pattern early during hindbrain segmentation. The restriction of Nuk protein to specific anterior-posterior and dorsal-ventral compartments during early development of the rostral neural tube indicates this receptor tyrosine kinase protein functions in the patterning of specific brain structures.

Nuk protein was found to be expressed in the developing nervous system and, in particular, is highly expressed very early in the retinal ganglion cells and in the group of cells that form the optic chiasm just prior to axonogenesis of the retinal cells. These observations indicate that Nuk protein participates in early development of the visual system components and in pathfinding of retinal axons.

The present inventors have also detected Nuk in cells of the ventral midbrain and in the endolymphatic duct of the developing ear. Peripheral axons were found to express high levels of Nuk, in particular the sensory and motor ganglia throughout the animal, such as the retinal ganglia cells, the olfactory receptor neurons and the trigeminal ganglia, including axons associated with the sensory cells of the whiskers. The expression pattern of Nuk indicates that Nuk protein may play an important role in most or all of the sensory nervous systems, including those of vision, auditory, olfactory and touch.

The present inventors have also localized Nuk protein to specific locations within the cells of the developing nervous system and have shown that Nuk protein is associated with the plasma membrane of migrating neural cells. In particular, Nuk protein is concentrated at sites of cell—cell contact, of migrating neuronal cells or their extensions and high levels of Nuk protein are found within initial axon outgrowths and associated nerve fibers. The axonal localization of Nuk may be transient and often is not detected after the growth cones have reached their targets and migrations have ceased, indicating a role for this receptor tyrosine kinase protein during the early migration, pathfinding and fasciculation stages of axonogenesis.

The role of Nuk protein in neuronal development and axonogenesis was confirmed by the affects of Nuk expression on the formation of central nervous system pathways. In the anterior commissure, the pars posterior medial tract was found not to form in homozygous $Nuk^{1/}/Nuk^{1}$ null mice. However, this tract was present in $Nuk^{2}/Nuk^{2}$ homozygous mice expressing the Nuk fusion protein extracellular domain lacking in an active catalytic kinase domain. Importantly, this demonstrates a vital role for Nuk protein in axonogenesis which is independent of the active catalytic kinase domain and which is likely mediated by the extracellular domain of Nuk protein. The transmembrane and juxtamembrane domains may also be involved. The extracellular domain of Nuk protein, may specifically bind to and activate substances, for example substances on the surface of adjacent cells and the receptor-substance complex may activate the substance thereby providing a signal to produce a biological affect in the adjacent cell. The extracellular domain of Nuk may act as a ligand for the substance and activate the substance to provide an intracellular signal to those adjacent cells.

Nuk protein may function to transmit signals from the plasma membrane and may cooperate with other neuronal tyrosine kinases, preferably with other Eph subfamily receptor tyrosine kinases such as Sek4. The present inventors found that Nuk protein is localized to at least one CNS axon pathway. Nuk expression was detected in the habenular interpeduncle, which connects the thalamus and the ventral midbrain and in the corpus callosum which connects the hemispheres of the cerebral cortex. During development, Nuk expression originates in the region of the ventral midbrain and progresses towards the thalamus. Axon migration occurs along this path from the thalamus towards the ventral midbrain. The formation of the habenular interpeduncle tract was found to depend on Nuk expression. The cooperation of Nuk protein with Sek4 protein was confirmed by observations of mice bearing double Nuk and Sek4 mutations. The majority of mice bearing double $Nuk^{1}/Sek4$ null mutations died at birth. However, a number of $Nuk^{2}/$ Sek4 mutants which express the extracellular domain of Nuk protein and β galactosidase as a fusion protein survived for about three months, indicating that the $Nuk^{2}$ encoded mutant protein retains some of the functional capabilities.

The subcellular localization of Nuk protein is similar to that observed for vimentin and the extracelluar matrix molecule laminin (Liesi, *EMBO* 4:1163–1170, 1985) and it coincides with pathways of neuronal cell migration along the radial glial fibers (Hatten, *Trends Neurosci*. 13:179–184, 1990).

The specific subcellular localization of Nuk protein to the cell—cell contacts between the basement membrane of the endolymphatic duct cells and the surrounding mesenchyme/neural crest cells indicates Nuk protein functions to modulate this interaction.

The concentration of Nuk protein at sites of cell—cell contact indicates that its ligand is a membrane-associated molecule. In addition, Nuk protein immunoreactivity was frequently observed on the membranes of both cells at the site of contact and was generally observed to localize to specific regions of the membrane (see FIGS. 5 and 8). Therefore, homophilic/heterophilic interactions between Eph receptors and their ligands may play a role in their biological functions.

III. Preparation of Nucleic Acid Molecules and Proteins of the Invention

The nucleic acid molecules of the invention encoding the novel receptor tyrosine kinase protein, or fragments thereof, may be isolated and sequenced, for example, by synthesizing cDNAs from mouse embryo RNA and using rapid amplification of cDNA ends (RACE, Frohman, et al., Proc. Na+, Acad. Sci. USA, 85, 8998–9002, 1988) using oligonucleotides specific for the novel receptor tyrosine kinase protein, and analysing the sequences of the clones obtained following amplification. Oligonucleotides specific for the novel receptor tyrosine kinase protein may be identified by comparing the nucleic acid sequence of the nucleic acid molecules of the invention to known sequences, for example, sequences of the other members of the Eph subfamily. Nucleic acid molecules of the present invention encoding the novel receptor tyrosine kinase protein and oligonucleotide fragments thereof, may also be constructed by chemical synthesis and enzymatic ligation reactions using procedures known in the art.

The novel tyrosine kinase receptor protein of the invention may be prepared using recombinant DNA methods. Accordingly, the nucleic acid molecules of the present invention having a sequence which codes for the receptor tyrosine kinase protein of the invention, or a fragment thereof may be incorporated in a known manner into an appropriate expression vector which ensures good expression of the protein or part thereof. Possible expression vectors include but are not limited to cosmids, plasmids, or modified viruses, so long as the vector is compatible with the host cell used.

The invention therefore contemplates a recombinant molecule of the invention containing a nucleic acid molecule of the invention, or a fragment thereof, and the necessary elements for the transcription and translation of the inserted protein-sequence. Suitable transcription and translation elements may be derived from a variety of sources, including bacterial, fungal, viral, mammalian, or insect genes. Selection of appropriate transcription and translation elements is dependent on the host cell chosen as discussed below, and may be readily accomplished by one of ordinary skill in the art. Examples of such elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, and sequences conferring inducibility of transcription may be incorporated into the expression vector. It will also be appreciated that the necessary transcriptional and translation elements may be supplied by the native receptor tyrosine kinase protein and/or its flanking regions.

The recombinant molecules of the invention may also contain a reporter gene which facilitates the selection of host cells transformed or transfected with a recombinant molecule of the invention. Examples of reporter genes are genes encoding a protein such as β-galactosidase, chloramphenicol acetyltransferase, firefly luciferase, or an immunoglobulin or portion thereof such as the Fc portion of an immunoglobulin preferably IgG. In a preferred embodiment, the reporter gene is lac Z. Transcription of the reporter gene is monitored by changes in the concentration of the reporter protein such as β-galactosidase, chloramphenicol acetyltransferase, or firefly luciferase. This makes it possible to visualize and assay for expression of recombinant molecules of the invention and in particular to determine the effect of a mutation on expression and phenotype.

Recombinant molecules can be introduced into host cells via transformation, transfection, infection, electroporation etc. Methods for transforming transfecting, etc. host cells to express foreign DNA are well known in the art (see, e.g., Itakura et al., U.S. Pat. No. 4,704,362; Hinnen et al., PNAS USA 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. Molecular Cloning A Laboratory Manual, 2nd edition, Cold Spring Harbor Laboratory Press, 1989, all of which are incorporated herein by reference and see the detailed discussion below).

Suitable host cells include a wide variety of prokaryotic and eukaryotic host cells, including bacterial, mammalian, yeast or other fungi, viral, plant, or insect cells.

More particularly, bacterial host cells suitable for carrying out the present invention include *E. coli, B. subtilis, Salmonella typhimurium*, and various species within the genus' Pseudomonas, Streptomyces, and Staphylococcus, as well as many other bacterial species well known to one of ordinary skill in the art. Representative examples of bacterial host cells include DH5α (Stratagene, Lajolla, Calif.), JM109 ATCC No. 53323, HB101 ATCC No. 33694, and MN294. Suitable bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., Nature 275:615, 1978), the trp promoter (Nichols and Yanofsky, Meth in Enzymology 101:155, 1983) and the tac promoter (Russell et al., Gene 20: 231, 1982). Representative selectable markers include various antibiotic resistance markers such as the kanamycin or ampicillin resistance genes. Suitable expression vectors include but are not limited to bacteriophages such as lambda derivatives or plasmids such as pBR322 (see Bolivar et al., Gene 2:9S, 1977), the pUC plasmids pUC18, pUC19, pUC118, pUC119 (see Messing, Meth in Enzymology 101:20–77, 1983 and Vieira and Messing, Gene 19:259–268, 1982), and pNH8A, pNH16a, pNH18a, and Bluescript M13 (Stratagene, La Jolla, Calif.).

Yeast and fungi host cells suitable for carrying out the present invention include, among others *Saccharomyces cerevisae*, the genera Pichia or Kluyveromyces and various species of the genus Aspergillus. Suitable expression vectors for yeast and fungi include, among others, $YC_p50$ (ATCC No. 37419) for yeast, and the amdS cloning vector pV3 (Turnbull, Bio/Technology 7:169, 1989). Protocols for the transformation of yeast are also well known to those of ordinary skill in the art. For example, transformation may be readily accomplished either by preparation of spheroplasts of yeast with DNA (see Hinnen et al., PNAS USA 75:1929, 1978) or by treatment with alkaline salts such as LiCl (see Itoh et al., J. Bacteriology 153:163, 1983). Transformation of fungi may also be carried out using polyethylene glycol as described by Cullen et al. (Bio/Technology 5:369, 1987).

Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter, as well as other transcriptional and translational control sequences. Common promoters include SV40, MMTV, metallothionein-1, adenovirus Ela, CMV, immediate early, immunoglobulin heavy chain promoter and enhancer, and RSV-LTR. Protocols for the transfection of mammalian cells are well known to those of ordinary skill in the art. Representative methods include calcium phosphate mediated electroporation, retroviral, and protoplast fusion-mediated transfection (see Sambrook et al., supra).

Given the teachings provided herein, promoters, terminators, and methods for introducing expression vectors of an appropriate type into plant, avian, and insect cells may also be readily accomplished. For example, within one embodiment, Nuk or derivatives thereof may be expressed from plant cells (see Sinkar et al., J. Biosci (Bangalore) 11:47–58, 1987, which reviews the use of *Agrobacterium rhizogenes* vectors; see also Zambryski et al., Genetic Engineering, Principles and Methods, Hollaender and Setlow (eds.), Vol. VI, pp. 253–278, Plenum Press, New York, 1984, which describes the use of expression vectors for plant cells, including, among others, pAS2022, pAS2023, and pAS2034).

Insect cells suitable for carrying out the present invention include cells and cell lines from Bombyx or Spodotera species. Suitable expression vectors for directing expression in insect cells include Baculoviruses such as the *Autographa California* nuclear polyhedrosis, virus (Miller et al. 1987, in *Genetic Engineering*, Vol. 8 ed. Setler, J. K. et al., Plenum Press, New York) and the *Bombyx mori* nuclear polyhedrosis virus (Maeda et al., 1985, Nature 315:592).

Alternatively, Nuk may be expressed in non-human transgenic animals such as, mice, rats, rabbits, sheep and pigs (see Hammer et al. (Nature 315:680–683, 1985), Palmiter et al. (Science 222:809–814, 1983), Brinster et al. (Proc Natl. Acad. Sci USA 82:44384442, 1985), Palmiter and Brinster (Cell. 41:343–345, 1985) and U.S. Pat. No. 4,736,866).

The Nuk protein or parts thereof may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

Conjugates of the Nuk protein of the invention, or parts thereof, with other molecules, such as proteins or polypeptides, may be prepared. This may be accomplished, for example, by the synthesis of N-terminal or C-terminal fusion proteins. Thus, fusion proteins may be prepared by fusing, through recombinant techniques, the N-terminal or C-terminal of Nuk protein or parts thereof, and the sequence of a selected protein or marker protein with a desired biological function. The resultant fusion proteins contain Nuk protein or a portion thereof fused to the selected protein or marker protein as described herein. Examples of proteins which may be used to prepare fusion proteins include immunoglobulins and parts thereof such as the constant region of immunoglobulin γ1, and lymphokines such as gamma interferon, tumor necrosis factor, IL-1, IL-2, IL-3, Il-4, IL-5, IL-6, IL-7, IL-8, IL-9, IL-10, IL-11, GM-CSF, CSF-1 and G-CSF.

Sequences which encode the above-described proteins may generally be obtained from a variety of sources, including for example, depositories which contain plasmids encoding sequences including the American Type Culture Collection (ATCC, Rockville Md.), and the British Biotechnology Limited (Cowley, Oxford England). Examples of such plasmids include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon,) ATCC Nos. 31902 and 39517 (which contains sequences encoding beta interferon), ATCC No. 67024 (which contains a sequence which encodes Interleukin-1β), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC Nos. 57592 (which contains sequences encoding Interleukin-4). ATCC Nos. 59394 and 59395 (which contain sequences encoding Interleukin-5), and ATCC No. 67153 (which contains sequences encoding Interleukin-6).

Within a particularly preferred embodiment of the invention, Nuk is cloned into an expression vector as a fusion gene with the constant region of human immunoglobulin γ1. Briefly, the expression vectors pNUTΔGH and pVL1393 are prepared for cloning by digestion with SmaI followed by dephosphorylation by calf intestinal alkaline phosphatase. The linear product is isolated after agarose gel electrophoresis. The Nuk genes are then generated by polymerase chain reaction using the cloned Nuk cDNA as a template. In particular, the Nuk fusion protein is synthesized from the extracelluar domain of Nuk protein, preferably amino acids 26 to 548, SEQ ID NO: 2 and FIG. 2. In another embodiment, the Nuk fusion protein is synthesized from the carboxy terminal tail of Nuk protein, preferably amino acids 601 to 994, SEQ ID NO:2 and FIG. 2.

The constant region of an immunoglobulin, such as human γ1 gene may be prepared, for example, from pUCB7Ig monomer. Briefly, the $C_H$ gene is isolated by digestion with XbaI which cuts at the 3' end of the gene followed by treatment with *E. coli* DNA polymerase I in the presence of all four dNTPs in order to create a blunt end. The plasmid is then digested with BclI which cuts at the 5' end of the gene. The fragment containing the heavy chain gene is isolated after electrophoresis in an agarose gel.

The fusion Nuk amplified fragment is inserted into each prepared vector along with the heavy chain fragment. Orientation of the resulting plasmids is determined by PCR with one priming oligo which anneals to the vector sequence and the other priming oligo which anneals to the insert sequence. Alternatively, appropriate restriction digests can be performed to verify the orientation. The sequence of the fusion Nuk/immunoglobulin constant region gene can be verified by DNA sequencing.

Phosphorylated receptor tyrosine kinase proteins of the invention, or parts thereof, may be prepared using the method described in Reedijk et al. The EMBO Journal 11(4):1365, 1992. For example, tyrosine phosphorylation may be induced by infecting bacteria harbouring a plasmid containing a nucleotide sequence of the invention or fragment thereof, with a λgt11 bacteriophage encoding the cytoplasmic domain of the Elk tyrosine kinase. Bacteria containing the plasmid and bacteriophage as a lysogen are isolated. Following induction of the lysogen, the expressed receptor protein becomes phosphorylated.

IV. Utility of the Nucleic Acid Molecules and Proteins of the Invention

The nucleic acid molecules of the invention or fragments thereof, allow those skilled in the art to construct nucleotide probes for use in the detection of nucleotide sequences in biological materials. A nucleotide probe may be labelled with a detectable substance such as a radioactive label which provides for an adequate signal and has sufficient half-life such as $^{32}P$, $^3H$, $^{14}C$ or the like. Other detectable substances which may be used include antigens that are recognized by a specific labelled antibody, fluorescent compounds, enzymes, antibodies specific for a labelled antigen, and luminescent compounds. An appropriate label may be selected having regard to the rate of hybridization and binding of the probe to the nucleotide to be detected and the amount of nucleotide available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleotide probes may be used to detect genes, preferably in human cells, that encode proteins related to or analogous to the receptor tyrosine kinase protein of the invention. The nucleotide probes may therefore be useful in the diagnosis of disorders of the nervous system arising from mutations or alterations to the Nuk gene or a homologue thereof.

The receptor tyrosine kinase protein of the invention and portions thereof, for example amino acids of the carboxy terminal tail, preferably amino acids 601 to 994; or amino acids of the extracellular domain, preferably amino acids 26 to 548 more preferably 26 to 544 (SEQ ID NO: 2 and FIG. 2), may be used to prepare antibodies. Antibodies having specificity for Nuk protein may also be raised from fusion proteins created by expressing trpE-Nuk fusion proteins in bacteria as described above.

Within the context of the present invention, antibodies are understood to include monoclonal antibodies, polyclonal antibodies, antibody fragments (e.g., Fab, and F(ab')$_2$ and recombinantly produced binding partners. Antibodies are understood to be reactive against Nuk protein if they bind with a $K_a$ of greater than or equal to $10^{-7}$ M. As will be appreciated by one of ordinary skill in the art, antibodies may be developed which not only bind to Nuk protein, but which bind to a ligand of Nuk protein, and which also block the biological activity of Nuk protein. Such antibodies will be useful in the diagnosis and treatment of disorders of the nervous system and nerve damage.

Polyclonal antibodies may be readily generated by one of ordinary skill in the art from a variety of warm-blooded animals such as horses, cows, various fowl, rabbits, mice, or rats. Briefly, Nuk protein is utilized to immunize the animal through intraperitoneal, intramuscular, intraocular, or subcutaneous injections, in conjunction with an adjuvant such as Freund's complete or incomplete adjuvant. Following several booster immunizations, samples of serum are collected and tested for reactivity to Nuk protein. Particularly preferred polyclonal antisera will give a signal on one of these assays that is at least three times greater than background. Once the titer of the animal has reached a plateau in terms of its reactivity to Nuk protein, larger quantities of antisera may be readily obtained either by weekly bleedings, or by exsanguinating the animal.

Monoclonal antibodies may also be readily generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Briefly, within one embodiment a subject animal such as a rat or mouse is injected with Nuk protein. The Nuk protein may be admixed with an adjuvant such as Freund's complete or incomplete adjuvant in order to increase the resultant immune response. Between one and three weeks after the initial immunization the animal may be reimmunized with another booster immunization, and tested for reactivity to Nuk protein using assays described above. Once the animal has plateaued in its reactivity to Nuk protein, it is sacrificed, and organs which contain large numbers of B cells such as the spleen and lymph nodes are harvested.

Cells which are obtained from the immunized animal may be immortalized by transfection with a virus such as the Epstein bar virus (EBV) (see Glasky and Reading, Hybridoma 8(4):377–389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines include, for example, NS-1 (ATCC No. TIB 18), and P3X63—Ag 8.653 (ATCC No. CRL 1580).

Following the fusion, the cells may be placed into culture plates containing a suitable medium, such as RPMI 1640, or DMEM (Dulbecco's Modified Eagles Medium) (JRH Biosciences, Lenexa, Kans.), as well as additional ingredients, such as Fetal Bovine Serum (FBS, ie., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against Nuk protein. A wide variety of assays may be utilized to determine the presence of antibodies which are reactive against Nuk protein, including for example Countercurrent Immuno-Electrophoresis, Radioimmunoassays, Radioimmunoprecipitations, Enzyme-Linked Immuno-Sorbent Assays (ELISA), Dot Blot assays, Inhibition or Competition Assays, and sandwich assays (see U.S. Pat. Nos. 4,376,110 and 4,186,530; see also Antibodies: A Laboratory Manual, Harlow and Lane (eds.), Cold Spring Harbor Laboratory Press, 1988). Following several clonal dilutions and reassays, a hybridoma producing antibodies reactive against Nuk protein may be isolated.

Other techniques may also be utilized to construct monoclonal antibodies (see William D. Huse et al., "Generation of a Large Combinational Library of the Immunoglobulin Repertoire in Phage Lambda," Science 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," Proc Natl. Acad. Sci USA 86:5728–5732, August 1989; see also Michelle Alting-Mees et al., "Monoclonal Antibody Expression Libraries: A Rapid Alternative to Hybridomas," Strategies in Molecular Biology 3:1–9, January 1990; these references describe a commercial system available from Stratacyte, La Jolla, Calif., which enables the production of antibodies through recombinant techniques). Briefly, mRNA is isolated from a B cell population, and utilized to create heavy and light chain immunoglobulin cDNA expression libraries in the λImmunoZap(H) and λImmunoZap(L) vectors. These vectors may be screened individually or co-expressed to form Fab fragments or antibodies (see Huse et al. supra; see also Sastry et al., supra). Positive plaques may subsequently be converted to a non-lytic plasmid which allows high level expression of monoclonal antibody fragments from *E. coli*.

Similarly, binding partners may also be constructed utilizing recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Primers for mouse and human variable regions including, among others, primers for $V_{Ha}$, $V_{Hb}$, $V_{Hc}$, $V_{Hd}$, $C_{H1}$, $V_L$ and $C_L$ regions are available from Stratacyte (La Jolla, Calif.). These primers may be utilized to amplify heavy or light chain variable regions, which may then be inserted into vectors such as ImmunoZAP™ H or ImmunoZAP™ L (Stratacyte), respectively. These vectors may then be introduced into *E. coli* for expression. Utilizing these techniques, large amounts of a single-chain protein containing a fusion of the VH and VL domains may be produced (See Bird et al., Science 242:423–426, 1988). In addition, such techniques may be utilized to change a "murine" antibody to a "human" antibody, without altering the binding specificity of the antibody.

Once suitable antibodies or binding partners have been obtained, they may be isolated or purified by many techniques well known to those of ordinary skill in the art (see Antibodies: A Laboratory Manual, Harlow and Lane (eds.), Cold Spring Harbor Laboratory Press, 1988). Suitable techniques include peptide or protein affinity columns, HPLC or RR-HPLC, purification on protein A or protein G columns, or any combination of these techniques.

The polyclonal or monoclonal antibodies may be used to detect the receptor tyrosine kinase protein of the invention in various biological materials, for example they may be used in an ELISA, radioimmunoassay or histochemical tests. Thus, the antibodies may be used to quantify the amount of a receptor tyrosine kinase protein of the invention in a sample in order to determine its role in particular cellular events or pathological states and to diagnose and treat such pathological states.

In particular, the polyclonal and monoclonal antibodies of the invention may be used in immuno-histochemical analyses, for example, at the cellular and sub-subcellular level, to detect the novel receptor tyrosine kinase protein of the invention, to localise it to particular cells and tissues and to specific subcellular locations, and to quantitate the level of expression.

Cytochemical techniques known in the art for localizing antigens using light and electron microscopy may be used to detect the novel tyrosine kinase of the invention. Generally, an antibody of the invention may be labelled with a detectable substance and the novel receptor tyrosine kinase of the invention may be localised in tissue based upon the presence of the detectable substance. Examples of detectable substances include various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine $I^{125}$, $I^{131}$ or tritium. Antibodies may also be coupled to electron dense substances, such as ferritin or colloidal gold, which are readily visualised by electron microscopy.

Radioactive labelled materials may be prepared by radiolabeling with $^{125}I$ by the chloramine-T method (Greenwood et al, Biochem. J. 89:114, 1963), the lactoperoxidase method (Marchalonis et al, Biochem. J. 124:921, 1971), the Bolton-Hunter method (Bolton and Hunter, Biochem. J. 133:529, 1973 and Bolton Review 18, Amersham International Limited, Buckinghamshire, England, 1977), the iodogen method (Fraker and Speck, Biochem. Biophys. Res. Commun. 80:849, 1978), the Iodo-beads method (Markwell Anal. Biochem. 125:427, 1982) or with tritium by reductive methylation (Tack et al., J. Biol. Chem. 255:8842, 1980).

Known coupling methods (for example Wilson and Nakane, in "Immunofluorescence and Related Staining Techniques", W. Knapp et al, eds, p. 215, Elsevier/North-Holland, Amsterdam & New York, 1978; P. Tijssen and E. Kurstak, Anal. Biochem. 136:451, 1984) may be used to prepare enzyme labelled materials. Fluorescent labelled materials may be prepared by reacting the material with umbelliferone, fluorescein, fluorescein isothiocyanate, dichlorotriazinylamine fluorescein, dansyl chloride, derivatives of rhodamine such as tetramethyl rhodamine isothiocyanate, or phycoerythrin.

Indirect methods may also be employed in which the primary antigen-antibody reaction is amplified by the introduction of a second antibody, having specificity for the antibody reactive against the novel tyrosine kinase of the invention. By way of example, if the antibody having specificity against the novel tyrosine kinase protein of the invention is a rabbit IgG antibody, the second antibody may be goat anti-rabbit gamma-globulin labelled with a detectable substance as described herein.

Where a radioactive label is used as a detectable substance, the novel tyrosine kinase of the invention may be localized by radioautography. The results of radioautography may be quantitated by determining the density of particles in the radioautographs by various optical methods, or by counting the grains.

As discussed above, the expression patterns found for the novel tyrosine kinase of the invention indicate that it plays unique and important roles in the determination, migration and pathfinding of axons, in axogenesis and fasciculation, development and regeneration of the neural tube, and in the regulation of specific cell—cell interactions during early development of the nervous system. Therefore, the above described methods for detecting nucleic acid molecules and fragments thereof and Nuk protein and parts thereof, can be used to monitor vertebrate axonal migration, fasciculation and regeneration by detecting and localizing the novel tyrosine kinase protein of the invention in migrating axons and in the migrating membrane surface of cells of the developing nervous system.

It would also be apparent to one skilled in the art that the above described methods may be used to study the developmental expression of Nuk and, accordingly, will provide further insight into the role of Nuk protein in neuronal cell:cell interactions in embryogenic development and in axonogenesis and nerve regeneration.

The finding of a novel receptor tyrosine kinase protein which is expressed in migrating axons and the developing neural tube permits the identification of substances which may affect axonogenesis, neural embryonic development and neuron regeneration. A substance which affects expression of Nuk protein may be assayed using the above described methods for detecting nucleic acid molecules and fragments thereof and Nuk protein and parts thereof, by comparing the pattern and level of expression of the Nuk protein or parts thereof, in the presence and absence of the substance.

The invention also provides methods for identifying substances which are capable of binding to the Nuk protein, or isoforms and parts thereof. In particular, the methods may be used to identify ligands and natural and synthetic derivatives of such ligands, which are capable of binding to and in some cases activating the receptor tyrosine kinase protein of the invention, isoforms thereof, or part of the protein. The method may also be used to identify substances which are capable of binding to and themselves being activated or phosphorylated by the Nuk protein.

Substances which can bind with the receptor tyrosine kinase protein of the invention may be identified by reacting the novel receptor tyrosine kinase protein which is expressed in migrating vertebrate axons isoforms thereof, or part of the protein, with a substance which potentially binds to the novel receptor tyrosine kinase protein, isoforms thereof, or part of the protein such as the extracelluar domain, and assaying for substance-receptor complexes, for free substance or for non-complexed receptor tyrosine kinase protein isoforms thereof or part of the protein, or for activation of the receptor tyrosine kinase protein or the substance.

Conditions which permit the formation of substance-receptor protein complexes may be selected having regard to factors such as the nature and amounts of the substance and the receptor protein.

The substance-receptor complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against the receptor protein or the substance, or a labelled receptor protein, or a labelled substance may be utilized. Antibodies, receptor protein or substance may be labelled with a detectable substance as described above.

The receptor tyrosine kinase protein, isoforms or parts thereof, or substance used in the method of the invention may be insolubilized. For example, the receptor protein or substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized receptor tyrosine kinase protein or substance may be prepared by reacting the material with a suitable insoluble carrier using known chemical or physical methods, for example, cyanogen bromide coupling.

The receptor tyrosine kinase protein, parts thereof, or substance may also be expressed on the surface of a cell using the methods described herein. Where the substance is expressed on the surface of a cell the presence of a substance which can bind to and be activated by the receptor tyrosine kinase protein may be identified by assaying for activation or phosphorylation of the substance or by assaying for a biological affect on the cell.

The above mentioned methods of the invention may be used to identify ligands which bind with and activate the novel receptor tyrosine kinase protein of the invention thereby affecting signalling pathways, particularly those involved in neuronal development and axonal migration and regeneration. Identification and isolation of such a Nuk protein ligand will permit studies of the role of the ligand in the developmental regulation of axonogenesis and neural regeneration, and permit the development of substances which affect these roles, such as functional or non-functional analogues of the ligand. It will be appreciated that such substances will be useful as pharmaceuticals to modulate axonogenesis, nerve cell interactions and regeneration to treat conditions such as neurodegenerative diseases and cases of nerve injury.

Ligands which bind to and activate the novel receptor tyrosine kinase protein of the invention may be identified by assaying for protein tyrosine kinase activity i.e. by assaying for phosphorylation of the tyrosine residues of the novel receptor tyrosine kinase protein.

Receptor tyrosine kinase protein activity may be assayed using known techniques such as those using anti-phosphotyrosine antibodies and labelled phosphorous. For example, immunoblots of the complexes may be analyzed by autoradiography ($^{32}$P-labelled samples) or may be blocked and probed with antiphosphotyrosine antibodies as described in Koch, C. A. et al (1989) Mol. Cell. Biol. 9, 4131–4140.

The ligands for many receptor tyrosine kinase proteins are cell-bound, either as they are associated with the cell surface via heparin and hepatocyte growth factor or because they are transmembrane proteins (Lyman et al. 1993, supra). Ligands for receptor tyrosine kinases of the Eph/Elk/Eck subfamily of receptor tyrosine kinases may require cell-to-cell contact to activate the receptor. Membrane attachment of the ligand could facilitate ligand dimerization or clustering, or both, which may promote receptor multimerization and activation.

Accordingly, a ligand for Nuk protein may have a cell-bound form. A cell-bound ligand may be identified by reacting the receptor tyrosine kinase protein of the invention, an isoform or a part thereof with a cell suspected of expressing the ligand on the surface of the cell following the procedures generally described in Lyman et al., 1993, (Cell 75:1157–1167). Thus, the invention provides a method for identifying cells expressing a surface bound ligand of Nuk protein and for specifically selecting for such cells.

By way of example, a cDNA encoding a ligand for Nuk protein may be cloned by first constructing a fusion protein. The fusion protein may consist of the extracelluar domain of Nuk protein (amino acids 26 to 548, SEQ ID NO: 2 and FIG. 2). The fusion protein may be expressed and used as a probe to examine cells or cell lines (e.g. neuroblastoma or neuroepitheliomia cell lines) for their capacity to bind the extracellular domain of Nuk protein (determined by flow cytometry). The identification of cells and cell lines that bind the extracellular domain may be facilitated by incorporating in the fusion protein a sequence encoding a marker protein for example, the Fc portion of human IgG which may be detected with labelled anti-human IgG antibodies. Cells or cell lines which bind the extracellular domain are presumed to express a cell-bound form of the ligand.

Following identification of a source of the Nuk ligand, a cDNA expression library is constructed, following known techniques, using mRNA from the cells/cell lines which have been identified as binding the fusion protein containing the extracellular domain of Nuk protein. cDNAs are then transfected into host cells (e.g. COS cells and see discussion herein re host cells) which are then screened for their capacity to bind the extracellular domain of Nuk protein. Individual clones which are capable of binding the extracellular domain of Nuk protein are identified and the cDNAs are sequenced. The cDNAs may be used as hybridization probes to isolate genomic DNA encoding the ligand.

It will be appreciated that the methods of the invention may be used to identify substances which bind to and are activated by Nuk protein or which transmit a signal to activate intracellular signalling proteins. It is anticipated that the ligands of Nuk protein identified by the methods of the invention may themselves be activated or phosphorylated by binding to the extracellular domain of Nuk protein. Binding of the extracellular domain of Nuk protein to a ligand expressed on a cell surface may activate downstream regulatory pathways in the ligand-expressing cell, such as the GAP/Ras pathway, the pathway that regulates the breakdown of the polyphosphoinositides through phospholipase C and Src/tyrosine kinase and Ras pathways.

Ligands of the Eph subfamily of receptor tyrosine kinases, including Nuk protein, have recently been identified and they are all membrane anchored via either a GPI linkage or a transmembrane domain. Such ligands include ELF-1, AL-1, EHK-1L, B61, LERK-4, HTKL, LERK-5 and LERK-2, collectively known as Lerks (Tessier-Lavigne, M Cell, 1995, 82:345–348). These ligands are known to have promiscuous interactions with the Eph receptor family members. In particular, LERK 2 and LERK-5 are known to bind to Nuk protein. These ligands may be involved in SH2-mediated intracellular signal transduction. The ligands have been implicated in conveying positional information to pathfinding axons as, being membrane anchored, they are capable of conveying positional information. The extracellular domain of Nuk protein may function to signal adjacent cells expressing substances capable of binding to and being activated by Nuk protein and to control the cells' spatial positioning, development, migration, pathfinding or survival. Interaction of the extracellular domain of Nuk protein on the surface of a cell with a substance capable of binding Nuk protein on a second cell (e.g. Lerks) such as a migrating axon, may provide a signal to the second cell resulting in an attractive or repulsive effect. Nuk protein may play a crucial role in two way signal transduction as shown in FIG. 27.

The invention also contemplates a method for assaying for an agonist or antagonist of the binding of the novel receptor tyrosine kinase of the invention with a substance which is capable of binding with the novel tyrosine kinase protein, preferably a ligand or a substance which is capable of being activated by binding with the novel tyrosine kinase protein. The agonist or antagonist may be an endogenous physiological substance or it may be a natural or synthetic drug. Substances which are capable of binding with the Nuk protein and preferably ligands, including cell-bound ligands may be identified using the methods set forth herein. Substances which bind to other receptor tyrosine kinases of the Eph/Elk/Eck subfamily may also be used in this assay. For example, the substance may be LERK-2, a binding protein for the receptor-tyrosine kinase ELK (Fletcher, F. A. et al., Oncogene (1994), 9, 3241–3247), or the cell-bound ligands B61 (also known as EFL-1), EHK1-L (also known as EFL-2) and ELK-L (also known as EFL-3)(Davis, S. et al., Science Vol. 266, p.816, Nov. 4, 1994). Other binding proteins of the receptors of the Eph/Elk/Eck subfamily include ELF-1, AL-1, EHK-1L, B61, LERK-4, HTKL, LERK-5 and LERK-2 (Tessier-Lavigne, M Cell, 1995, 82:345–348).

In accordance with a preferred embodiment, a method is provided which comprises providing a known concentration of the novel receptor tyrosine kinase protein of the invention, incubating the protein with a ligand which can bind to and activate the protein, and a suspected agonist or antagonist under conditions which permit the formation of substance-receptor protein complexes, and assaying for substance-receptor protein complexes, for free substance, for non-complexed proteins, or for activation of the receptor tyrosine kinase protein or ligand. Conditions which permit the formation of substance-receptor protein complexes, and methods for assaying for substance-receptor protein complexes, for free substance, for non-complexed proteins, or for activation of the receptor tyrosine kinase protein or the ligand are described herein.

It will be understood that the agonists and antagonists that can be assayed using the methods of the invention may act on one or more of the binding sites on the receptor tyrosine kinase or the ligand, including agonist binding sites, competitive antagonist binding sites, non-competitive antagonist binding sites or allosteric sites.

The invention also makes it possible to screen for antagonists that inhibit the effects of an agonist of the interaction of Nuk protein with a Nuk protein ligand. Thus, the invention may be used to assay for a substance that competes for the same ligand binding site of the novel receptor tyrosine kinase protein of the invention.

The invention further contemplates a method for identifying a substance which is capable of binding to an activated receptor tyrosine kinase protein of the invention or an isoform or part of the activated protein, comprising reacting an activated receptor tyrosine kinase protein of the invention, or an isoform, or part of the protein, with at least one substance which potentially can bind with the receptor tyrosine kinase protein, isoform or part of the protein, under conditions which permit the formation of substance-receptor kinase protein complexes, and assaying for substance-receptor kinase protein complexes, for free substance, for non-complexed receptor kinase proteins, or for phosphorylation of the receptor kinase substance.

An activated receptor tyrosine kinase protein of the invention, or isoform or part thereof may be prepared by binding of a ligand to the extracellular domain of a receptor tyrosine kinase protein of the invention which results in activation of the catalytic domain. Such a ligand may be identified using the methods hereinbefore described. An activated receptor or part thereof, may also be prepared using the methods described for example in Reedijk et al. The EMBO Journal, 11(4):1365, 1992 for producing a tyrosine phosphorylated receptor or part thereof.

Conditions which permit the formation of substance-receptor protein complexes may be selected having regard to factors such as the nature and amounts of the substance and the receptor protein. The substance-receptor complex, free substance or non-complexed proteins may be isolated by conventional isolation techniques described above. Phosphorylation of the substance may be determined using for example, labelled phosphorous as described above.

In an embodiment of this method, intracellular ligands such as Src homology region 2 (SH2)-containing proteins which are capable of binding to a phosphorylated activated receptor tyrosine kinase protein of the invention may be identified. SH2-containing proteins refers to proteins containing a Src homology region 2 which is a noncatalytic domain of ~100 amino acids which was originally identified in the Vfps and Vsrc cytoplasmic tyrosine kinases by virtue of its effects on both catalytic activity and substrate phosphorylation (T. Pawson, Oncogene 3, 491 (1988) and I. Sadowski et al., Mol. Cell. Biol. 6, 4396 (1986)). (See also Koch et al., Science 252:668, 1991; Moran et al., PNAS USA 87:8622 and Anderson et al., Science 250:979, 1990 for discussions on SH2-containing proteins and the role of SH2 domains). SH2-containing proteins may function downstream of the Nuk signalling pathway by binding to the activated receptor protein. For example, the cytoplasmic tyrosine kinases of the Src family may bind via their SH2 domains to the activated Nuk receptor protein thereby regulating cellular processes particularly in the nervous system. Intracellular ligands which may be phosphorylated by the novel receptor tyrosine kinase of the invention may also be identified using the method of the invention.

SH2-domains of cytoplasmic signalling proteins have been found to bind to the phosphorylated receptor tyrosine kinase protein of the invention. In particular, the SH2 domains of $p21^{ras}$ GTPase-activating protein (GAP), Src, and phosphoinositide-specific phospholipase C (PLCγ) have been found to bind Nuk protein. The SH-2 domain binding site on the Nuk protein is a conserved tyrosine containing region which is located adjacent to the membrane and it corresponds to amino acids 600 to 618 as shown in SEQ. ID. NO:2 in the Sequence Listing.

Therefore, the invention also contemplates a method for assaying for an agonist or antagonist of the binding of an activated receptor tyrosine kinase of the invention, or a portion thereof with an SH2 domain of an intracellular ligand. The agonist or antagonist may be an endogenous physiological substance or it may be a natural or synthetic drug. The activated receptor may be prepared as described herein or a portion of the ligand comprising the amino acid sequence 600 to 618 as shown in SEQ. ID. NO:2 in the Sequence Listing may be used in this method of the invention. Examples of SH2 domains of intracellular ligands include the SH2 domains of GAP, Src, and PLCγ. It will be appreciated that the entire intracellular ligand may be used in this method.

It has also been found that COS cells express large amounts of Nuk protein. Accordingly, COS cells may be used to identify in vivo, intracellular proteins or ligands which bind to the Nuk protein. COS cells may also be used to identify substances which are expressed on the surfaces of other cells which are capable of binding to and being activated by the Nuk protein expressed by the COS cell.

The invention further provides a method for assaying for a substance that affects axonal migration, neural development, nerve cell interactions and nerve regeneration comprising administering to a non-human animal or to a tissue of an animal, a substance suspected of affecting axonal migration, and detecting, and optionally quantitating, the novel receptor tyrosine kinase of the invention in the non-human animal or tissue. In an embodiment of the invention, the method may be used to assay for a substance that affects axonal migration during embryogenesis. The novel receptor tyrosine kinase of the invention may be quantitated using the methods described herein.

In another embodiment, the method may be used to assay for a substance that affects axonal migration in nerve regeneration, comprising administering a substance suspected of affecting axonal migration to a non-human animal having an injured peripheral nervous system and detecting, and optionally quantitating, the novel receptor tyrosine kinase of the invention in the non-human animal. Examples of non-human animals having an injured peripheral nervous system include animals having damaged axons, such as axotomized facial neurons (Sendtner et al. Nature, 345, 440–441, 1990), neurodegenerative conditions (for example, the MPTP model as described in Langston J. W. et al., Symposium of Current Concepts and Controversies in Parkinson's Disease, Montebello, Quebec, Canada, 1983 and Tatton W. G. et al., Can. J. Neurol. Sci. 1992, 19), and traumatic and non-traumatic peripheral nerve damage (for example, animal stroke models such as the one described in MacMillan et al. Brain Research 151:353–368 (1978)).

Substances which are capable of binding to the Nuk protein of the invention or parts thereof, particularly ligands, and agonists and antagonists of the binding of ligands and Nuk protein, or parts thereof identified by the methods of the invention, may be used for stimulating or inhibiting neuronal development, regeneration and axonal migration. The ligands, agonists, antagonists receptor tyrosine kinase protein and parts thereof may accordingly be used to stimulate or inhibit neuronal development, regeneration and axonal migration associated with neurodegenerative conditions and conditions involving trauma and injury to the nervous system, for example Alzheimer's disease, Parkinson's disease, Huntington's disease, demylinating diseases, such as multiple sclerosis, amyotrophic lateral sclerosis, bacterial and viral infections of the nervous system, deficiency diseases, such as Wernicke's disease and nutritional polyneuropathy, progressive supranuclear palsy, Shy Drager's syndrome, multistem degeneration and olivo ponto cerebellar atrophy, peripheral nerve damage, trauma and ischemia resulting from stroke.

Accordingly, the invention also provides pharmaceutical compositions and methods for affecting neuronal development and regeneration, in particular for stimulating or inhibiting neuronal development, regeneration and axonal migration, preferably for stimulating axonogenesis.

The present inventors have directly demonstrated that Nuk protein plays a role in neuronal development, axonogenesis and in the formation and pathfinding of major axon pathways of the central nervous system. Nuk protein may also play a role as a survival factor in the survival of neurons or other cell types in the CNS or PNS, such as astrocytes or Schwan cells. The pharmaceutical composition may contain Nuk protein or protein fragments of the invention in combination with pharmaceutically acceptable carriers, diluents or excipients. Suitable fragments include the extracellular domain of Nuk protein, for example from amino acids number 26 to 548, preferably from 26 to 544, as shown in SEQ ID NO:2 or portions thereof.

The pharmaceutical compositions may accordingly be used to stimulate or inhibit neuronal development, regeneration and axonal migration associated with neurodegenerative conditions and conditions involving trauma and injury to the nervous system, for example Alzheimer's disease, Parkinson's disease, Huntington's disease, demylinating diseases, such as multiple sclerosis, amyotrophic lateral sclerosis, bacterial and viral infections of the nervous system, deficiency diseases, such as Wernicke's disease and nutritional polyneuropathy, progressive supranuclear palsy, Shy Drager's syndrome, multistem degeneration and olivo ponto cerebellar atrophy, peripheral nerve damage, trauma and ischemia resulting from stroke.

The compositions of the invention are administered to subjects in a biologically compatible form suitable for pharmaceutical administration in vivo. By "biologically compatible form suitable for administration in vivo" is meant a form of the protein to be administered in which any toxic effects are outweighed by the therapeutic effects of the protein. The term subject is intended to include mammals. Examples of subjects include humans, dogs, cats, mice, rats, and transgenic species thereof. Administration of a therapeutically active amount of the pharmaceutical compositions of the present invention is defined as an amount effective, at dosages and for periods of time necessary to achieve the desired result. For example, a therapeutically active amount of Nuk protein of the invention may vary according to factors such as the condition, age, sex, and weight of the individual. Dosage regimes may be adjusted to provide the optimum therapeutic response. For example, several divided doses may be administered daily or the dose may be proportionally reduced as indicated by the exigencies of the therapeutic situation.

The active compound (e.g., protein) may be administered in a convenient manner such as by injection (subcutaneous, intravenous, etc.), oral administration inhalation, transdermal application or rectal administration. Depending on the route of administration, the active compound may be coated in a material to protect the compound from the action of enzymes, acids and other natural conditions which may inactive the compound. The pharmaceutical compositions of the invention can be for oral, local, inhalant or intracerebral administration. Preferably, the pharmaceutical compositions of the invention are administered directly to the peripheral or central nervous system, for example by administration intracerebrally.

The pharmaceutical composition of the invention can be administered to a subject in an appropriate carrier or diluent, co-administered with enzyme inhibitors or in an appropriate carrier such as microporous or solid beads or liposomes. The term "pharmaceutically acceptable carrier" as used herein is intended to include diluents such as saline and aqueous buffer solutions. Liposomes include water-in-oil-in-water emulsions as well as conventional liposomes (Strejan et al., (1984) J. Neuroimmunol 7:27). The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

It is also contemplated that the pharmaceutical compositions of the invention may comprise cells or viruses, preferably retroviral vectors, transformed with the nucleic acid molecules of the invention and capable of expressing Nuk protein or a part of the protein, preferably the extracellular domain, in vivo. Viral vectors suitable for use in the present invention are well known in the art including recombinant vaccinia viral vectors (U.S. Pat. Nos. 4,603,112 and 4,769,330), recombinant pox virus vectors (PCT Publication No. WO 89/01973), and preferably, retroviral vectors ("Recombinant Retroviruses with Arnphotropic and Ecotropic Host Ranges," PCT Publication No. WO 90/02806; "Retroviral Packaging Cell Lines and Processes of Using Same," PCT Publication No. WO 89/07150; and "Antisense RNA for Treatment of Retroviral Disease States," PCT Publication No. WO 87/03451).

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., Nuk protein or portions thereof) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antibody) plus any additional desired ingredient from a previously sterile-filtered solution thereof.

When the active compound is suitably protected, as described above, the composition may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is contemplated that the pharmaceutical compositions may be administered locally to stimulate axonogenesis in areas of the body in need thereof, for example in areas of local nerve injury or in areas where normal nerve pathway development has not occurred. It is also contemplated that the pharmaceutical compositions may be placed in a specific orientation or alignment along a presumptive pathway to stimulate axon pathfinding along that line, for example the pharmaceutical compositions may be present on microcarriers laid down along the pathway. In an embodiment, the pharmaceutical compositions may be used to stimulate formation of connections or commissures between areas of brain, such as the between the two hemispheres or between the thalamus and ventral midbrain. In an embodiment, the compositions may be used to stimulate formation of the medial tract of the anterior commissure or the habenular interpeduncle.

The invention further provides a method for stimulating axonogenesis in a mammal in need of such stimulation. Such a mammal would include a mammal having nerve damage resulting, for instance, from trauma, neurodegenerative disorders or diseases, such as amyotrophic lateral sclerosis, Alzheimers' and Parkinsons' disease, brain damage due to hypoxia, ischemia, stroke, trauma, aging or damage of the central or peripheral nervous system. The method relates to the administration of the protein of the invention or part of the protein, or of the pharmaceutical compositions of the invention, as described above for stimulating or inhibiting neuronal development, regeneration and axonal migration, preferably for stimulating axonogenesis.

The invention also provides methods for studying the function of the Nuk protein. Cells, tissues, and non-human animals lacking in Nuk expression or partially lacking in Nuk expression may be developed using recombinant molecules of the invention having specific deletion or insertion mutations in the Nuk gene. For example, the extracellular domain or parts thereof, such as the FN III and Ig domains; the transmembrane region or parts thereof; the tyrosine kinase domain or parts thereof, such as the ATP binding site and; the carboxy terminal tail may be deleted. A recombinant molecule may be used to inactivate or alter the endogenous gene by homologous recombination, and thereby create a Nuk deficient cell, tissue or animal.

Null alleles may be generated in cells, such as embryonic stem cells by deletion mutation. A recombinant Nuk gene may also be engineered to contain an insertion mutation which inactivates Nuk. Such a construct may then be introduced into a cell, such as an embryonic stem cell, by a technique such as transfection, electroporation, injection etc. Cells lacking an intact Nuk gene may then be identified, for example by Southern blotting, Northern Blotting or by assaying for expression of Nuk protein using the methods described herein. Such cells may then be fused to embryonic cells to generate transgenic non-human animals deficient in Nuk. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific nerve cell populations, developmental patterns of axonogenesis, neural tube formation and nerve regeneration and in vivo processes, normally dependent on Nuk expression.

Figure 9A:
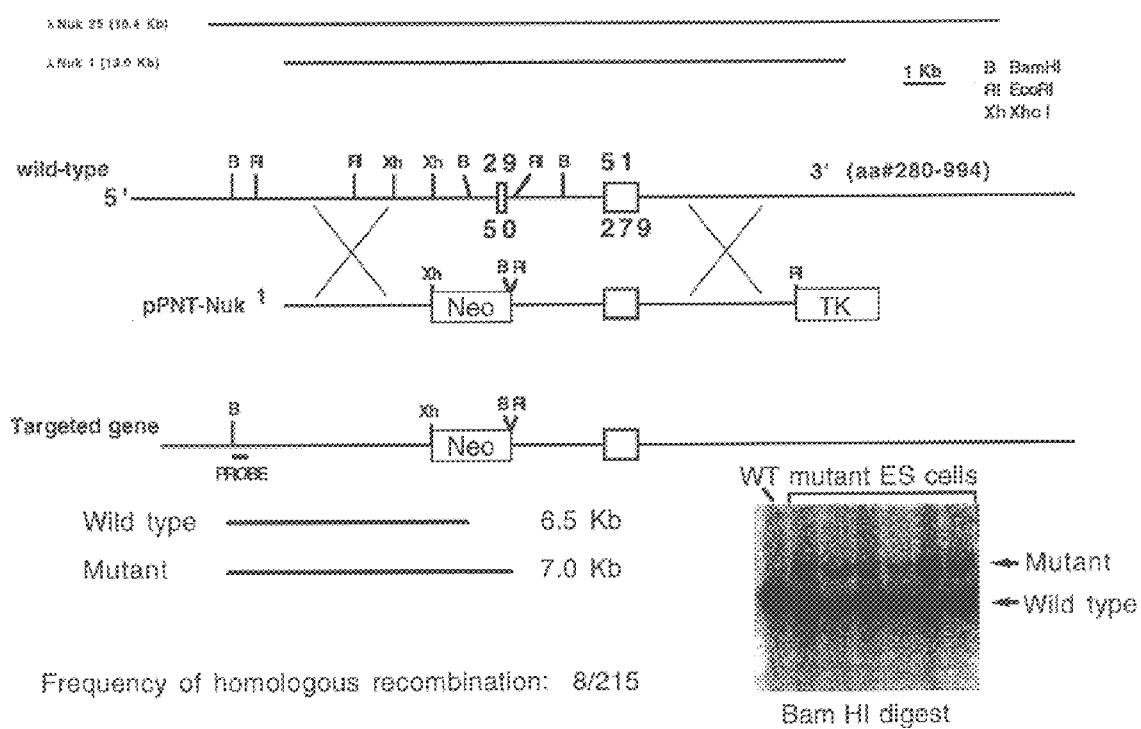
FIG. 9A shows a recombinant DNA molecule of the invention having a null $Nuk^1$ mutation obtained by deletion of exon 2, corresponding to codons 29 to 50 as shown in SEQ ID NO: 1.

The present inventors have generated a loss of function deletion mutation in Nuk, designated Nuk$^1$ in mouse embryonic stem cells, and have achieved germline transmission of this null allele. In particular, the Nuk mutation was obtained by deletion of exon 2, corresponding to codons 29 to 50, as shown in FIG. 9A. Adult animals homozygous for the mutation did not produce any Nuk protein as shown in FIG. 9B. These animals demonstrate the importance of Nuk protein in axonogenesis, and in the formation of the nerve pathways of the central nervous system as the medial tract of the anterior commissure of the brains of the Nuk null mice failed to develop (FIGS. 19A, 19B, 19C and 19D).

Figure 10:
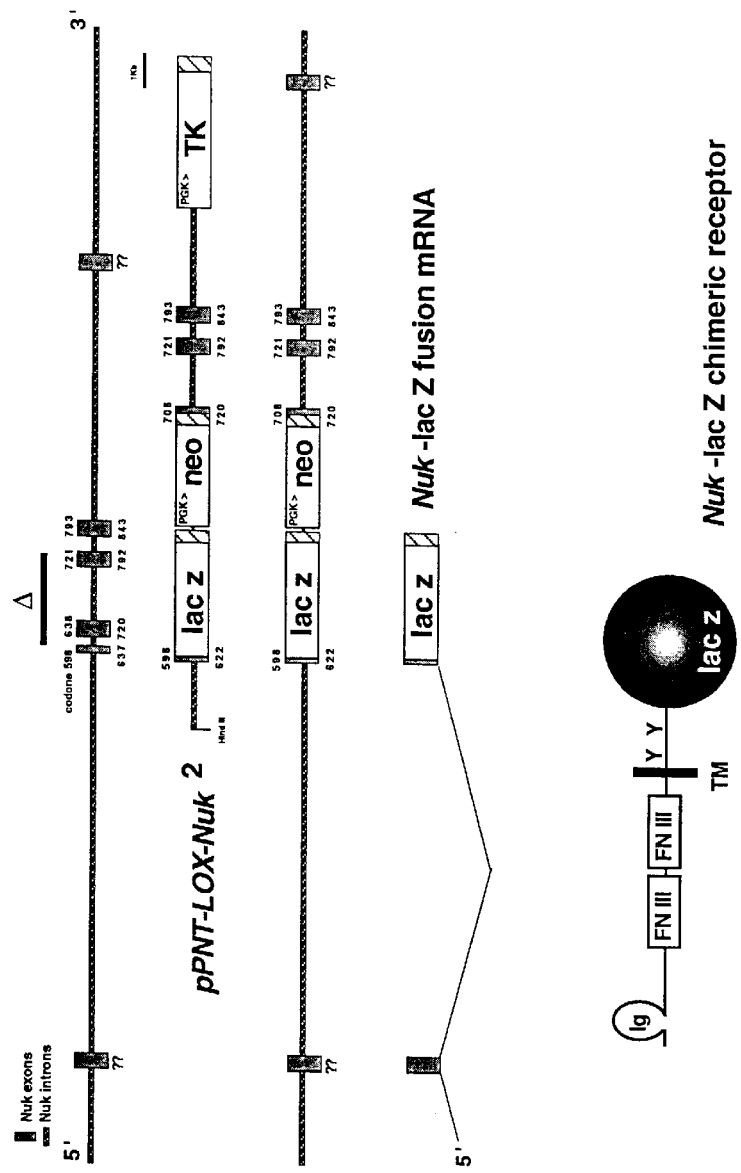
FIG. 10 shows a recombinant DNA molecule of the invention encoding the $Nuk^2$ mutation in the ATP binding region of the kinase domain of Nuk protein, resulting in a Nuk-lac Z chimeric Nuk receptor in which the Nuk tyrosine kinase catalytic domain is replaced by β-galactosidase.

A second targeted mutation, designated Nuk$^2$ was generated in the Nuk gene as shown in FIG. 10 using the pPNT-LOX-Nuk$^2$ gene trap vector to delete the GXGXXG ATP binding region of the kinase domain (amino acids 623–707, SEQ ID NO:2 and FIG. 2) and to create a Nuk-lac Z fusion receptor. Chimeric animals expressing Nuk$^2$ were prepared. Animals generated with the Nuk$^2$ mutation provided Nuk$^2$ expressing cells staining for β-galactosidase activity, providing a convenient marker for Nuk-positive cells in both heterozygous and homozygous backgrounds as detected by a blue/green colour as shown in FIGS. 11 and 12. These animals are useful for studying the expression pattern of Nuk. Nuk$^2$/Nuk$^2$ mice, for example, demonstrate the role of Nuk protein having an extracellular domain, transmembrane domain and juxtamembrane domain, but lacking in a catalytic kinase domain as the medial tract of the anterior commissure developed in these mice, despite the absence of the catalytic kinase domain of Nuk protein. Animals generated with the Nuk$^2$ mutation are useful for studying how the expression pattern of Nuk correlates with observed phenotypic changes which result from mutations in Nuk or in other receptor tyrosine kinases of the Eph subfamily or in substances which bind to such receptors.

The invention also provides methods for preparing cells, tissues, and non-human animals lacking in Nuk expression or partially lacking in Nuk expression, and deficient in the expression of other genes. In accordance with one embodiment, an animal may be generated which is deficient in Nuk and another tyrosine kinase of the Eph/Elk/Eck subfamily. Such animals could be used to determine how the members of the Eph/Elk/Eck subfamily co-operate in embryonic development, particularly development of the nervous system. For example, an animal lacking or partially lacking Nuk expression and Sek-4 expression (Becker N., et al., Mechanisms of Development 47 (1994) 3–17) may be generated to determine how the receptor tyrosine kinases co-operate in the segmental patterning of the hindbrain.

Multiple deficient mice can also be generated to study the interaction of Nuk protein and other proteins such as the Src-family of cytoplasmic tyrosine kinases. For example, an animal may be generated which lacks or partially lacks Nuk expression, and expression of one or more Src family tyrosine kinases including Src, Fyn, and/or Yes.

The following non-limiting examples are illustrative of the present invention:

EXAMPLES

The following materials and methods were utilized in the investigations outlined in the examples:

cDNA Cloning, Sequencing and Chromosomal Mapping

To clone the Nuk coding region, the partial λQ1 Nuk cDNA insert described in Ben-David et al., 1991 (EMBO 10:317) was used to probe a λgt10 cDNA library constructed from 12.5 day mouse embryo mRNA (Logan et al., Dev. Genet. 13:345–358, 1992). Sequence analysis of a number of independent clones revealed that none reached as far as the ATG translation initiation codon. To obtain additional 5' Nuk coding sequences, rapid amplification of cDNA ends (RACE; Frohman et al., Proc. Nat. Acad. Sci. USA 85:8998–9002, 1988) was performed using Nuk-specific oligonucleotides. 9.5 day embryonic poly(A)$^+$ RNA was used for the RACE because Northern blot analysis determined this to be a source of abundant 4.0 and 4.5 Kb Nuk mRNA transcripts. A number of Nuk cDNA clones were generated with this approach, however, a strong stop in the majority of the RACE products just 5' of an NheI restriction site prevented cloning of the complete coding region. One clone out of over 50 examined (pNukRACE 2.15) extended far enough such that an oligonucleotide could be used to colony screen further RACE products. Using this approach two independent clones out of over 1000 screened (pNukRACE A2 and K2) were both found to contain an additional 67 base pairs of Nuk coding sequences 5'of the NheI site. Translation of combined RACE and cDNA clones revealed a single open reading frame of 993 codons. Although lacking an ATG translation initiation codon, the sequence of the RACE clones encode a 26 amino acid hydrophobic signal peptide. The 5'-most sequence of both RACE clones end with the dinucleotide TG. Given that the length of the Nuk signal peptide is longer than most Eph family members, this TG may represent the last two nucleotides of the ATG initiator codon.

The DNAs generated in this study were subcloned into either the pGEM7 (Promega) or pCRII (Invitrogen) plasmid vectors prior to double stranded sequencing using the Sequenase system (United States Biochemical Corporation). Sequencing reactions were primed using either the standard forward and reverse primers or custom oligonucleotides synthesized in house on a Pharmacia Gene Assembler Plus.

Chromosome mapping was performed by probing Pst I restriction endonulcease digested DNAs from 28 different recombinant inbred mouse strains at high stringency with a 1.0 Kb EcoRI fragment of the λQ1 Nuk cDNA.

Generation of Antibodies

A trpE-Nuk fusion protein was created by subcloning a NcoI-BamHI fragment of λQ1 containing the carboxy terminal 94 Nuk codons plus 170 additional nucleotides of 3' untranslated sequences into the bacterial expression vector pATH1. A GST-Nuk fusion protein containing Nuk amino acids 601–994 was also expressed in bacteria. The trpE-Nuk fusion protein was purified from induced bacterial cultures by SDS-PAGE and used to immunize rabbits. Resulting trpE-Nuk antiserum was affinity-purified by binding to immobilized glutathione agarose purified GST-Nuk.

Immunoprecipitation in Vitro Kinase, and Western Blotting

For biochemical studies, natural matings of CD1 mice were used to obtain embryos at 10.5, 12.5, and 14.5 days development. The embryos were collected and washed twice in phosphate buffer saline (PBS; 150 mM NaCl, 3 mM KCl, 9 mM $Na_2HPO_4.2H_2O$, and 2 mM $KH_2PO_4$) prior to homogenization in PLC-lysis buffer on ice (50 mM Hepes, pH 7.5, 150 mM NaCl, 10% glycerol, 1% Triton X-100, 1.5 mM $MgCl_2$, 1 mM EGTA, 10 mM NaPPi, 100 mM NaF, 10 µg/ml aprotinin and leupeptin, 1 mM $Na_3VO_4$, and 1 mM PMSF). The embryo lysates were clarified by centrifugation at 12,000×rpm for 10 min at 4° C. The cleared supernatant was put on ice and an aliquot was used for protein assay (BCA protein assay, PIERCE). For immunoprecipitations, lmg of total protein in 1 ml PLC-lysis buffer were incubated with approximately 4 mg of affinity-purified anti-Nuk antibody and 100 ml of a 10% solution of protein A-sepharose beads. Preimmune serum, as well as preincubation of the anti-Nuk antibodies with a competing trpE-Nuk peptide, were used as controls in the immunoprecipitations. After 1 hour incubation at 4° C., the immunoprecipitates were collected by centrifugation at 12,000×rpm for 30 sec and washed three times with ice cold HNTG buffer (20 mM Hepes, pH 7.5, 150 mM NaCl, 0.1% Triton X-100, 10% glycerol, and 1 mM $Na_3VO_4$).

For in vitro kinase assays, the washed immunoprecipitates were incubated at room temperature (RT) for 15 minutes in 20 ml of kinase buffer (20 mM HEPES, pH7.5, 25 mM $MgCl_2$, 4 mM $MnCl_2$, and 0.1 mM $Na_3VO_4$) containing 10 µCi of $\gamma^{32}$P-ATP (Dupont; 3000 Ci/m mole$^{-1}$). The immune complex kinase reaction products were denatured at 100° C. for 5 min in SDS sample buffer and separated by SDS-polyacrylamide gel electrophoresis. Gels were fixed in acetic acid, submerged in 1 M KOH at 55° C. for 45 min to remove phosphoserine and phosphothreonine, refixed, dried, and then exposed to Kodak XAR film.

For Western blotting, the washed immunoprecipitates were separated by SDS-polyacrylamide gel electrophoresis and electro-transferred to a nylon filter using a semi-dry protein blotting apparatus. The filter was blocked overnight at 4° C. in PBS containing 5% dry milk prior to incubation in the same solution containing 1 µg/ml anti-Nuk antibodies for lhr at room temperature (RT). The filter was washed at RT 3×10 min with TBSN (20 mM TrisHCl, pH 7.5, 150 mM NaCl, and 0.05% NP-40). Nuk immunoreactivity was detected by using affinity-purified goat anti-rabbit horseradish peroxidase (BioRad, 1:20,000 dilution) and Enhanced Chemi-Luminescence reagents (Amersham). The filters were exposed at RT to Kodak XRP-5 film for 30 sec to 5 min.

Whole-Mount Immunohistochemistry

The immunohistochemical detection used in this study was based on the Vectastain ABC Elite-peroxidase system and Vectastain biotin/avidin blocking reagents (Vector Laboratories). The specificity of the anti-Nuk antibody staining was confirmed by a variety of control experiments including those in which the primary antibody was either omitted or preabsorbed with a trpE-Nuk peptide. In addition, other antibodies including a monoclonal antibody raised against the 160 kD subunit of Neurofilament (anti-NF; AMAC Inc.) and a rabbit polyclonal antibody raised against the murine Engrailed (En) proteins were used to control for the specificity of the immunohistochemistry. All observations reported here have been derived from a number of independent experiments all of which gave similar results. The total number of anti-Nuk stained embryos observed at each stage was from 40 to over 100.

Embryos used in this study were obtained from natural matings of CD1 mice and at the required stages of development were dissected and membranes were removed in ice cold 0.1 M phosphate buffer (pH 7.4). Embryos were then fixed with occasional mixing for 2 h on ice in fresh 4% paraformaldhyde in 0.1 M phosphate buffer. In some instances 0.2 to 1% glutaraldhyde was also added to the fixative. The fixative was washed out overnight in 0.1 M phosphate buffer at 4° C. prior to gently dehydrating the embryos in a methanol/phosphate buffered saline (PBS) series (15%/85%; 30/70; 50/50; 75/25% $H_2O$; 100% methanol) on ice for 30 minutes each step. Once in 100% methanol the embryos can be stored at −20° C. for at least 2 months. Prior to rehydration and further manipulation, the embryos were transferred into 80% methanol/20% $H_2O_2$ for 4–6 h at RT to bleach embryos and inactivate endogenous peroxidases. After washing in 100% methanol, the embryos were rehydrated on ice for 30 minutes each with occasional mixing in 75% methanol/25% $H_2O$, 50% methanol/50% PBS, 30% methanol/70% PBS, 15% methanol/85% PBS, and 100% PBS+0.01% Triton X-100. The embryos were then gently mixed on a Nutator at RT 2×1 h in PBSMT (2% Dry Milk Powder, 0.01% Triton X-100 in PBS). At this step a small number of embryos were placed at 4° C. in PBSMT for preabsorbtion of the biotinylated secondary antibodies as described by the manufacturer (Vector Laboratories). The embryos were then blocked overnight at 4° C. on Nutator using the Vectastain ABC Elite and blocking kits in PBSMT+3% normal goat serum (NGS)+10% avidin blocking reagent. The avidin was then washed out in PBSMT 4×1 hour at 4° C. followed by 2×1 hour at RT. The blocked embryos were then incubated on a Nutator for at least 16 h at 4° C. with affinity-purified anti-Nuk antibodies (0.5 to 1.0 mg/ml) in PBSMT containing 3% normal goat serum and 10% biotin blocking agent. Unbound primary antibodies and biotin were washed out in PBSMT 4×1 hour at 4° C. followed by 2×1 hour at RT. The preabsorbed biotinylated secondary antibodies were then added to the embryos and incubation was carried out overnight at 4° C. on a Nutator. The secondary antibodies were washed out as described above and the Vectastain ABC elite avidin-biotin-HRP reagent in PBSMT+3% NGS was added and allowed to incubate overnight at 4° C. on a Nutator. The ABC elite avidin-biotin-HRP reagent was washed out as described above ending with a final wash in PBT (0.2% BSA, 0.01% Triton X-100 in PBS) at RT. For HRP detection, embryos were incubated in 0.3 mg/ml diaminobenzidine (DAB) in PBT at RT for at least 20 minutes. $H_2O_2$ was added to 0.03% and the embryos were incubated at RT under a dissecting microscope until color density was sufficient, usually about 1–10 minutes. The color of HRP-DAB reaction product can be changed from an orange to dark purple color by the addition of $NiCl_2$ to 0.5%. After staining, embryos were washed in PBT and dehydrated through a ethanol/PBS series: 30/70, 50/50, 80/20, 100% ethanol for 30 minutes each. For light microscopy, embryos were cleared in benzyl alcohol:benzyl benzoate (1:2). Photography was carried out with either a Wild M10 macroscope, or a Leitz DMRXE compound microscope using Kodak EPY 64 Tungsten slide film or Kodak Ektar 100 print film. Whole-mount mRNA in situ were performed as described in Canton & Rossant, (1992) Development: 116, 357–368.

Paraffin Section Immunohistochemistry

For the immunohistochemical staining of sectioned embryos, dissected animals were fixed with occasional mixing for 2 h on ice in 4% paraformaldhyde+1% glutaraldehyde in 0.1 M phosphate buffer. Embryos were then washed in phosphate buffer and dehydrated on ice for 30 minutes each with occasional mixing in 25% ethanol/75% PBS, 50% ethanol/50% PBS, 70% ethanol/30% $H_2O$ prior to storage at 4° C. Before embedding in paraffin, embryos were completely dehydrated in 85% ethanol/15% $H_2O$ and then 100% EtOH. The ethanol was replaced with multiple changes of xylene at RT, and the embryos were then equilibrated to 60° C. The xylene was exchanged with many changes of melted paraffin for 2 to 4 hours at 60° C. prior to embedding. Embryos were sectioned at 4 to 6 μm and placed on slides freshly subbed in 1% aminopropyltriethoxysilane. Sections were placed on a slide dryer for 1 hour, allowed to dry overnight at RT, and then partially melted at 55° C. for 20 min.

The antibody staining was performed exactly as described in the Vectastain ABC Elite instructions. Anti-Nuk antibodies were used at 4 to 8 μg/ml. For Nuk+peptide control 8 μg/ml of trpE-Nuk fusion protein was added to the anti-Nuk antibodies and preincubated for 1 hour before adding to the sections. Anti-NF monoclonal antibodies were used at 4 μg/ml. In some instances, the HRP reaction was carried out in DAB only. These sections were counterstained in hematoxylin prior to mounting with coverslips. In other sections, the HRP reaction was carried out in DAB+$NiCl_2$ to produce a darker higher contrast product for black and white photography. These sections were not counterstained prior to mounting. Photography was performed on a Leitz DMRXE microscope using Kodak EPY 64 tungsten color slide film or Kodak Technical Pan black and white print film.

Transmission Electron Microscopy

Since the HRP-DAB reaction product produced in the immunohistochemical staining is electron dense, the subcellular localization of Nuk protein using transmission electron microscopy (EM) of sectioned anti-Nuk protein whole mount stained embryos was performed. Similar ultrastructural immunoperoxidase localization studies of the mammalian embryonic central nervous system has been performed using antibodies directed against the glial fibrillary acid protein (Levitt et al., 1981) or stains specific for the extracelluar matrix (Nakanishi, 1983). Embryos were fixed in 4% paraformaldehyde+1% glutaraldehyde and then immunoreacted as whole-mounts with anti-Nuk antibodies as described above. The stained embryos were postfixed in $OsO_4$, dehydrated, and embedded in Spurr resin. Ultrathin sections were observed and photographed on a Philips EM430 transmission electron microscope. To render the HRP reaction product more visible, counterstaining of the ultrathin sections with uranyl acetate and lead citrate was omitted. To control for fixing conditions and morphology, similar staged and fixed embryos were postfixed in $OsO_4$ and prepared immediately for EM analysis. Other than a loss of lipids from membranes due to extensive washing, the morphology of the immunoreacted samples was comparable to the controls.

Example 1

Cloning and Chromosomal Location of Nuk

The initial Nuk cDNA clone, designated λQ1, was isolated from an unamplified λgt11 expression library constructed from a mouse erythroleukemia cell line by screening with anti-phosphotyrosine antibodies (Ben-David et al., *EMBO* 10:317–325, 1991). Sequence analysis of this clone indicated it was a partial cDNA whose expected translation product was closely related to members of the Eph family of receptor-like tyrosine kinases. Standard cDNA screening of a 12.5 day mouse embryo cDNA library and rapid amplification of cDNA ends (RACE) from 9.5 day embryo mRNA was used to clone the remainder of the Nuk coding region (except for the A of the presumptive ATG initiation codon) following the methods described above.

FIG. 2 shows that the translation of the combined Nuk RACE and cDNA sequences revealed a single open reading frame of 994 amino acids containing both a hydrophobic signal peptide and transmembrane domain (long underlines, FIG. 2). All the hallmarks of a receptor tyrosine kinase of the Eph family are found in Nuk protein, including 20 cysteine residues whose position is conserved in the extracellular domain of Eph family members (bold type, FIG. 2), an immunoglobulin-like domain near the amino terminus (Ig-like), and two fibronectin type III repeats (FN III; between Nuk amino acids residues 330–420 and 444–534). The Ig-like domain of Nuk contains specific residues ($Cys^{70}$, $Trp^{80}$, $Cys^{115}$) known to be conserved in the Ig superfamily (Williams and Barclay, Ann. Rev. Immunol. 6:381–405, 1988). When compared to the Ig-like domains found in other receptor tyrosine kinases (O'Bryan et al., Mol. Cell. Biol. 11:5016, 1991), the Nuk Ig-like domain was found to contain a number of conserved residues (overlines, FIG. 2). A repeat involving the Nuk Ig-like domain and residues 239 to 268 is apparent (underlines, FIG. 2). Although significantly shorter than a normal Ig domain, residues involved in the Nuk-specific repeat correspond to conserved residues often found in Ig-like domains (residues that are both overlined and underlined in FIG. 2). Following the transmembrane domain, the Nuk cytoplasmic region contains a tyrosine kinase catalytic domain (brackets, FIG. 2) and a carboxy-terminal tail of 106 residues.

The cartoon in FIG. 2 shows the location of the various domains. The carboxy-terminal region used to raise the anti-Nuk antibodies is indicated in FIG. 2.

Following a 26 amino acid hydrophobic signal peptide, the Nuk protein extracelluar domain is composed of an Ig-like domain and two FN III repeats. The Nuk protein extracelluar domain also contains 20 cysteines whose position is conserved in the Eph family (Lhotak et al., Mol. Cell. Biol. 11:2496–2502, 1991). A hydrophobic transmembrane domain divides the Nuk protein into approximately two halves, a 548 amino acid extracelluar region and a 419 amino acid cytoplasmic region which contains a tyrosine kinase catalytic domain.

The Nuk protein sequence was compared to other known members of the Eph family. Nuk was found to be most highly related to the full length amino acid sequence of chicken Cek5 (96% identity; Pasquale, Cell Regulation 2:523–534, 1991) and to short PCR products of mRNA from rats (Tyro 5; Lai and Lemke, Neuron 6:691–704, 1991) and humans (Erk; Chan and Watt, Oncogene 6:1057–1061 1991). The close identity between Nuk and Cek5 suggest they represent the mammalian and avian orthologs of the same progenitor gene. The absence of full length cDNAs for Tyro 5 and Erk precludes the determination of whether these sequences correspond to the same or a closely related but different gene.

The chromosomal location of Nuk was determined by probing for restriction fragment length polymorphisms (RFLPs) in the DNA of a number of recombinant inbred mouse strains derived from matings between AKR/J and DBA/2J mice (B. A. Taylor, personal communication). The Nuk locus mapped to the distal end of mouse chromosome 4 near the ahd-1 mutation.

Example 2
Nuk Tyrosine Kinase Activity in Mouse Embryos

To investigate the biological function of Nuk protein, antibodies were raised against a bacterial fusion protein containing the C-terminal 94 amino acids of Nuk (trpE-Nuk). Anti-Nuk protein antibodies were affinity-purified by binding to a bacterial GST-Nuk fusion protein. The specificity of the anti-Nuk protein antibodies was assayed by immunoblotting of bacterial lysates expressing either βgal-Nuk or βgal-Elk carboxy-terminal domains. This experiment demonstrated that the anti-Nuk protein antibodies recognized only the β-gal-Nuk fusion protein. To confirm this result with mammalian protein extracts, Elk protein was immunoprecipitated from a rat brain protein lysate with anti-Elk antibodies. Western blot analysis of the immune-complexes verified that anti-Elk, but not anti-Nuk antibodies could recognize Elk. These experiments demonstrated that the affinity-purified anti-Nuk protein antibodies do not cross-react with the related Elk protein.

To assay for Nuk tyrosine kinase activity in vitro, Nuk protein was immunoprecipitated from 10.5, 12.5, and 14.5 day mouse embryo protein lysates and then incubated in the presence of $[\gamma^{32}P]ATP$. The expression and tyrosine kinase activity of Nuk in the embryos is shown in FIG. 3.

Anti-Nuk protein antibodies immunoprecipitated a protein-tyrosine kinase of 135 kD, as shown in FIG. 3A. A highly phosphorylated protein with a relative mobility of 135 kD was detected in protein extracts of 10.5 day (lane 3, FIG. 3A), 12.5 day (lane 4, FIG. 3A), and 14.5 day (lane 5, FIG. 3A) embryos. The mobility of this protein is consistent with that reported for other Eph family members including Eck, Elk, and Cek5 (Lindberg et al., Mol. Cell. Biol. 10:6316–6324, 1990; Lhotak et al., Mol. Cell. Biol. 11:2496–2502, 1991; Pasquale et al., J. Neurosci. 12:3956–3967, 1992). No kinase signal was observed from 10.5 day embryo lysates when preimmune serum was used (lane 1, FIG. 3A) or if the anti-Nuk antibodies were initially preincubated with a trpE-Nuk fusion protein (lane 2, FIG. 3A). To enrich for phosphotyrosine, the gel was treated with KOH as described previously herein.

Similar anti-Nuk protein immunoprecipitates were also subjected to Western blot analysis with anti-Nuk antibodies, as shown in FIG. 3B. Immunoblotting identified Nuk protein as a 135 kD protein, (FIG. 3B). The anti-Nuk protein antibodies detected Nuk protein as a 135 kD protein in 10.5 day (lane 3, FIG. 3B), 12.5 day (lane 4, FIG. 3B), and 14.5 day (lane 5, FIG. 3B) embryos. No signal was detected if the 10.5 day embryo lysate was immunoprecipitated with pre-immune serum (lane 1, FIG. 3B), or with anti-Nuk antibodies pre-incubated with a trpE-Nuk fusion protein (lane 2, FIG. 3B). The abundant low molecular weight signals are due to binding by the goat anti-rabbit secondary antibodies to the anti-Nuk protein antibodies and the IgG in the preimmune serum used in the immunoprecipitation. In agreement with the in vitro kinase studies, the Western blot revealed highest levels of the 135 kd Nuk protein in 10.5 day mouse embryos (FIG. 3B, lane 3).

Example 3
Segmental Expression of Nuk

The biochemical data presented above and Northern mRNA analysis indicated Nuk is highly expressed in 9.5 to 10.5 day mouse embryos. To investigate this expression in detail, Nuk protein was visualized in 7.5 to 13 day mouse embryos in situ using the anti-Nuk protein antibodies in whole-mount and paraffin section immuno-histochemical techniques. To confirm the protein studies, Nuk mRNA in situs on whole-mounts (Conlon and Rossant, Development 116:357–368, 1992) and frozen sections were also performed with similar staged embryos.

Nuk protein localization in whole-mount and paraffin sections of 7.5 to 10.5 day mouse embryos is shown in FIG.

Figure 4:
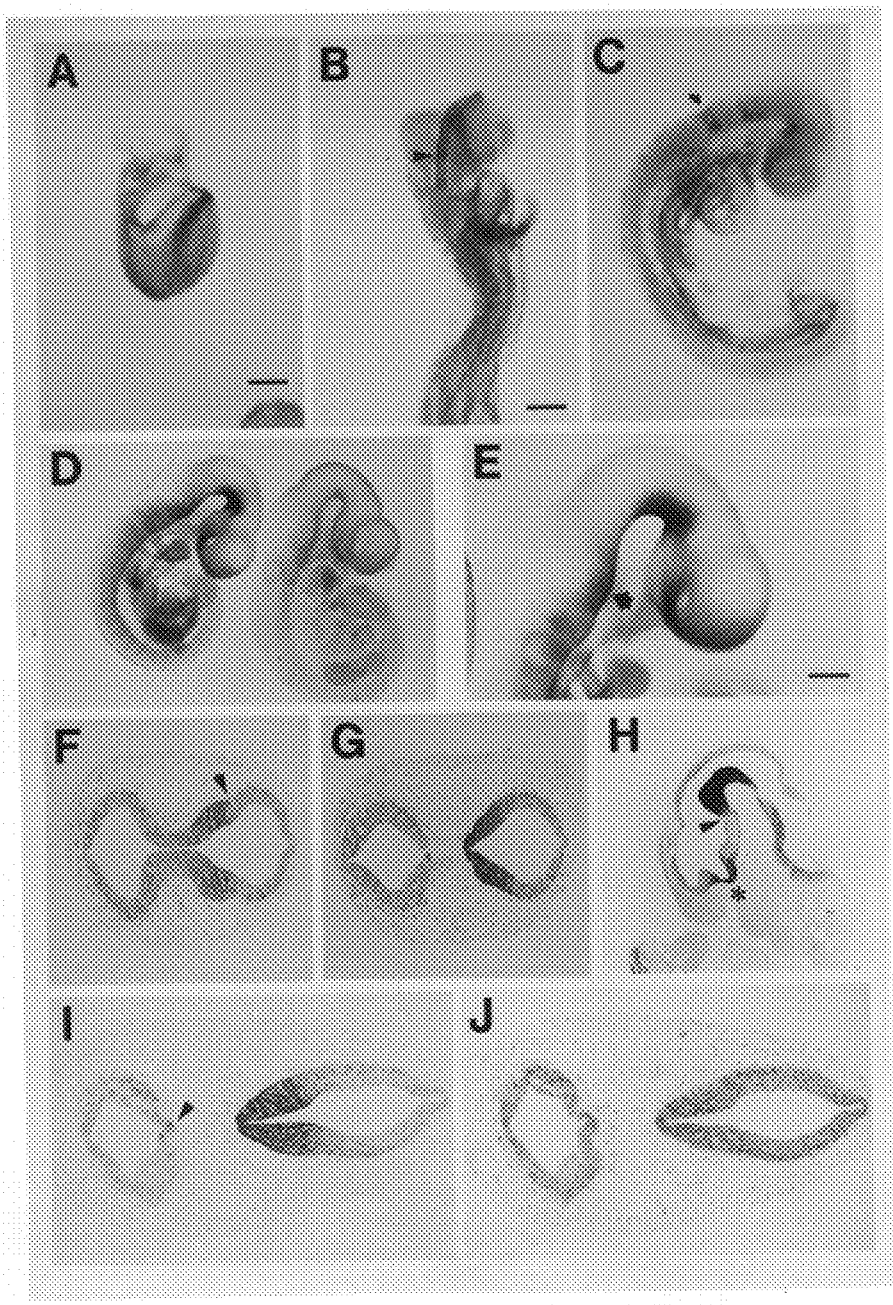
FIG. 4A shows localization of mRNA of the novel receptor tyrosine kinase protein of the invention in whole-mount sections of 7.5 day old mouse embryo.
FIG. 4B shows localization of the novel receptor tyrosine kinase protein of the invention in whole-mount sections of 8 day old mouse embryo.
FIG. 4C shows localization of the novel receptor tyrosine kinase protein of the invention in whole-mount sections of 8.75 day old mouse embryo.
FIG. 4D shows localization of the novel receptor tyrosine kinase protein of the invention in whole-mount sections of 9.5 day old mouse embryo.
FIG. 4E shows localization of the novel receptor tyrosine kinase protein of the invention in whole-mount sections of 9.5 day old mouse embryo in greater detail than in FIG. 4D.
FIG. 4F shows localization of the novel receptor tyrosine kinase protein of the invention in paraffin serial transverse sections of 9.5 day old mouse embryo.
FIG. 4G shows localization of the novel receptor tyrosine kinase protein of the invention in paraffin serial transverse sections of 9.5 day old mouse embryo.
FIG. 4H shows localization of the novel receptor tyrosine kinase protein of the invention in paraffin sagittal section along the midline of 10.5 day old mouse embryo.
FIG. 4I shows localization of the novel receptor tyrosine kinase protein of the invention in paraffin adjacent transverse sections of 10.5 day old mouse embryo immunoreacted with anti-Nuk protein antibodies.
FIG. 4J shows localization of the novel receptor tyrosine kinase protein of the invention in paraffin adjacent transverse sections of 10.5 day old mouse embryo immunoreacted with a trpE-Nuk peptide.

4, comprising whole-mount preparations showing Nuk mRNA (FIG. 4A) and protein (FIGS. 4B to 4E) at early postimplantation stages of embryonic development. Unless otherwise stated, in FIG. 4, dorsal is left and anterior is up. FIG. 4A represents whole-mount mRNA studies which detected Nuk transcripts enriched in the neural ectoderm of an embryo at 7.5 days development (note dorsal surface is up). By the 6 somite stage (8 days) Nuk protein is detected as dark orange horseradishperoxidase (HRP) staining as shown in FIG. 4B. This is most apparent in the neural groove where relatively high levels are observed in specific hindbrain rhombomeres and in the midbrain region. The arrowhead in FIG. 4B points to rhombomeres r2, r3 that express high levels of Nuk protein. The sinus venosis of the developing circulatory system also stains positive for Nuk. FIG. 4C shows an embryo at 12 somite stage (8.75 days) and reveals elevated levels of Nuk protein in specific regions of the anterior neural tube. The most anterior structures immunoreactive for Nuk include the ventral diencephalon followed by the ventral mesencephalon/midbrain. Rhombomeres r2, r3, and r5 of the hindbrain are also immunoreactive for Nuk protein. The arrow in FIG. 4C points to rhombomere 5. The expression of Nuk was confirmed by performing mRNA in situ on similar staged embryos.

FIG. 4D shows 24 somite (9.5 day) stage embryos immunoreacted with either anti-Nuk protein antibodies (left) or, as a control, anti-Nuk protein antibodies that were preincubated with a trpE-Nuk fusion protein (right). Nuk protein is most abundant in the ventral midbrain, diencephalon, and optic stalk. Along the spinal cord, high levels of Nuk protein is detected at the dorsal surface of the neural tube (see FIG. 5 for more detail). Note the absence of specific staining in the control embryo. FIG. 4E shows whole-mount immunolocalization of Nuk protein in the developing brain of a 9.5 day embryo in greater detail. Nuk protein is most highly expressed in the ventral midbrain encompassing the flexure region. Nuk protein is also detected in the ventral diencephalon, optic chiasm, optic stalk, retinal cells (out of focus), and basal telencephalon. At this stage, Nuk protein is still detected in the hindbrain and is localized to the floorplate (arrow in FIG. 4E points to ventral region of rhombomere 2). Note the small patch of Nuk protein now detectable in the lateral region of rhombomere 4 just anterior of the otic vesicle.

FIGS. 4F to 4J show immunohistochemical detection of Nuk protein in paraffin sections of 9.5 and 10.5 day mouse embryos. FIGS. 4F and 4G show serial transverse sections of a 9.5 day embryo immunoreacted with anti-Nuk antibodies which detect Nuk protein (brown stain) in the ventral midbrain. Nuk protein is localized to all layers of the neural tube including the proliferative ventricular zone, the internal mantel layer, and the outer marginal layer which is adjacent to the surrounding mesenchyme. Note Nuk protein is detected only in the ventral aspect of the midbrain and its limit of expression marks a specific morphological bulge/constriction of the neural tube that separates ventral from dorsal components (arrowhead).

FIG. 4H shows a sagittal section along the midline of a 10.5 day embryo showing Nuk protein (dark stain) concentrated in ventral regions of the midbrain and in the optic chiasm (asterisk) and footplate of the hindbrain (thick arrow). The orientation of this embryo is opposite to the one shown in FIG. 4E. Note the appearance of a morphological constriction (arrowhead) which separates the midbrain from the diencephalon. Since this is a section along the midline, the infundibulium or ventral most region of the diencephalon is exposed between the midbrain and optic chiasm. This region of the diencephalon does not express Nuk. FIGS. 4I and 4J show adjacent transverse sections of a 10.5 day embryo immunoreacted with either anti-Nuk protein antibodies (4I) or anti-Nuk antibodies preincubated with a trpE-Nuk peptide (4j), and illustrate the specificity of the immunohistochemistry. Staining of Nuk protein at 10.5 days persists in the ventral midbrain and is also detected at lower levels in the floorplate of the hindbrain (arrowhead).

The scale bars shown in FIG. 4 represent the following measurements: (4A), 100 μm; (4B and 4C), 120 μm; (4E, 4F, 4G, 4I, 4J), 150 μm; (3H), 300 μm.

As described above, by the six somite stage (8 days) high levels of Nuk protein are detected in the neural ectoderm prior to fusion of the dorsal edges of the neural plate (FIG. 4B). Highest levels of Nuk immunoreactivity are detected in the presumptive midbrain and in specific rhombomere segments of the hindbrain. Nuk protein is also detected in the sinus venosis of the developing circulatory system. By the 12 somite stage (8.75 days) the dorsal edges of the neural plate have fused forming the neural tube. High levels of Nuk protein are localized to specific compartments of the neural tube including hindbrain rhombomeres r2, r3, and r5, the ventral midbrain (mesencephalon) encompassing the flexure, and the ventral diencephalon (FIG. 4C).

By 9.5 to 10.5 days of development, Nuk expression intensifies in specific ventral regions of the developing brain structures (FIGS. 4D and 4E). In the hindbrain at this stage, Nuk protein becomes concentrated along the floor plate. When anti-Nuk protein antibodies are used to stain transverse sections at the midbrain of 9.5 day (FIGS. 4F and 4G) and 10.5 day (FIG. 4I) embryos, it is apparent that Nuk protein is restricted to the morphological bulge corresponding to the ventral/basal plate of the mesencephalon. Preincubating the anti-Nuk protein antibodies with a Nuk peptide abolished the signal, demonstrating the specificity of the antibody in both whole-mount and paraffin section immunohisto-chemistry (FIG. 4D and 4J). Staining of additional transverse sections determined that Nuk protein in the diencephalon of 9 to 10.5 day embryos is also restricted to ventral structures, including the hypothalamus, thalamus, and the optic stalk. Very high levels of Nuk protein were also detected in cells of the primitive optic chiasm at day 10.5. Sagittal sections confirmed that high levels of Nuk mRNA and protein (FIG. 4H) are detected specifically in ventral cells of the developing brain. Consistent with the in vitro kinase and Western analysis, anti-Nuk immunoreactivity in 11.5 to 13.5 day embryos decreases significantly in these brain structures as discussed below.

Example 4

Subcellular Localization of Nuk

The immunohistochemical reaction product observed for the anti-Nuk antibodies often appears as if the Nuk protein is localized to specific surfaces of the plasma membrane. One clear example of this is at the dorsal surface of the posterior neural tube which contains elevated amounts of the Nuk protein as early as 9.5 days of development (see FIG. 4D). The subcellular localization of Nuk protein is shown in more detail in FIG. 5.

Figure 5A:
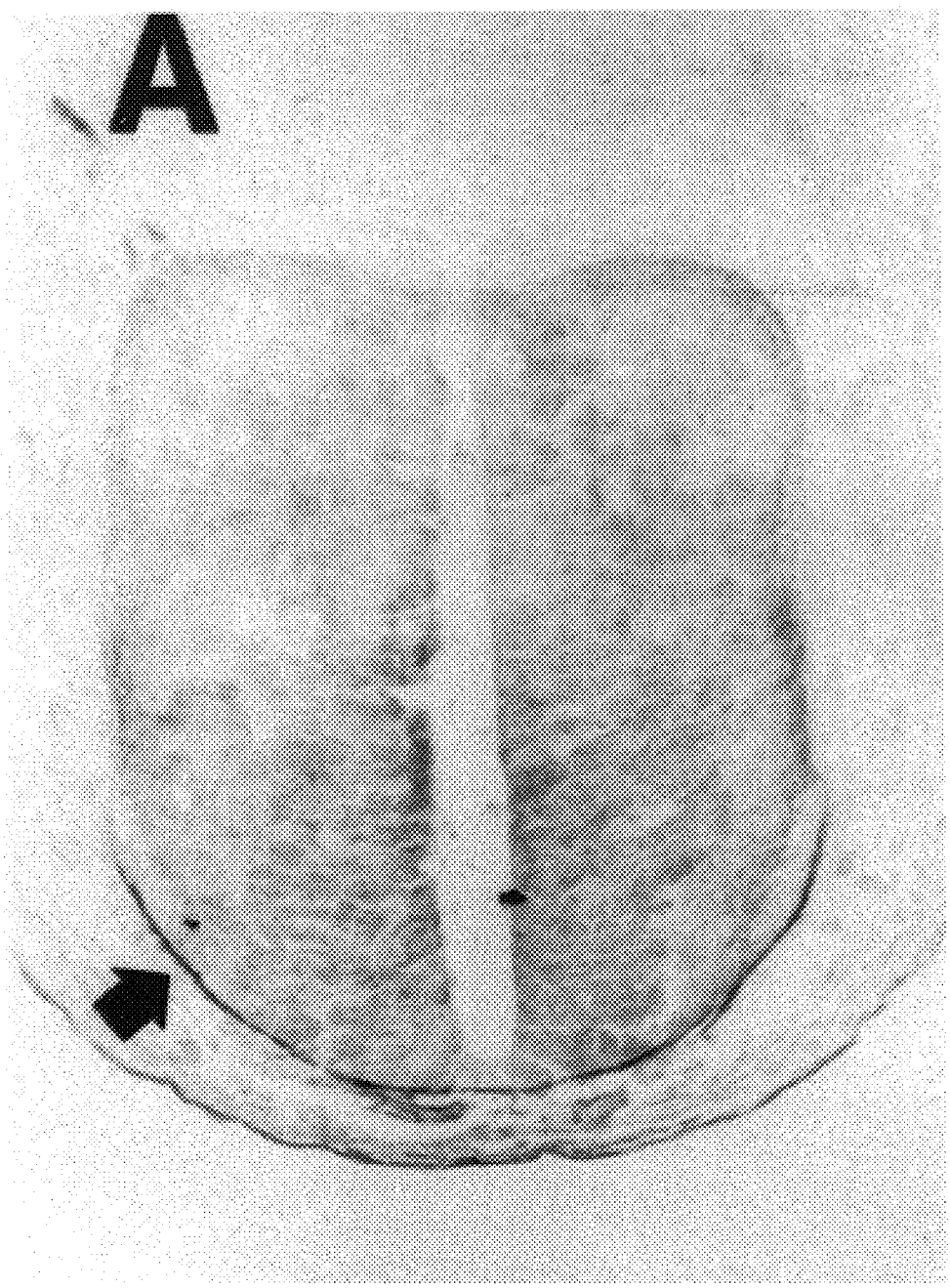
FIG. 5A shows an adjacent transverse section of an 11.5 day embryo at the level of the caudal/posterior spinal cord immunoreacted with anti-Nuk antibodies.
Figure 5B:
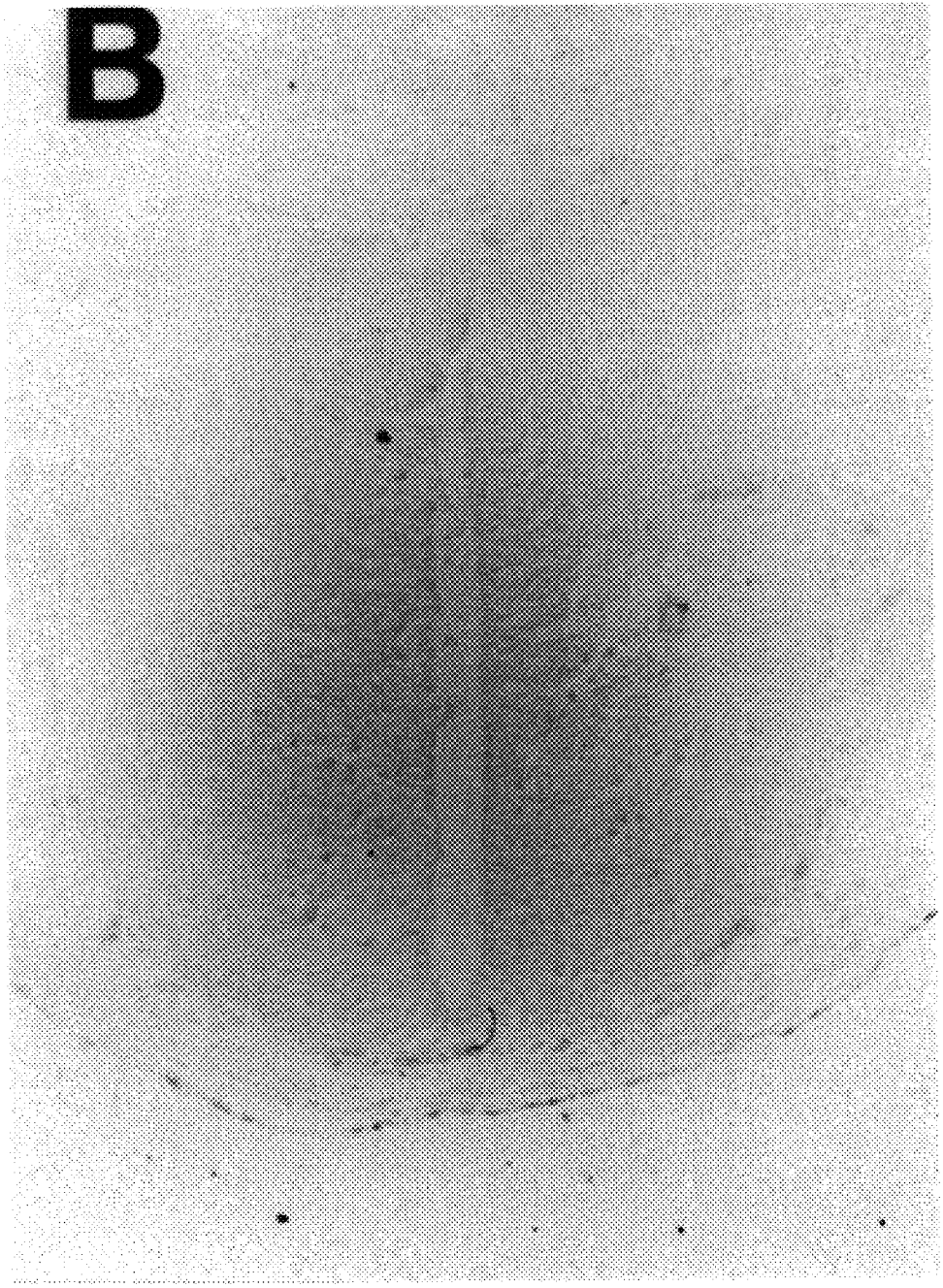
FIG. 5B shows an adjacent transverse section of an 11 day embryo at the level of the caudal/posterior spinal cord immunoreacted with anti-Nuk antibodies preincubated with a trpE-Nuk peptide.

FIGS. 5A and 5B are adjacent transverse sections of an 11.5 day embryo at the level of the caudal/posterior spinal cord immunoreacted with either anti-Nuk antibodies (5A) or anti-Nuk antibodies preincubated with a trpE-Nuk peptide (5B). Nuk protein is concentrated in the dorsal region of the neural tube along the basement membrane (arrow). This localization of Nuk protein is observed as early as 9.5 days of development in whole-mount preparations (see FIG. 4D).

Antibodies to Neurofilament (anti-NF) and Engrailed (anti-En) proteins did not stain the basement membrane demonstrating the specificity of the anti-Nuk antibodies.

Figure 5C:
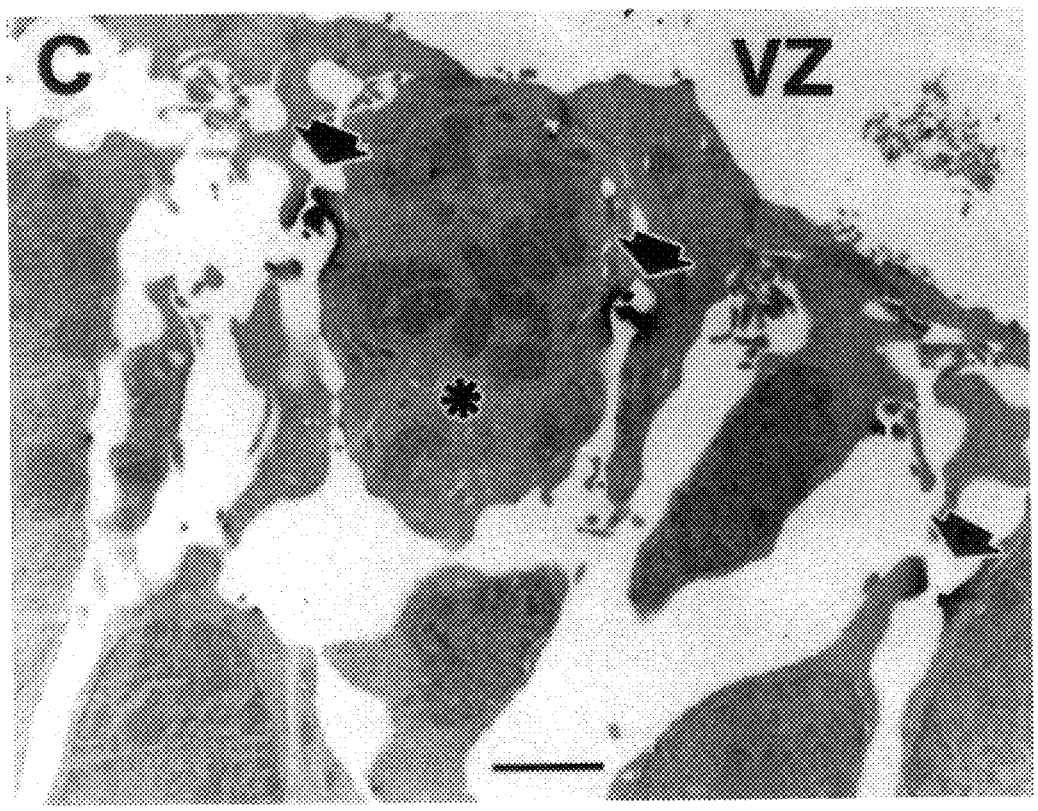
FIG. 5C shows transmission electron microscopy immunolocalization of Nuk protein in ventral midbrain cells of a 9.5 day embryo.
Figure 5D:
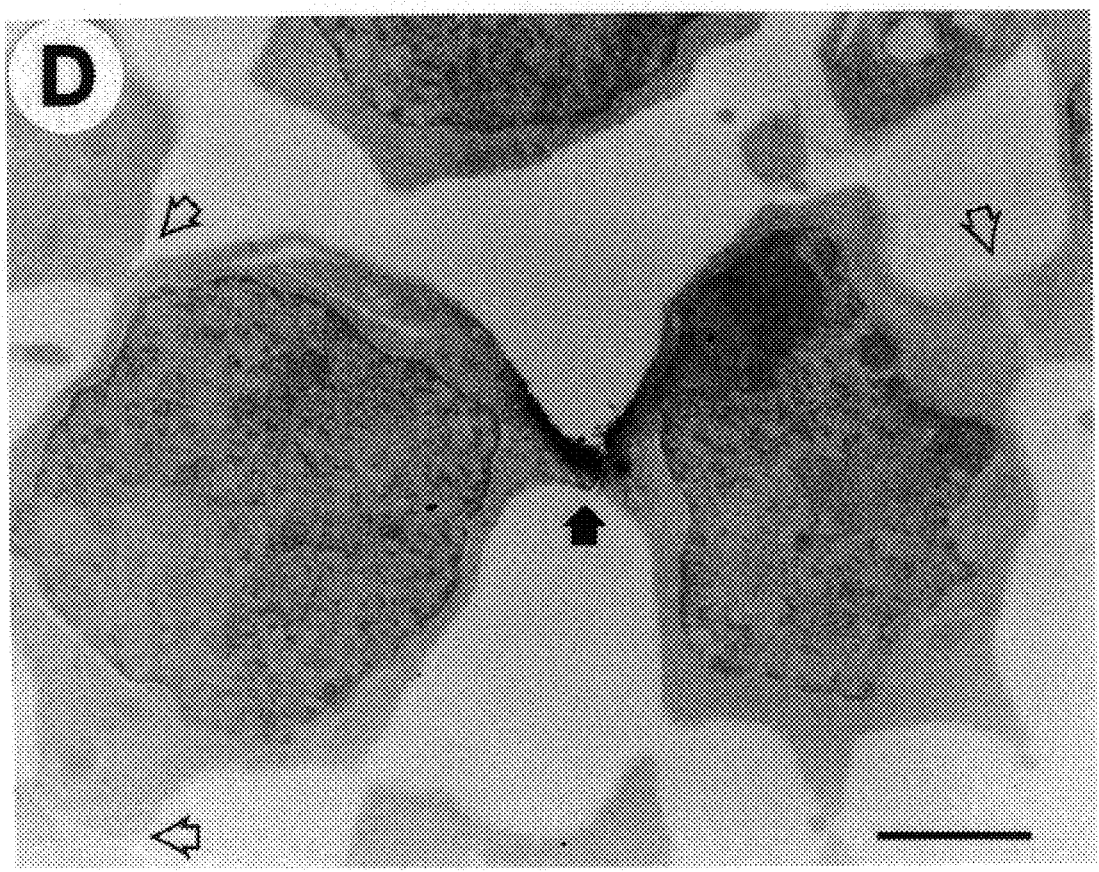
FIG. 5D shows transmission electron microscopy (EM) immunolocalization of Nuk protein in ventral midbrain cells of a 9.5 day embryo.

FIGS. 5C and 5D show transmission electron microscopy (EM) immunolocalization of Nuk protein in ventral midbrain cells of a 9.5 day embryo. Immunoperoxidase anti-Nuk stained whole-mount embryos were ultrathin sectioned and observed under EM. FIG. 5C shows that, at the proliferative ventricular zone (VZ), Nuk-positive signals are concentrated at sites of cell—cell contact (arrows). Notice that Nuk protein immunostaining is often localized on the membranes of both cells that are making contact. At this stage of development there is no obvious ultrastructural differences between neuronal and glial cell types. Therefore, it cannot be distinguished if Nuk protein is associated with neurons, glial, or both cell types. Note the condensed chromatin evident in the nucleus of a cell that is in late prophase (asterisk).

FIG. 5D shows that cells within the postmitotic mantal region of the neural tube also exhibit Nuk protein localization at sites of cell—cell contact. The photomicrograph shows a site of contact between two cells labelled strongly for Nuk protein (filled arrow). Note that other sites of cell—cell contact do not contain detectable amounts of Nuk protein (open arrows).

The scale bars in FIG. 5 represent the following measurements: (A and B) 100 $\mu$m; (C), 2 $\mu$m; (D), 1 $\mu$m.

Transverse sections of 11.5 day embryos shows in greater detail that Nuk protein is concentrated where the dorsal-most membrane of the neural tube make contact with the surrounding mesenchyme/neural crest cells (FIGS. 5A and B). Lateral and ventral regions of the neural tube do not exhibit this localized Nuk protein.

Since the HRP-DAB reaction product produced in the immunohistochemical staining is electron dense, the subcellular localization of Nuk protein was investigated using transmission electron microscopy (EM), following the methods described above. The ventral midbrain of 9.5 day embryos was chosen for EM analysis because of its intense Nuk immunoreactivity. FIG. 5C shows a section of the midbrain at the mitotically active ventricular zone. Nuk immuno-reactivity associated with these cells is usually localized to the plasma membranes at specific sites of cell—cell contact. As shown in FIG. 5D, Nuk immunoreactivity was not found to be localized to all sites of cell—cell contact. In addition, small punctate deposits throughout the ventral midbrain were immunoreactive for Nuk protein. These structures appear to be plasma membrane material lost from post-mitotic cells during their radial migration from the ventricular zone.

Example 5
Nuk Localization in Pioneer Cranial PNS Axons and an Early CNS Axon Tract and in Spinal Axons Axonogenesis in mouse embryos commences at approximately 10 days of development when neurons associated with both the central and peripheral nervous systems extend axon projections toward their targets. Anti-Nuk antibody staining of 10 to 12 day embryos revealed that Nuk protein is highly concentrated within most if not all early axonal projections of the PNS and to at least one early pathway of the CNS.

An example of Nuk protein localization in a specific cranial nerve, the oculomotor nerve (III), is shown in FIG. 6. FIG. 6A is a photomicrograph of the head of an 11 day anti-Nuk whole-mount immunostained embryo with one of the pair of oculomotor nerve fibers in focus showing strong labelling of Nuk protein (filled arrow). A clearer view of Nuk protein staining in the oculomotor axons fibers can be obtained when the whole-mount staged embryo was filleted down the midline to minimize tissue thickness (FIG. 6B). This view shows that the Nuk protein positive oculomotor III axons exit the neural tube from the ventral aspect of the midbrain. An anti-Nuk stained frontal section shows that these axons originate from the Nuk-expressing cells in the ventral midbrain, at a region that is consistent with the position of the oculomotor nuclei (FIG. 6E). Anti-Nuk antibodies also label an early pathway of the CNS (open arrow in FIG. 6).

Figure 6A:
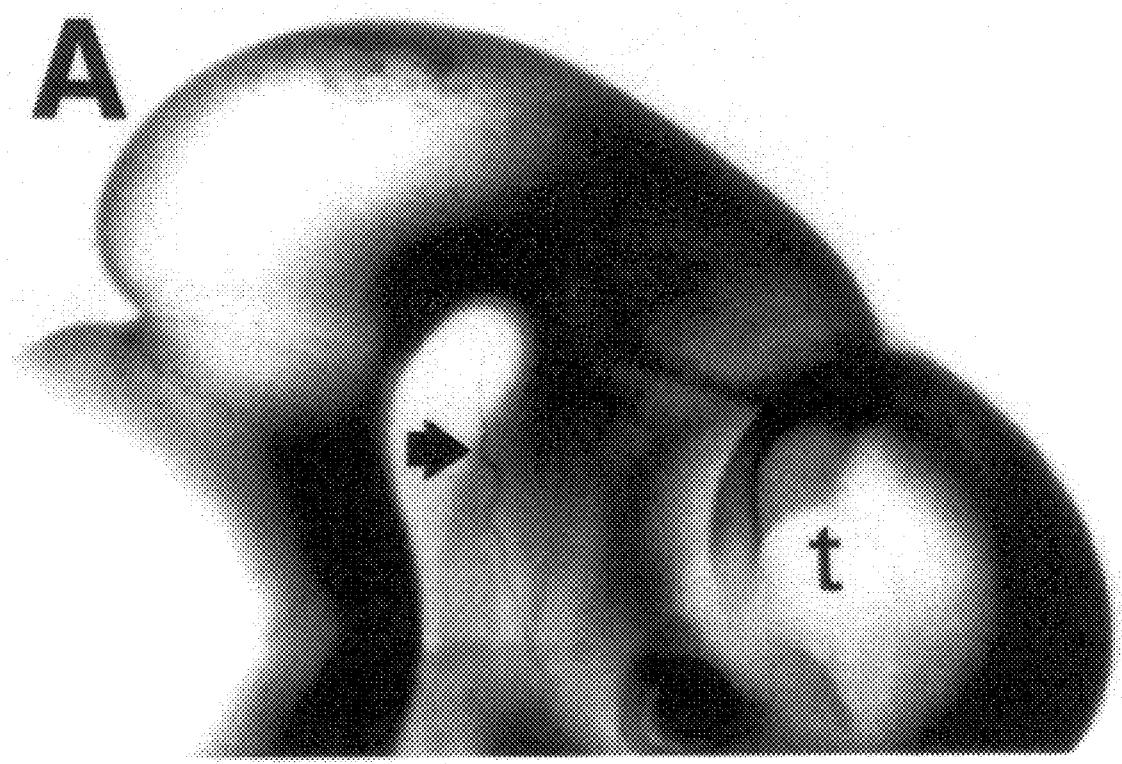
FIG. 6A is a photomicrograph of the head of an 11.5 day anti-Nuk whole-mount immunostained embryo with one of the pair of oculomotor nerve fibers in focus showing strong labelling for Nuk protein (filled arrow)
Figure 6B:
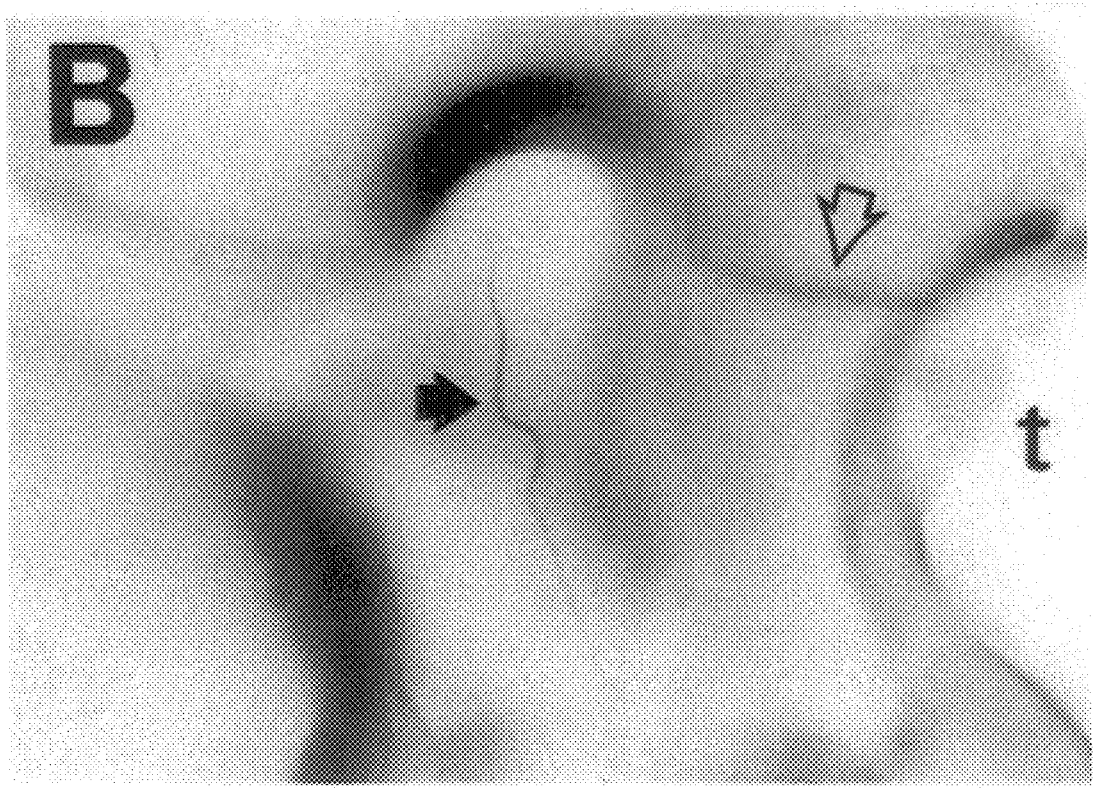
FIG. 6B shows a clearer view of Nuk protein staining in the oculomotor axons fibers obtained when the whole-mount staged embryo was filleted down the midline to minimize tissue thickness.
Figure 6C:
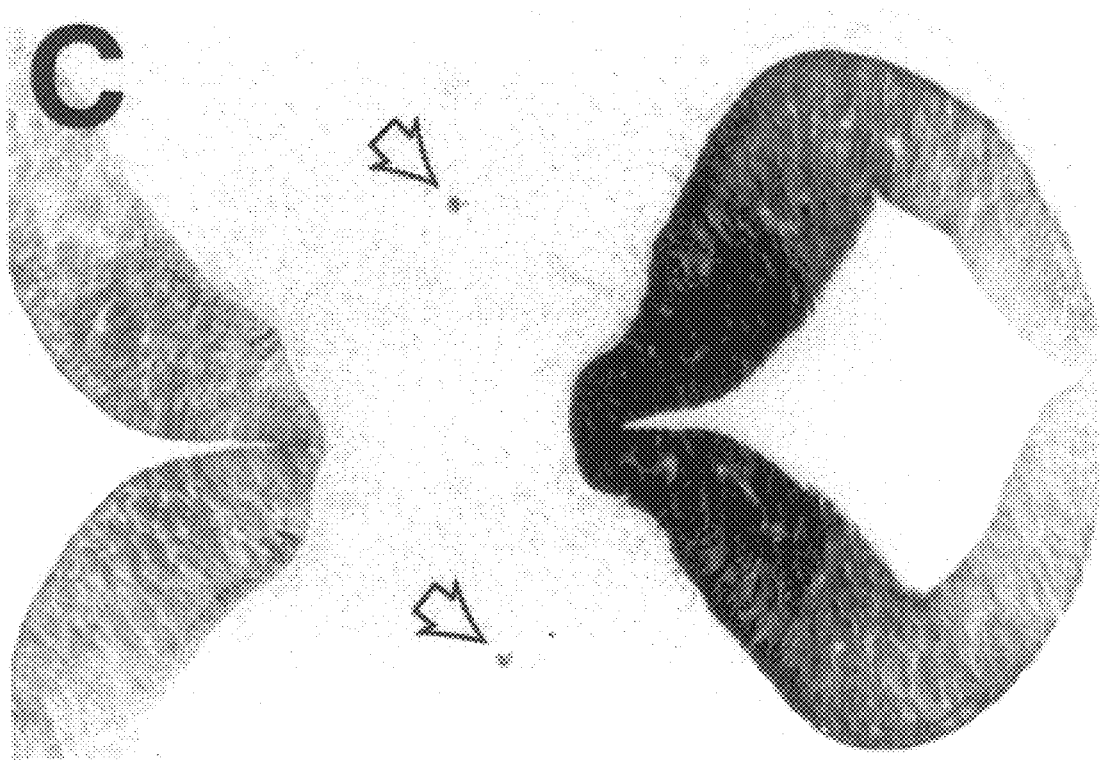
FIG. 6C shows a paraffin section of a 10.5 to 11 day mouse embryo immunostained with anti-Nuk.
Figure 6D:
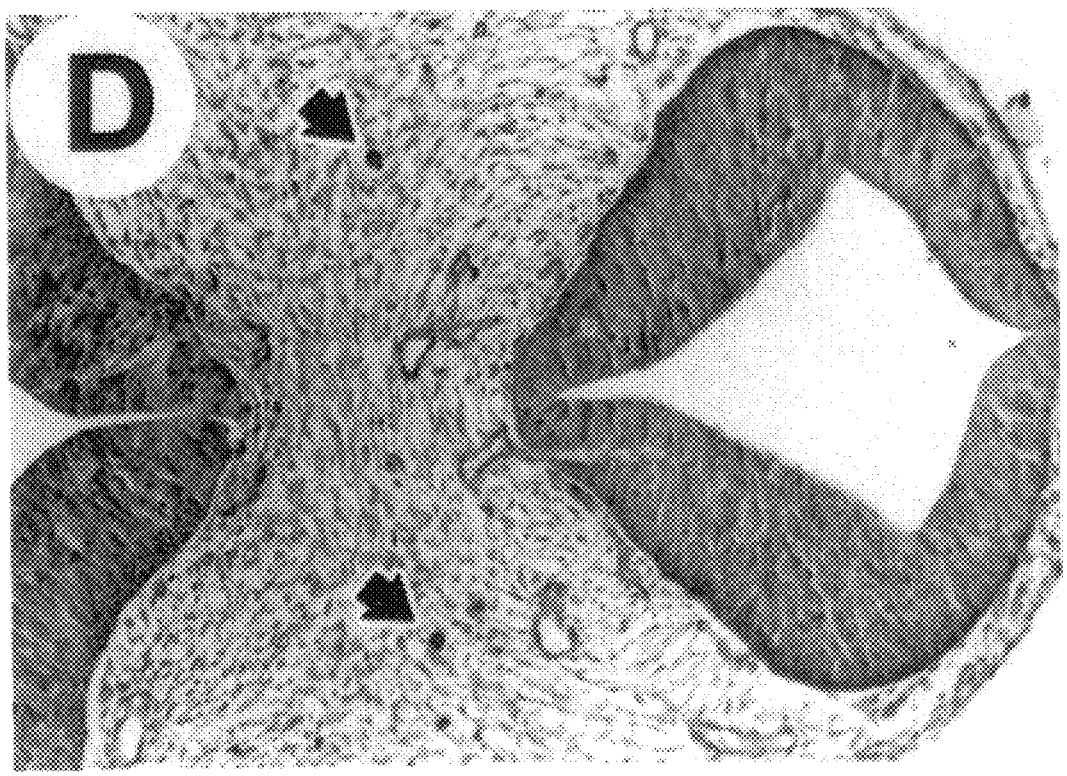
FIG. 6D shows a paraffin section of a 10.5 to 11 day mouse embryo immunostained with anti-Neurofilament antibodies.
Figure 6E:
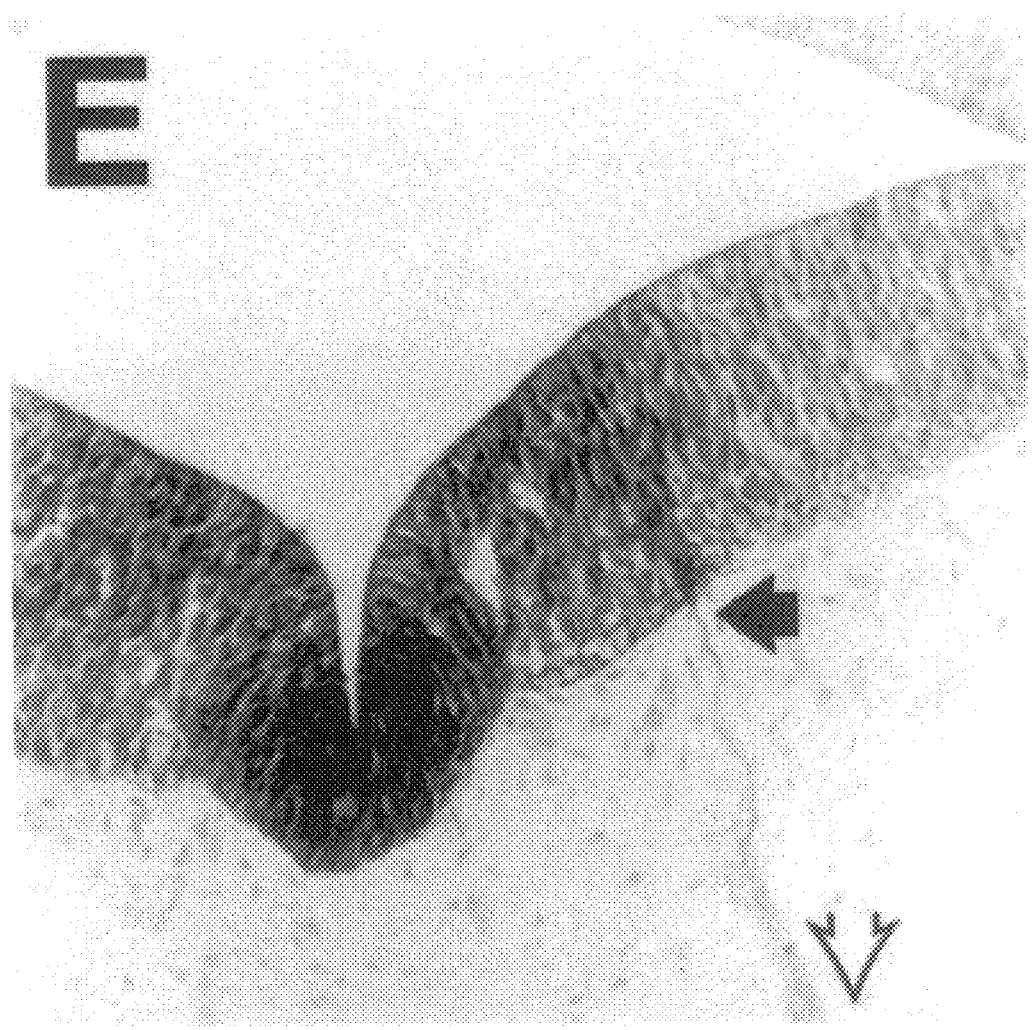
FIG. 6E is a frontal section immunostained with anti-Nuk antibodies which label the ventral midbrain and oculomotor axon fibers as they exit the neural tube (filled arrow) and extend (open arrow) towards their target tissue, the pre-optic muscle mass.

FIGS. 6C to 6F show paraffin section immunohistochemistry of 10.5 to 11 day mouse embryos. Adjacent transverse sections bisecting the pair of oculomotor nerve fibers were immunostained with either anti-Nuk (6C) or anti-Neurofilament (6D) antibodies. The arrows in both FIGS. 6C and 6D point to the darkly stained axon bundles of the two oculomotor nerves. To verify the specificity of the immunohistochemistry, additional control experiments were performed in which the anti-Nuk antibodies were either omitted, preincubated with a trpE-Nuk peptide, or substituted with antibodies directed against the Engrailed (anti-En) nuclear homeodomain proteins. FIG. 6E is a frontal section immunostained with anti-Nuk antibodies which label the ventral midbrain and oculomotor axon fibers as they exit the neural tube (filled arrow) and extend (open arrow) towards their target tissue, the pre-optic muscle mass.

Figure 6F:
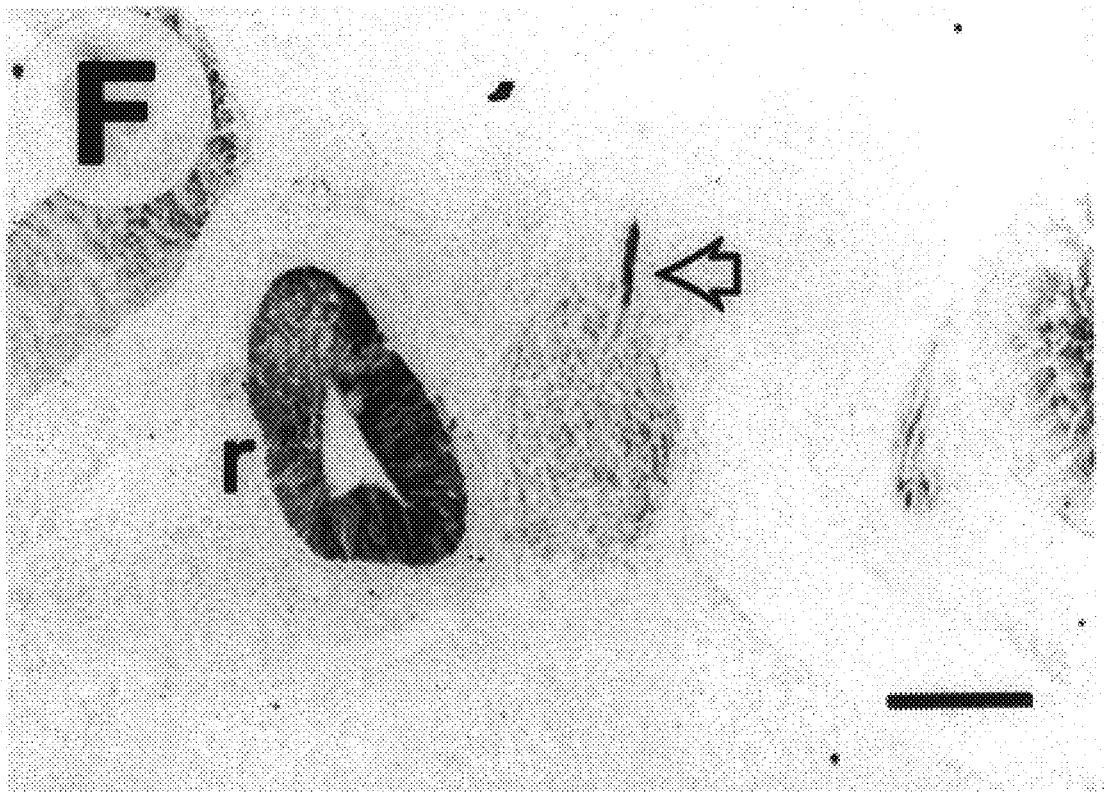
FIG. 6F shows a sagittal section immunostained with anti-Nuk antibodies which label the oculomoter axon fascicule as it enters the pre-optic muscle mass (open arrow)

FIG. 6F shows a sagittal section immunostained with anti-Nuk antibodies which label the oculometer axon fascicule as it enters the pre-optic muscle mass (open arrow). This section also shows the expression of Nuk protein in the developing retinal cells (r). The orientation of this section is the same as FIG. 4H.

The scale bar for FIGS. 6(A) is 180 $\mu$m; (B) 120 $\mu$m; and (C–F) 100 $\mu$m.

To confirm that the observed Nuk protein localization is in axons, adjacent transverse sections that bisect the oculomotor nerve fibers of a 10.5 day embryo were immunoreacted with either anti-Nuk (FIG. 6C) or neuron-specific anti-Neurofilament antibodies (anti-NF; FIG. 6D). Both antibodies labelled the same structure demonstrating the axon-specific localization of Nuk protein. The main target tissue of oculomotor axons is the premuscle mass of cells adjacent to the developing retina, whose function in the adult is to control certain eye movements. An anti-Nuk stained sagittal section labelled the oculomotor axon fascicule at the point of entry into the premuscle mass (FIG. 6F). This section also shows the high level of Nuk protein associated with the developing retinal cells.

Figure 7:
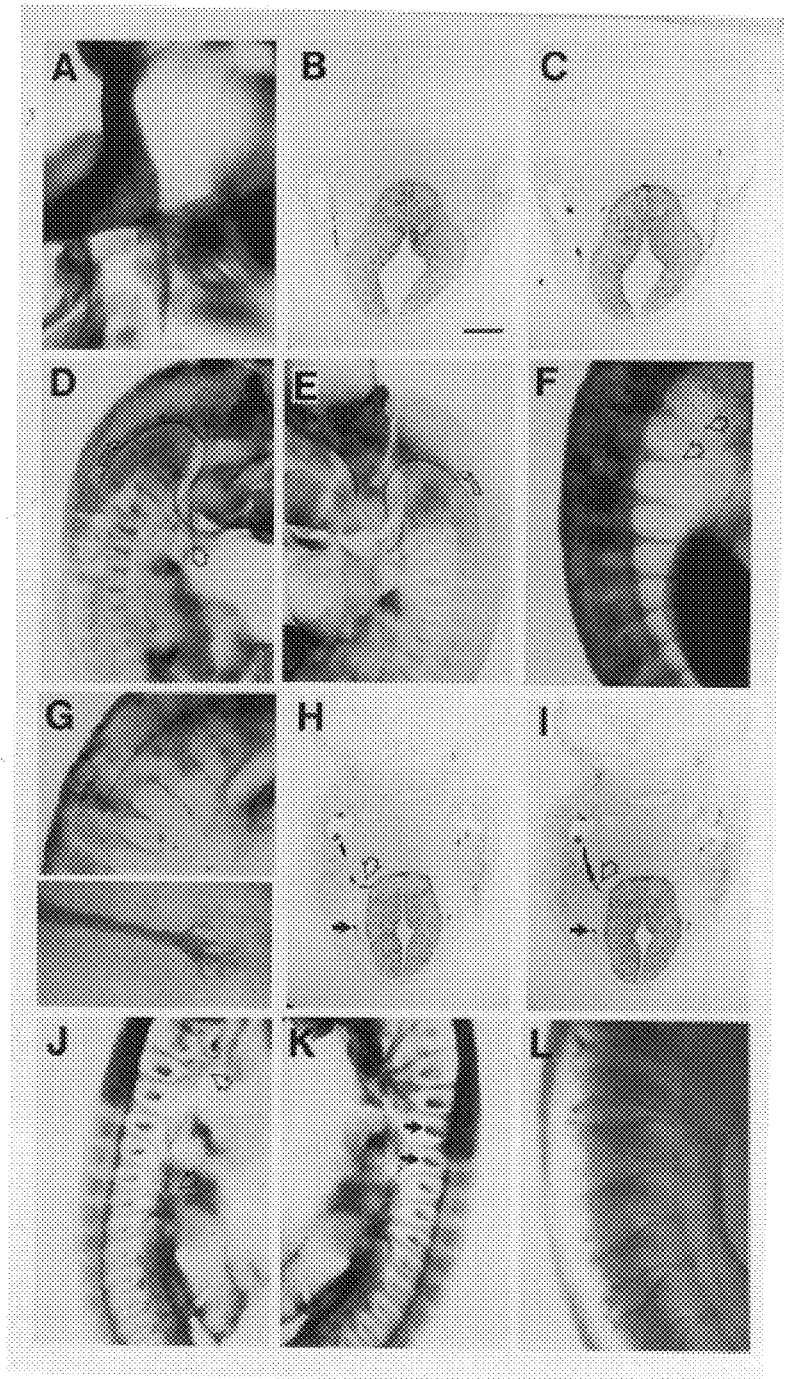
FIG. 7A is a 10.5 day whole-mount embryo immunostained with anti-Nuk antibodies which label the trigeminal nerve V and facial nerve VII.
FIG. 7B shows transverse sections of a 10.5 day embryo showing Nuk-positive trigeminal nerve V axon fascicules labelled with the anti-Nuk antibodies.
FIG. 7C shows transverse sections of a 10.5 day embryo showing Nuk-positive trigeminal nerve V axon fascicules labelled with the anti-Nuk antibodies.
FIG. 7D is an 11.5 day anti-Nuk whole-mount showing localization of Nuk protein in the vagus nerve X associated fibers as they pathfind to their target visceral organs (curved open arrows)
FIG. 7E is an 11.5 day anti-Nuk whole-mount showing localization of Nuk protein in the vagus nerve X associated fibers as they pathfind to their target visceral organs (curved open arrows)
FIG. 7F is a whole-mount 10 day embryo showing Nuk protein concentrated within the earliest spinal nerve fibers exiting the neural tube (arrows)
FIG. 7G shows a slightly later stage embryo from that shown in FIG. 7F.
FIG. 7H shows a transverse section bisecting the rostral spinal cord of an 11 day embryo demonstrating that the darkly stained Nuk-positive fibers shown in FIGS. 7F and 7G are ventral motor axons (open arrows)
FIG. 7I shows a transverse section bisecting the rostral spinal cord of an 11 day embryo demonstrating that the darkly stained Nuk-positive fibers shown in FIGS. 7F and 7G are ventral motor axons (open arrows)
FIG. 7J shows both sides of an 11 day whole-mount embryo demonstrating that Nuk protein is localized within the spinal motor nerves as they elongate to the plexus regions (open arrows)
FIG. 7K shows both sides of an 11 day whole-mount embryo demonstrating that Nuk protein is localized within the spinal motor nerves as they elongate to the plexus regions.
FIG. 7L shows a close-up of a 12 day whole-mount embryo immunostained with anti-Nuk antibodies which label the nerve fibers of the parasympathetic chain ganglion.

Other cranial PNS axons contain high levels of Nuk protein early during their elongation. Nuk protein is detected in the trigeminal (V) and facial (VII) nerve fibers in 10.5 day embryos (FIGS. 7A to 7C). The vagus (X) parasympathetic autonomic nerve, and the accessory (XI) and hypoglossal (XII) somatomotor nerves also contain localized Nuk protein (FIGS. 7D and 7E). As observed by the anti-Nuk labelling, these fibers enter a common region, the cardiac/pulmonary plexus, where they then elongate to their targets such as the cardiac muscle and other visceral organs (vagus) or the upper torso (accessory) and tongue (hypoglossal). Nuk protein localization in these cranial axons is very transient and is not detected after 12.5 days development.

The embryo in FIGS. 6A and B also exhibits specific anti-Nuk labelling in the developing CNS of a connection between the telencephalon and the midbrain. Information describing the naming and position of early tracts in the developing mammalian forebrain is sparce. The location of Nuk immunoreactivity is consistent with the location of axonal projections originating from the ventral midbrain tegmentum such as those of the red nuclei or the reticular activating system (Carpenter, 1985, Core Text on Neuroanatomy, Baltimore: Williams & Wilkins). Alternatively, this pathway may correspond to the telencephalic/supraoptic tract described in zebra (Chitnis and Kuwanda, J. Neurosci. 10, 1892–1905, 1990; Wilson et al., (1990) Development, 108, 121–143, 1990). Closer definition of the origin and termination sites as well double labelling with other antibody probes should help determine the identity of this Nuk-positive tract.

Example 6
Nuk Localization in Spinal Axons

FIGS. 7A to 7E show Nuk protein localization in cranial nerves of 10.5 to 12 day mouse embryos. FIG. 7A is a 10.5 day whole-mount embryo immunostained with anti-Nuk antibodies which label the trigeminal nerve V and facial nerves VII. FIGS. 7B and 7C show transverse sections of a 10.5 day embryo showing Nuk-positive trigeminal nerve V axon fascicules labelled with the anti-Nuk antibodies. Note that Nuk protein is also present throughout the caudal hindbrain region of the neural tube. FIGS. 7D and E are 11.5 day anti-Nuk whole-mounts showing localization of Nuk protein in the vagus nerve (X) associated fibers as they pathfind to their target visceral organs (curved open arrows). Other cranial axons including the accessory (XI) and hypoglossal (XII) nerve fibers are immunoreactive for Nuk protein. These cranial nerves initially extend to the plexus region (open arrow in D) before they pathfind to the heart and other target tissues.

FIGS. 7F to 7L show Nuk protein localization in spinal nerves of 10 to 12 day embryos. FIG. 7F is a whole-mount 10 day embryo showing Nuk protein concentrated within the earliest spinal nerve fibers exiting the neural tube (arrows). FIG. 7G shows a slightly later stage embryo from that shown in FIG. 7F. Notice that the nerve fibers exiting the neural tube have thickened due to fasciculation of additional axons. The insert is a close-up of a single spinal nerve showing Nuk protein is localized throughout its length and can be observed at the leading tips of the growth cones. FIGS. 7H and 7I show transverse sections bisecting the rostral spinal cord of an 11 day embryo demonstrating that the darkly stained Nuk-positive fibers shown in FIGS. 7F and 7G are ventral motor axons (open arrows). At this stage, the accessory nerve also stains positive for Nuk protein as evident by the strong labelling of the axon fibers (filled arrows). The uniform expression of Nuk throughout the spinal region of the neural tube is apparent in these sections.

FIGS. 7J and 7K show both sides of an 11 day whole-mount embryo demonstrating that Nuk protein is localized within the spinal motor nerves as they elongate to the plexus regions (open arrows in FIG. 7J). Between the motor fibers, the appearance of Nuk-positive DRG cell bodies and axons can be observed in this embryo (filled arrows in FIG. 7K). Note that the Nuk-positive DRG axons are more apparent in the posterior/caudal segments of the spinal cord. FIG. 7L shows a close-up of a 12 day whole-mount embryo immunostained with anti-Nuk antibodies which label the nerve fibers of the parasympathetic chain ganglion. Note the ganglia form a chain of interganglionic axonal connections with each other and that each ganglion unit forms connections with two segments of the neural tube.

Scale bars in FIGS. 7B, 7C, 7H, and 7I represent 200 μm.

Immunostained whole-mount 10–10.5 day embryos revealed high levels of Nuk protein in the earliest spinal motor axons as they exit the neural tube (FIGS. 7F and G). The close-up photomicrograph in FIG. 7G shows that Nuk protein is localized throughout the length of the axons including the growth cones. Transverse sections immunostained with anti-Nuk antibodies confirmed that Nuk protein is highly localized to the ventral motor axons and the axons of the DRG (FIGS. 7H and I). Note detectable levels of Nuk protein throughout the spinal cord. By 11 days of development (FIGS. 7J and K) the Nuk-positive nerve fibers have elongated and thickened considerably due to the fasciculation of additional axons along the initial axons which, by this time, have reached the plexus regions (Tosney and Landmesser, J. Neurosci. 4:2518–2527, 1984; Tosney and Landmesser, Dev. Biol. 109:193–2141985a; Tosney and Landmesser, J. Neurosci. 5:2336–2344 1985b; Landmesser and Swain, Neuron 8:291–305, 1992). Nuk protein in the rostral DRG cell bodies and their fibers connecting to the neural tube is also detected (FIGS. 7J and 7K). By 12 days of development only low levels of Nuk immunoreactivity are detected in the motor and DRG axons. At this stage, Nuk protein is detected in axon fibers of the sympathetic chain ganglion (FIG. 7L) and nerve fibers surrounding the heart and diaphram regions.

Example 7
Nuk Protein Early in Ear Development

Figure 8:
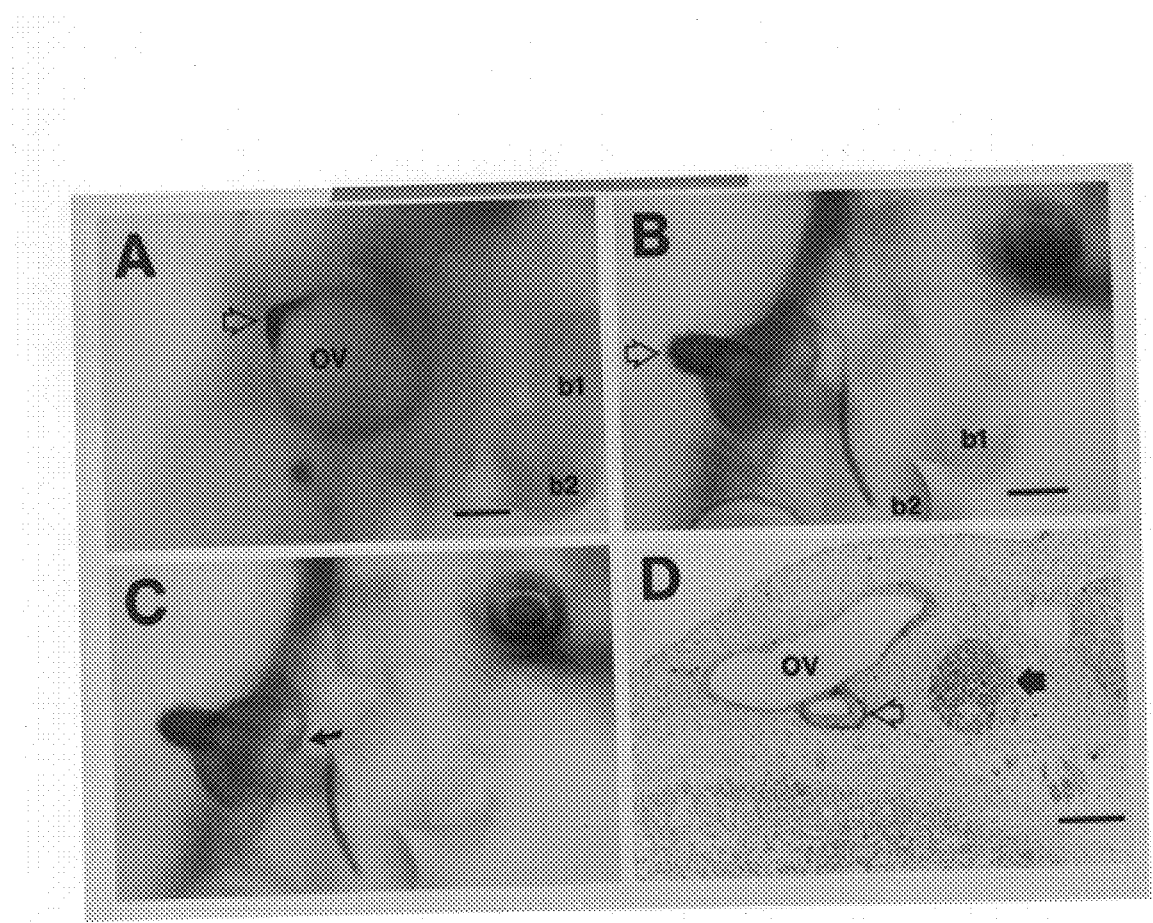
FIG. 8A shows a whole-mount 10.5 day embryo showing Nuk protein localization (arrow) at the dorsal region of the otic vesicle (ov) surrounding the budding endolymphatic duct.
FIG. 8B shows a whole-mount 11.5 day embryo showing elongation of the endolymphatic duct.
FIG. 8C shows a whole-mount 11.5 day embryo at a slightly different focal plane from FIG. 8B showing that the vestibulocochlear sensory fibers connecting to the developing ear stain positive for Nuk protein (arrow)
FIG. 8D shows a transverse section of an 11.5 day embryo showing high levels of Nuk protein localized to the basement membrane of the endolymphatic duct cells where they contact the surrounding mesenchymal cells (open arrow.

Very high levels of Nuk protein were found in specific structures of the developing ear and associated vestibulocochlear (VIII) ganglion in 10.5 to 12.5 day embryos as is shown in FIG. 8.

As shown in FIG. 8, anti-Nuk immunoreacted wholemount 10.5 day embryo detects Nuk protein localization (arrow) at the dorsal region of the otic vesicle (ov) surrounding the budding endolymphatic duct (FIG. 8A). Branchial arches 1 and 2 are indicated. By 11.5 days of development the endolymphatic duct has elongated approximately 200 μm dorsally (FIG. 8B). Nuk protein is observed to envelope this structure (arrow). Nuk protein localization within cranial nerve VII as it enters the second branchial arch can also be seen in FIG. 8B. FIG. 8C shows a slightly different focal plane from (B) showing that the vestibulocochlear sensory fibers connecting to the developing ear stain positive for Nuk protein (arrow). Nuk protein associated with the developing eye is also shown in FIG. 8C. Transverse section of an 11.5 day embryo detects high levels of Nuk protein localized to the basement membrane of the endolymphatic duct cells where they contact the surrounding mesenchymal/neural crest cells (open arrow, FIG. 8D). Nuk protein associated with the vestibulocochlear ganglion is also visible in this section (filled arrow).

The scale bars in FIG. 8 represent the following: (8A), 100 μm; (8B and 8C), 200 μm; (8D), 100 μm.

At 10.5 days Nuk immunostaining associated with the ear is first observed at the dorsal region of the otic vesicle surrounding the initial bulge of the endolymphatic duct (FIG. 8A). By 11.5 days Nuk immunoreactivity encapsulates the endolymphatic duct during its dorsal elongation (FIG. 8B). A different focal plane of the same embryo shows Nuk is also localized to the vestibulocochlear ganglion and its axon fibers connecting to the developing ear (FIG. 8C). Transverse sections detected Nuk protein specifically localized to the basement membrane of the endolymphatic duct cells (FIG. 8D). By 12.5 days of development only low levels of Nuk were detected in the endolymphatic duct and the acoustic ganglion.

Example 8
Generation of Loss of Function Nuk Mutant

A loss of function mutation in Nuk, designated Nuk[1] was generated in embryonic stem cells, and germline transmission of the null allele was obtained as described in more detail below.

A null allele was generated in mouse embryonic stem cells generally following the methodology described in Capecchi M. R., Science 244:1288–1292, 1989. The null mutation was obtained by deletion of exon 2, corresponding to codons 29 to 50, as shown in FIG. 9A. To obtain germ line transmission of the mutation Nuk+/− embryonic stem cell lines (ES) were aggregated with 8 cell embryos in vitro and the resulting blastocysts were transferred into recipient females. Upon birth, animals chimeric for ES and embryonic stem cells were recovered by scoring for eye pigment and coat colour. Breeding of these "aggregation chimeras" confirmed that the germ line of at least one founder mouse is derived completely from the ES cells. Adult mice and embryos homozygous for the mutation did not express Nuk protein as determined by in vitro kinase assays performed on washed immunoprecipitates as described herein (FIG. 9B).

Example 9
Generation of a Nuk-lac Z Fusion Chimeric Receptor Mutant

A targeted mutation, designated Nuk$^2$ was generated in the Nuk gene as shown in FIG. 10. A pPNT-LOX-Nuk$^2$ gene trap vector was used to delete the GXGXXG ATP binding region of the kinase domain (amino acids 623–707, SEQ ID NO:2 and FIG. 2) to create a Nuk-lac Z fusion receptor in ES cells. Chimeric animals were prepared as described above, by aggregating the ES cells with 8 cell CD1 embryos.

Animals generated with the Nuk$^2$ mutation provided Nuk expressing cells staining for β-galactosidase activity, providing a convenient marker for Nuk-positive cells in both heterozygous and homozygous backgrounds. The Nuk$^2$ mutation led to the expression of a Nuk-lac Z fusion protein in mouse heterozygous embryos, detected by a blue/green colour as shown in FIGS. 11 and 12.

Figure 11A:
FIG. 11A shows expression of the $Nuk^2$ mutation in a mouse embryo at the 14 somite stage (8.75 days development) in the hindbrain rhombomeres, the midbrain, diencephalon and in the heart (B)
Figure 11B:
FIG. 11B shows expression of the $Nuk^2$ mutation in a mouse embryo at the six somite stage (8.25 days development) in the brain and developing heart, the Nuk-lac Z mutant receptor faithfully indicates the endogenous expression pattern of Nuk with a blue/green stain.
Figure 12A:
FIG. 12A shows $Nuk^2$ expression in a 10.5 day old mouse embryo in the ventral midbrain, dienchephalon and retinal cells.
Figure 12B:
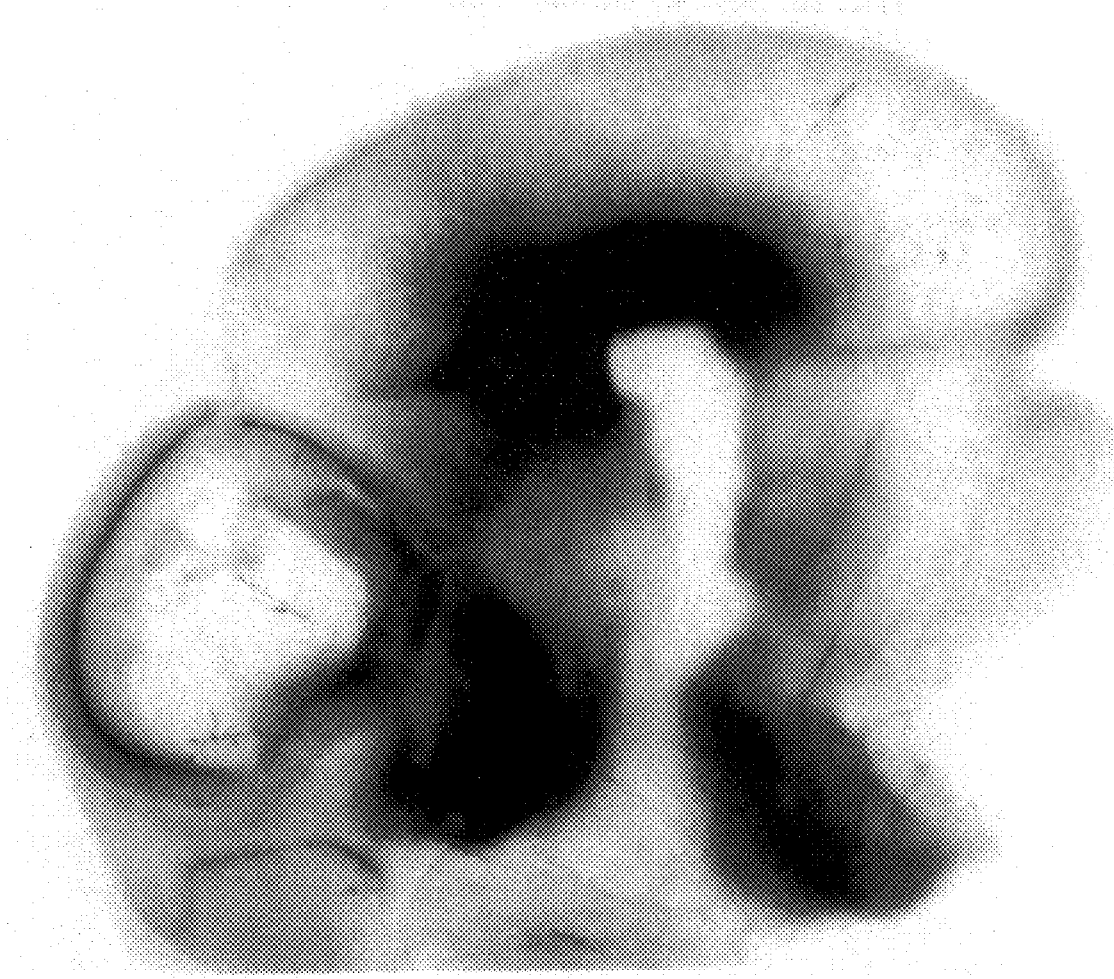
FIG. 12B shows $Nuk^2$ expression in a 10.5 day old mouse embryo in the brain and spinal cord.

FIG. 11A shows an embryo at the six somite stage (8.25 days development) expressing the Nuk$^2$ mutation in the brain and developing heart. FIG. 11B shows that at the 14 somite stage (8.75 days development) expression continues in the hindbrain rhombomeres, the midbrain and diencephalon and persists in the heart. FIG. 12 shows Nuk$^2$ expression in a 10.5 day old embryo. FIG. 12A illustrates the very high levels of expression in the ventral midbrain, dienchephalon and retinal cells (which are out of focus in the photomicrograph). FIG. 12B illustrates expression in the brain and spinal cord.

Example 10
Autophosphorylation of Nuk Protein by ELK-Ligand

Figure 13:
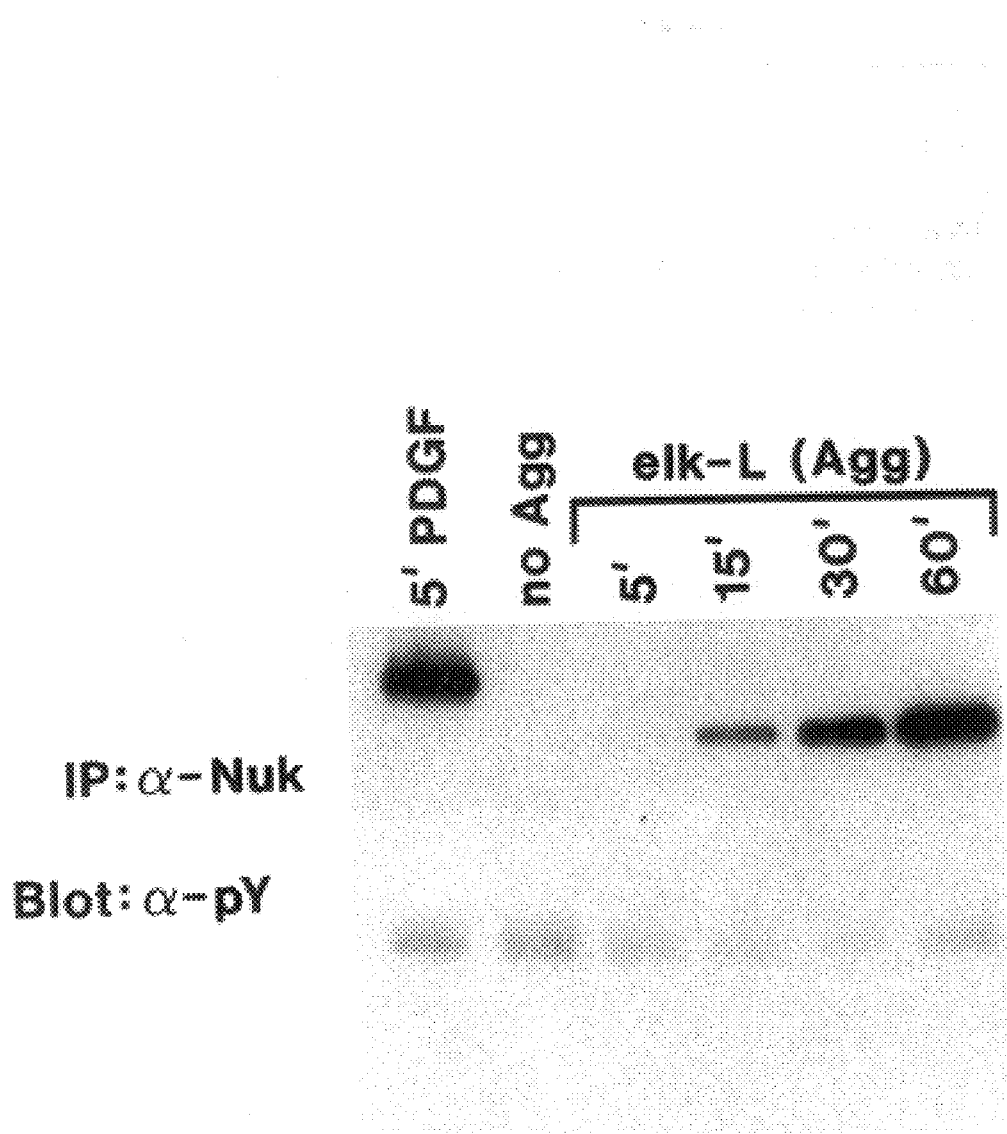
FIG. 13 shows an immunoblot illustrating that Nuk protein autophosphorylation is induced by Elk-ligand stimulation.

Fusion proteins consisting of the extracellular domain of Elk-ligand (Davis, S., et al. Science Vol. 266, Nov. 4, 1994, p.816) linked to the Fc portion of human immunoglobulin G1 were made in COS cells S/N following the methods outlined in Davis et al, 1994, supra. The expressed ligand was aggregated with anti-human Fc antibody and incubated with COS cells for 5 minutes, 15 minutes, 30 minutes or 1 hour. Following incubation, the COS cells were lysed and the lysate was immunoprecipitated with anti-Nuk antibodies. The immunoprecipitates were subjected to Western blotting analysis with anti-phosphotyrosine antibodies. FIG. 13 shows the autophosphorylation of Nuk on tyrosine from 15 minutes to one hour following Elk-ligand stimulation. Therefore, Nuk autophosphorylation is induced by stimulation with the Elk-ligand.

Example 11
Nuk Expression in Cell Lines

Figure 14:
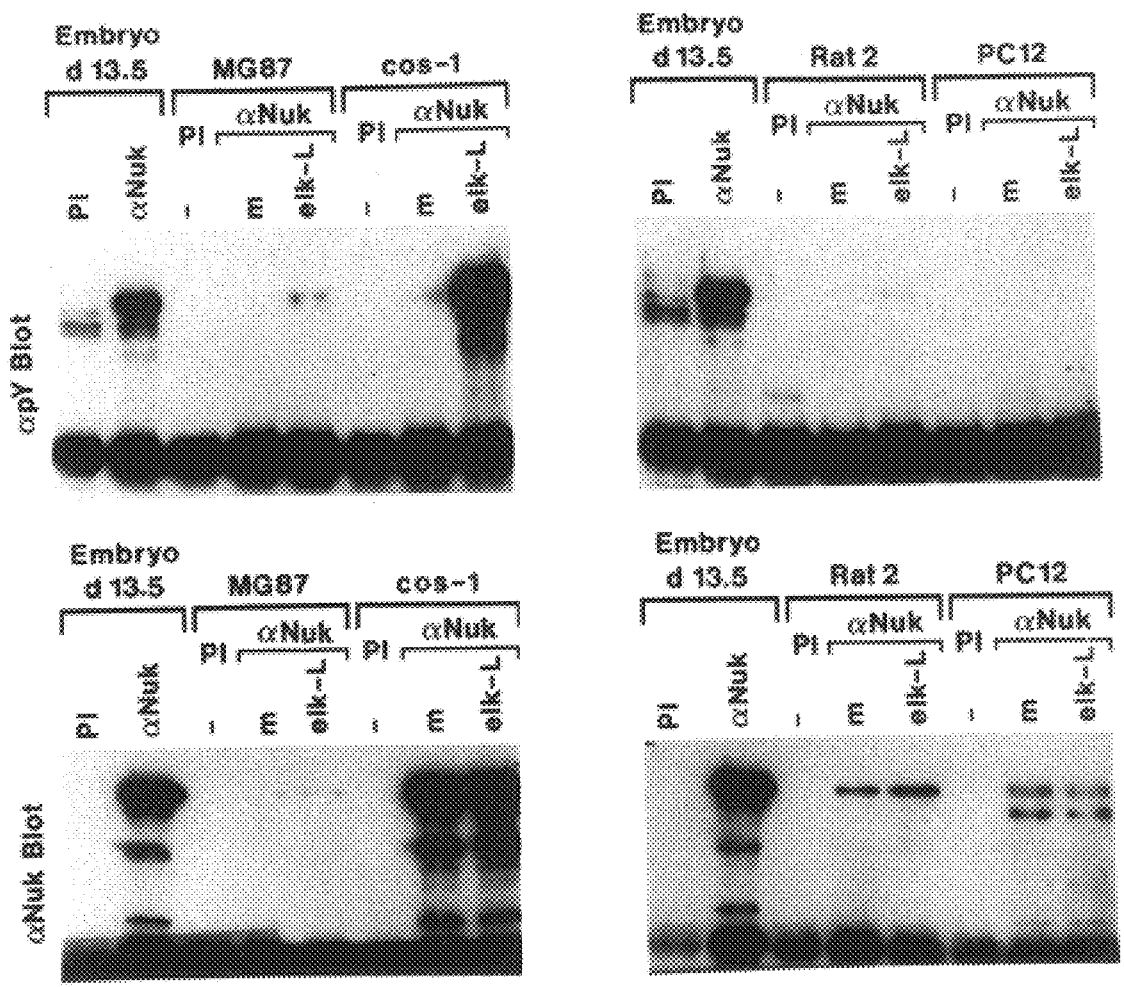
FIG. 14 is an immunoblot showing expression of Nuk protein in cell lines.

Various cell lines were screened for expression of Nuk protein. Cells were homogenized and the homogenate was incubated with anti-Nuk antibody and the immunoprecipitates were collected by centrifugation. The washed immunoprecipitates were separated by SDS-polyacrylamide gel electrophoresis and subjected to Western blotting with anti-Nuk antibodies or anti-phosphotyrosine antibodies. As shown in FIGS. 14 and in Table 1, COS cells expressed high levels of Nuk protein.

TABLE 1

|  | MG87 | COS | Rat2 | PC12* |
|---|---|---|---|---|
| Nuk protein | + | ++++ | + | + |

(*NB/ can't stimulate with elk-ligand)

Example 12
GST-Fusion Mixing Experiments with Nuk in Vitro Phosphorylation

Figure 15:
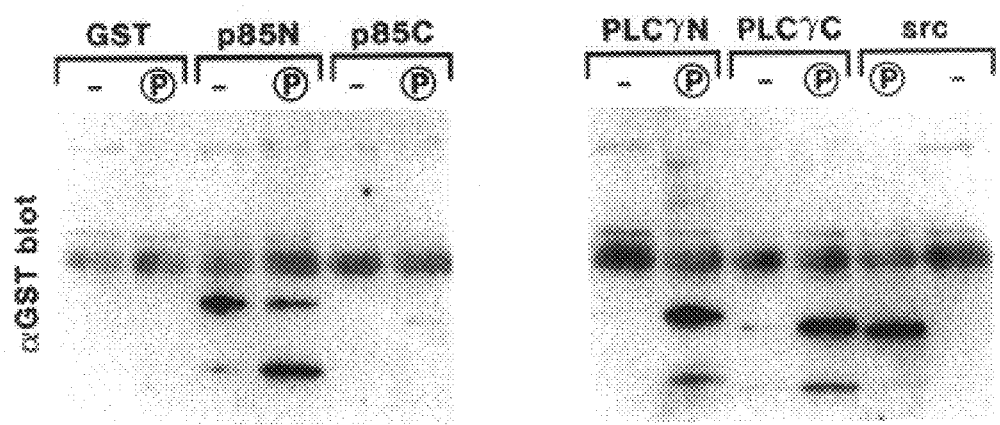
FIG. 15 is an immunoblot showing binding of phosphorylated/non-phosphorylated Nuk protein to SH2-containing GST-fusion proteins.
Figure 16:
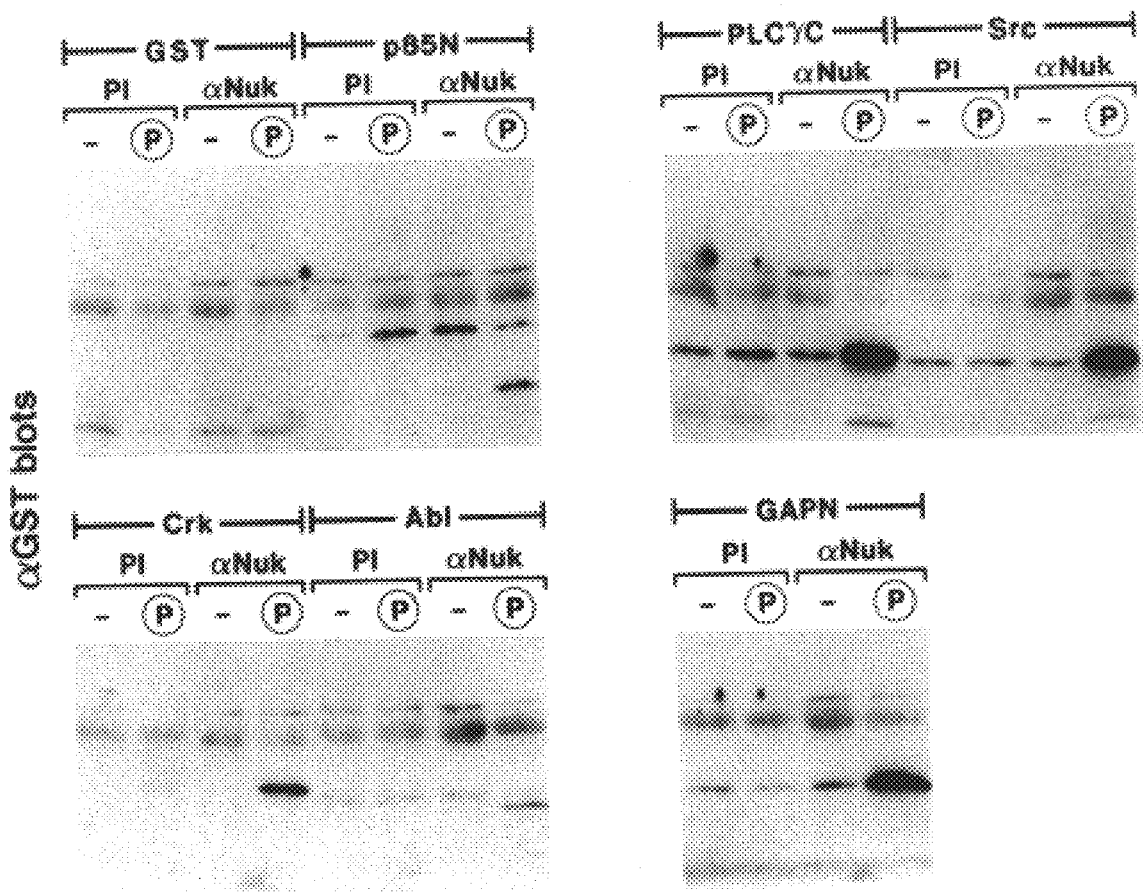
FIG. 16 is an immunoblot showing binding of phosphorylated/non-phosphorylated Nuk protein to SH2-containing GST-fusion proteins.

GST-fusion proteins containing SH2 domains of p85N, p85C, PLCγN, PLCγC, GAPN, Src, Crk, Ab1, and Grb2 were made in E. coli. Nuk protein was immunoprecipitated from lysates of COS cells using Nuk antisera, and phosphorylated by incubation with ATP. Bacterial lysates containing the GST fusion proteins were incubated with phosphorylated/non-phosphorylated Nuk protein. Western blots were prepared using anti-GST antibodies. The results are shown in FIGS. 15 and 16, and they are summarized below in Table 2.

TABLE 2

| Fusion Protein | Nuk | |
|---|---|---|
|  | Non-phosphorylated | Phosphorylated |
| GST | − | − |
| p85N | +/− | +/− |
| p85C | − | + |
| PLCγN | − | ++ |
| PLCγC | ++ | ++++ |
| GAPN | + | +++ |
| Src | + | ++++ |
| Crk | − | + |
| Ab1 | − | + |
| SH2 | − | − |
| Grb2 | No | No |

As shown in Table 2, phosphorylated Nuk protein bound to fusion proteins containing SH2 domains of PLCγN, PLCγC, Src, and GAPN.

Example 13
GST-Fusion Mixing Experiments with Nuk in Vitro Phosphorylation

Figure 17:
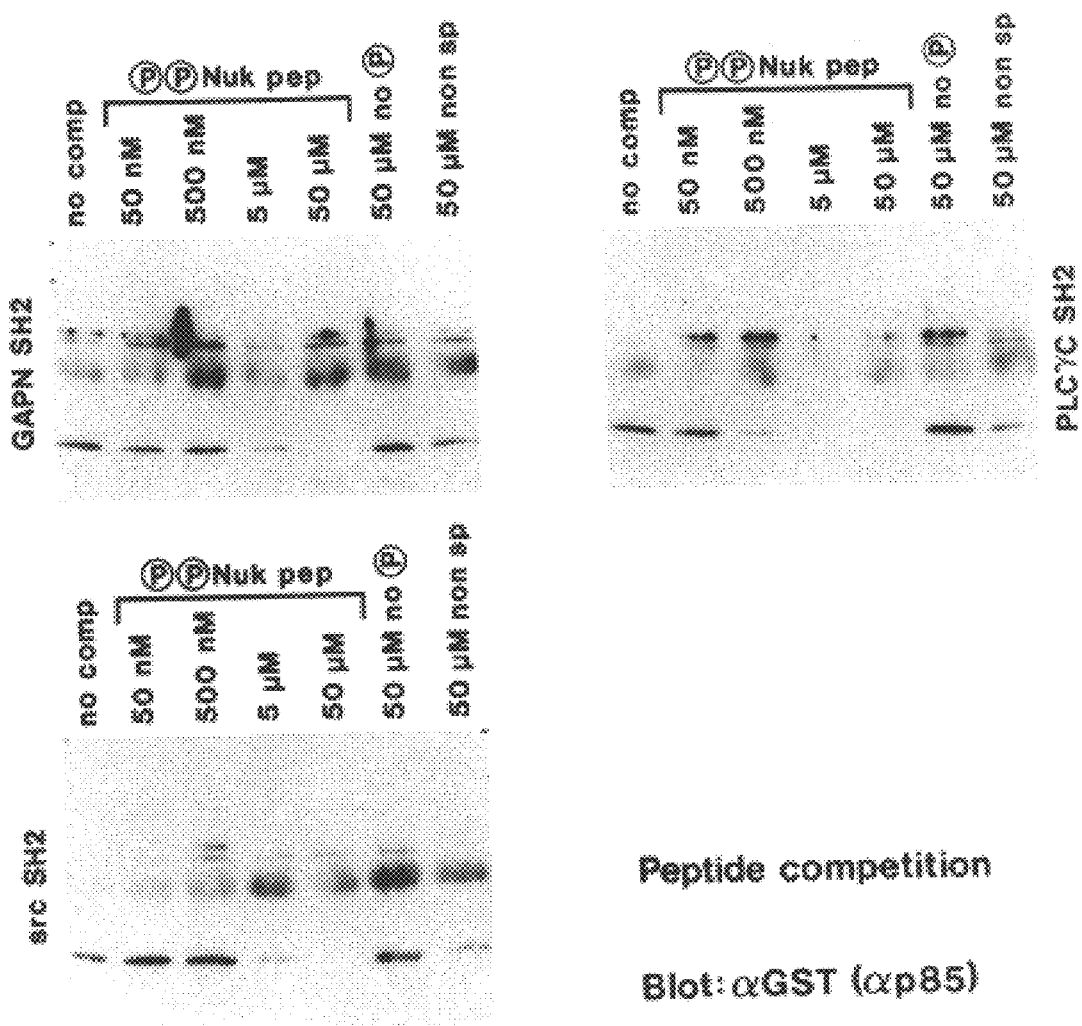
FIG. 17 is an immunoblot showing binding of Nuk Protein to SH2-containing GST-fusion proteins in the presence of a competing phosphorylated peptide.

The experiments described in Example 12 were also carried out in the presence of a competing phosphorylated peptide-GMKT$_P$YIDPFT$_P$YEDPNEAVR(K) from the Nuk membrane proximal region. In particular, Nuk from COS cells obtained with Nuk antisera was phosphorylated by incubation with ATP. The phosphorylated Nuk was incubated with bacterial lysates from SH2-GST fusion protein expressing bacteria, in the presence or absence of the competing peptide. Western blots for were prepared using anti-GST antibodies. As shown in FIG. 17, the Nuk phosphorylated peptide competes in vitro with the interaction of GAP, PLCγ, and Src SH2 fusion proteins. Unphosphorylated peptide did not interfere with the interaction nor did a nonspecific Trk SHC-binding peptide (HIAENPQY$_P$FSD).

Example 14

Figure 18:
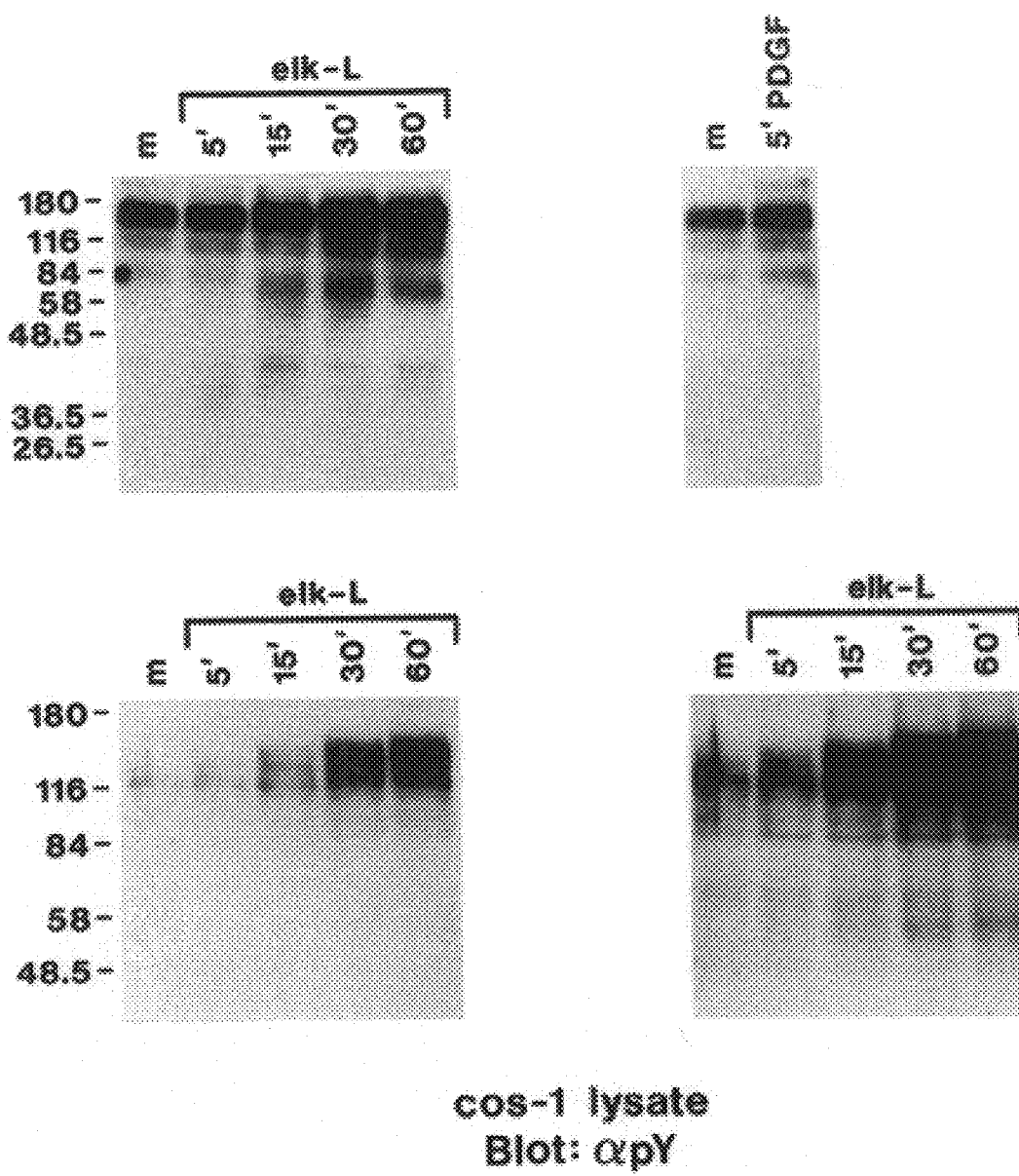
FIG. 18 shows immunoblots illustrating the phosphorylation of proteins after ELK-ligand stimulation of COS cells.

The phosphorylation of proteins after Elk-ligand stimulation in Nuk expressing COS cells was investigated. Antiphosphotyrosine Western blots were prepared from whole cell lysates of COS cells stimulated with Elk-ligand. The results are shown in FIG. 18. Proteins of about 160, 130 (probably Nuk), 58 and 40 KD were found to be phosphorylated on tyrosine after Elk-ligand stimulation.

Having illustrated and described the principles of the invention in a preferred embodiment, it should be appreciated to those skilled in the art that the invention can be modified in arrangement and detail without departure from such principles. We claim all modifications coming within the scope of the following claims.

Example 15

The role of Nuk protein, the extracellular domain of Nuk protein and the catalytic kinase domain of Nuk protein were investigated as follows. Loss of function Nuk mutant mice, designated Nuk$^1$ were prepared as described in Example 8 herein. These mice may also be referred to as null mice as they do not express Nuk protein. Nuk-lac Z fusion chimeric receptor mutant mice, designated Nuk$^2$ were prepared as described in Example 9 herein. These mice express a fusion protein having the entire extracellular domain of Nuk, but lacking in the Nuk catalytic kinase domain, which is replaced by β-galactosidase. All mice, exhibited apparently normal appearance and behaviour.

To analyze the brains of Nuk mutant mice, specimens were dissected and fixend in 4% paraformaldehyde in PBS. the fixed specimens were either embedded in paraffin and sectioned on a microtome or cryprotected in 30% sucrose and sectioned using a cryostat to obtain serial sections.

Serial sections were taken of a number of brains of heterozygous control and both Nuk$^1$ and Nuk $^2$ homozygous embryos at E14.5 to E18.5 days of embryonic development and of newborn and adult mice at 1 to 1.5 years of age. 6 to 30 μm thick coronal or horizontal sections were prepared and viewed on a compound microscope under bright field or polarized light. FIGS. 19A, 19B, 19C and 19D show photomicrographs of horizontal sections taken across the anterior of the temporal lobes at the level of the anterior commissure and pars posterior medial tract, which connects the frontal lobes. In heterozygous Nuk$^1$/+ mice the pars posterior medial tract, and the pars anterior tract of the anterior commissure are clearly visible (FIG. 19A) and appear the same as in wild type mice. Serial sections show that the pars posterior medial tract forms a continuous tract between the two frontal lobes. The entire medial tract is not visible in FIG. 19A due to the plane of the section.

Figure 25:
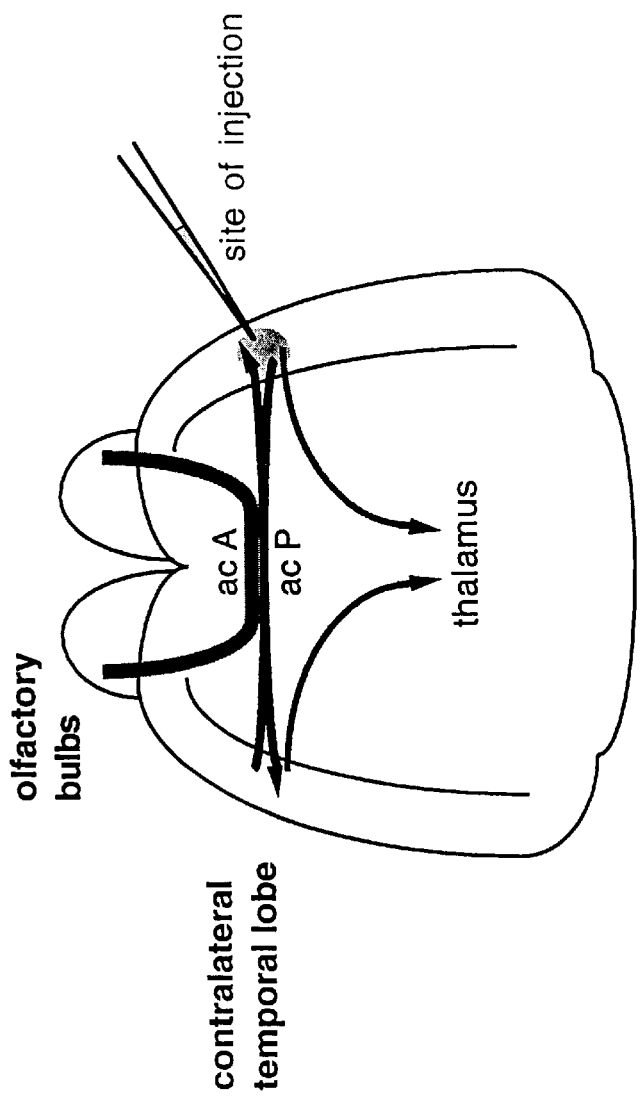
FIG. 25 is a diagram illustrating the fast blue tracing of the temporal lobe.

The presence of a continuous pars posterior medial tract communicating between the frontal lobes, was confirmed by dye injection experiments, which are illustrated diagramatically in FIG. 25. Briefly, a fluorescent dye (fast blue) was injected into one temporal lobe of anaesthetized adult mice, either heterozygous or homozygous for the Nuk$^1$ mutation, approximately one year old, through standard surgical techniques. Mice were revived and the fast blue was allowed to travel through the axons of the temporal neurons that received dye for 2 days, after which the mice were sacrificied, perfused with fixative, and the brains were collected and post-fixed. After cryoprotection in 30% sucrose, serial sections were prepared and the brain sections were viewed by fluoresence microscopy. Where the dye was found to have been transported across to the opposite frontal lobe, the presence of an intact medial tract was confirmed.

Figure 19A:
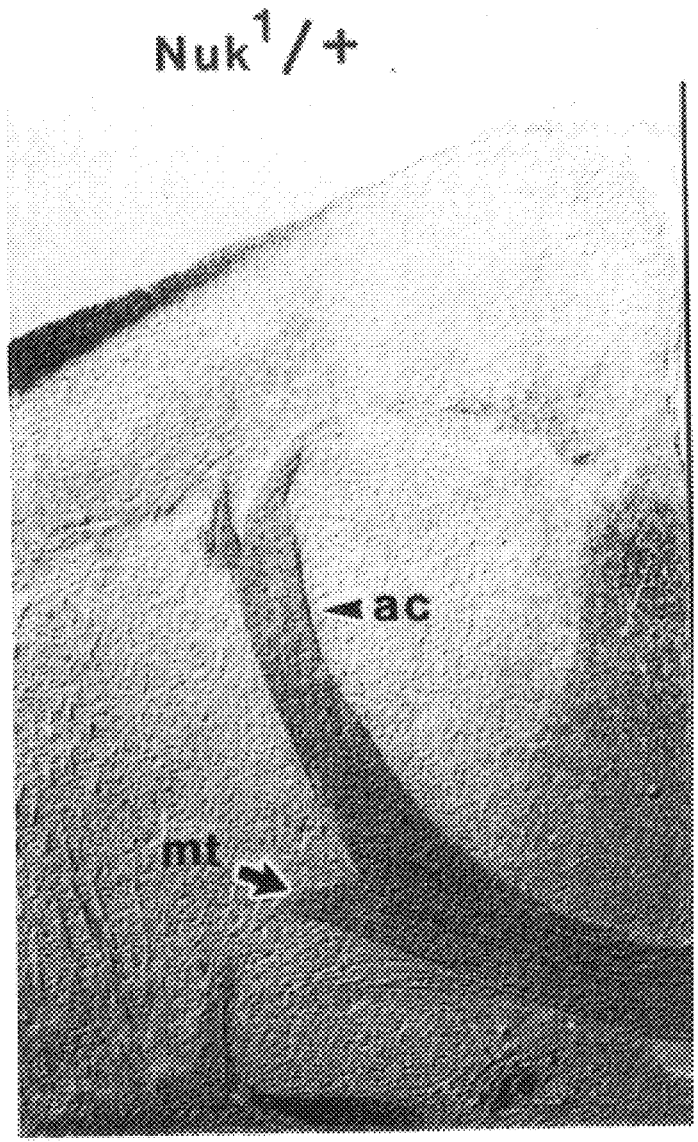
FIG. 19A is a photomicrograph showing a horizontal section taken through the brain of a heterozygous $Nuk^1/+$ mouse across the anterior of the frontal lobes (ac=anterior commissure, mt=medial tract)
Figure 19B:
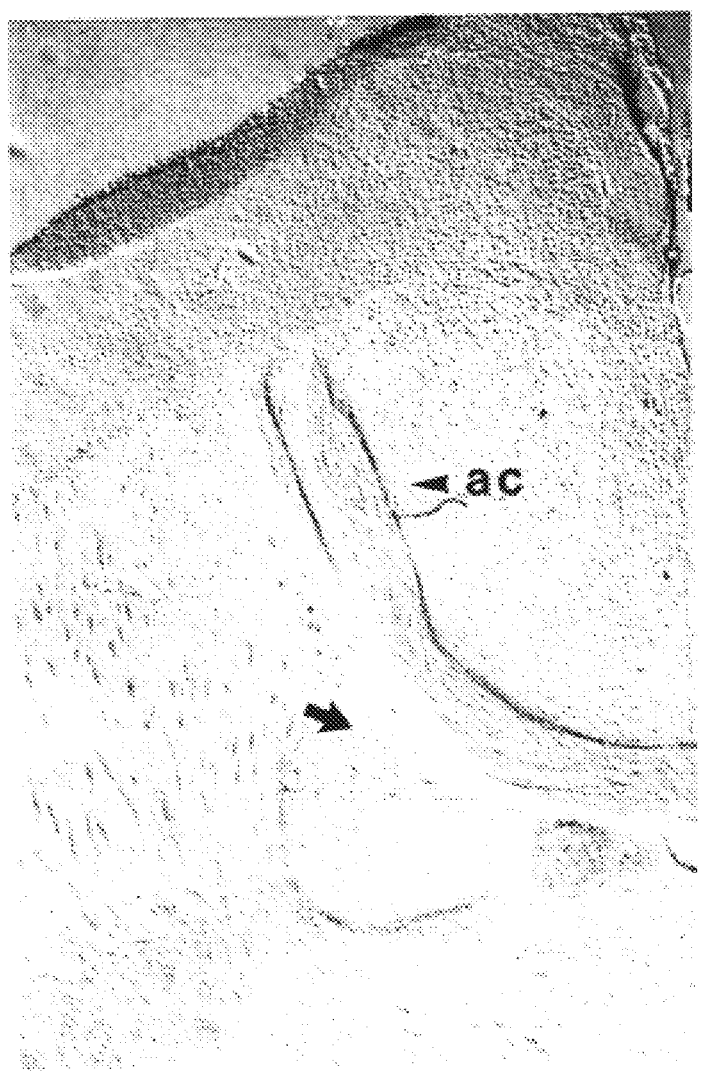
FIG. 19B is a photomicrograph showing a horizontal section taken through the brain of a homozygous $Nuk^2/Nuk^2$ mouse across the anterior of the frontal lobes.
Figure 19C:
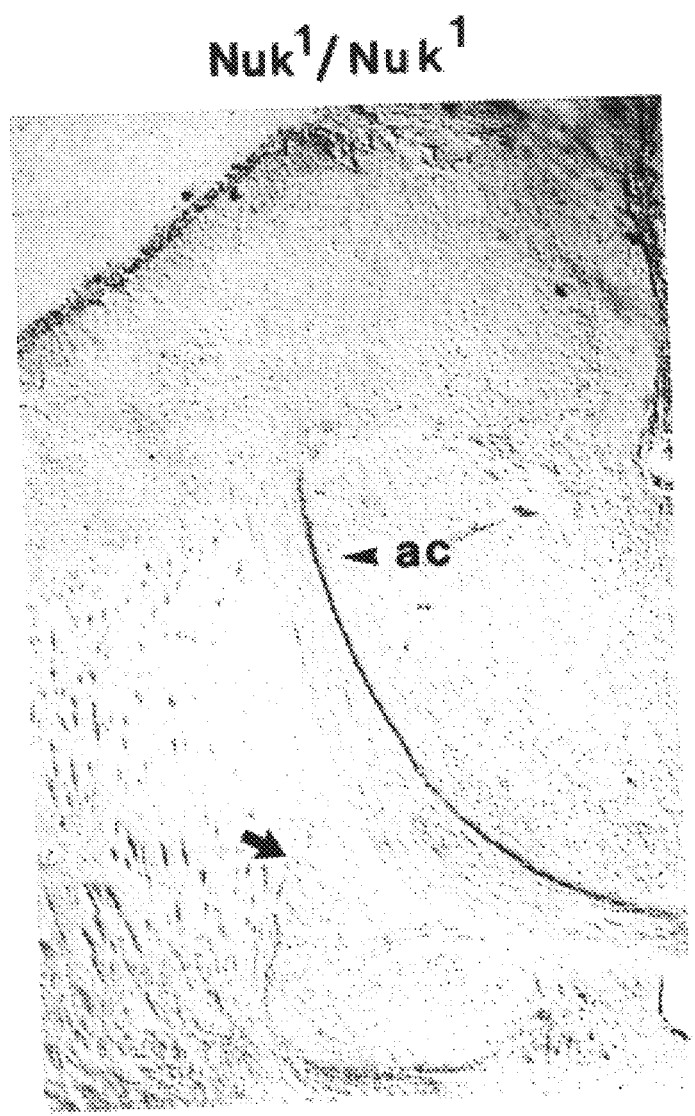
FIG. 19C is a photomicrograph showing a horizontal section taken through the brain of another homozygous Nuk$^1$/Nuk$^1$ mice across the anterior of the frontal lobes.
Figure 19D:
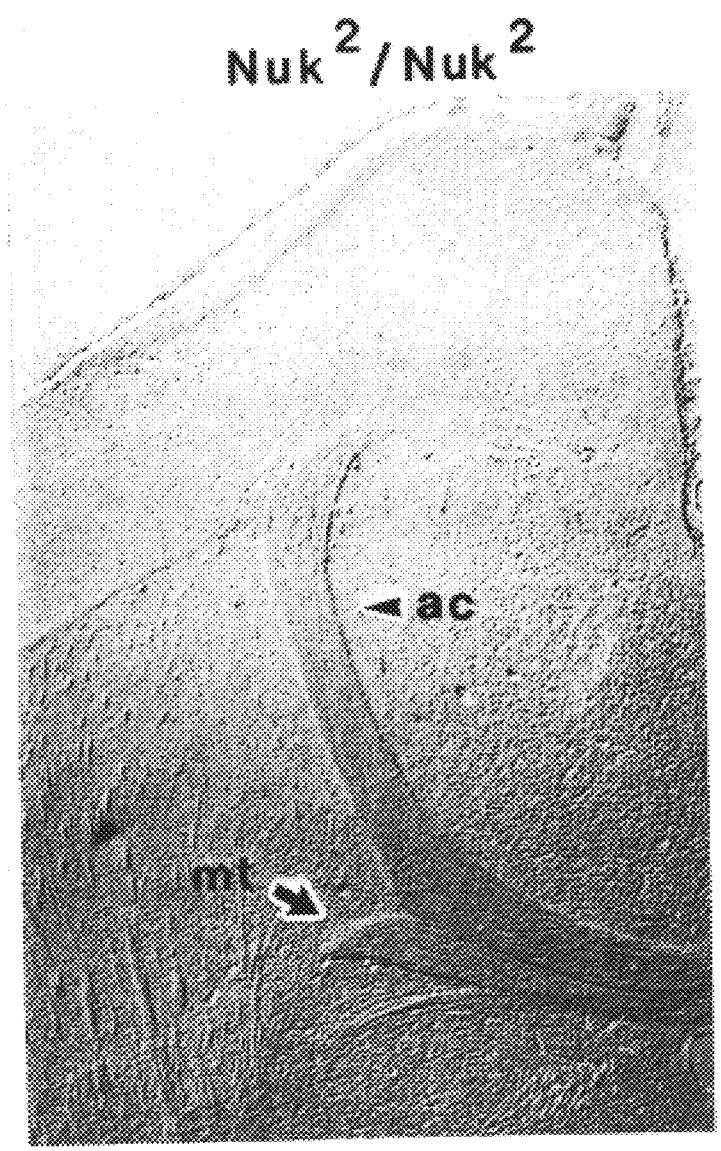
FIG. 19D is a photomicrograph showing a horizontal section taken through the brain of a homozygous Nuk$^2$/Nuk$^2$ mouse across the anterior of the frontal lobes.
Figure 19E:
FIG. 19E is a photornicrograph of a horizontal section taken through the brain of a Nuk$^1$/+ mouse across the anterior of the frontal lobes, showing the medial tract of the anterior commissure.
Figure 19F:
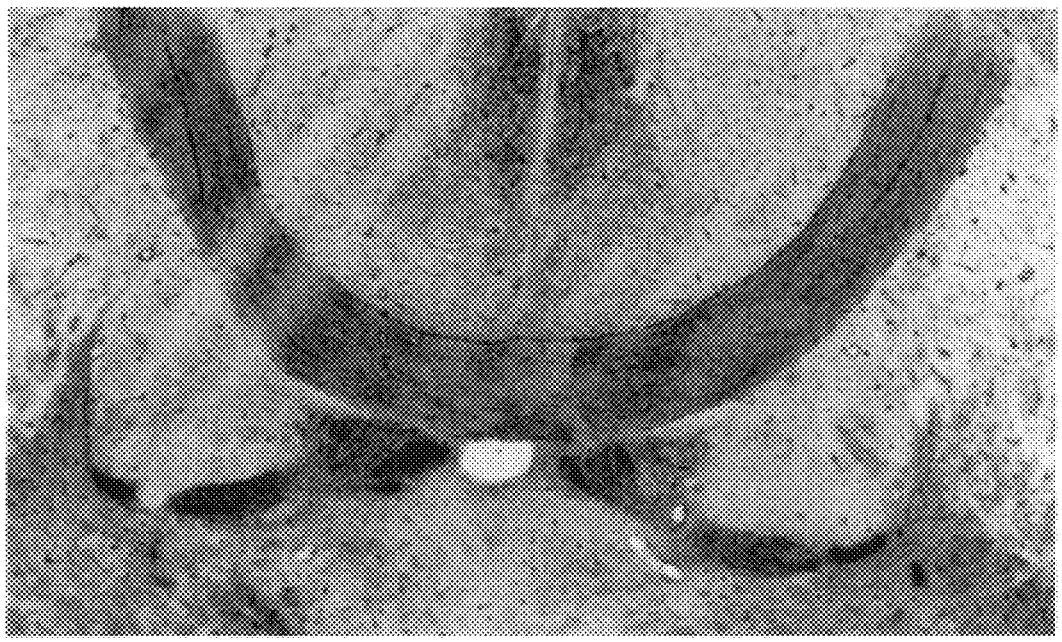
FIG. 19F is a photomicrograph of a horizontal section taken through the brain of a homozygous Nuk$^1$/Nuk$^1$ mouse across the anterior of the frontal lobes, showing the absence of the medial tract of the anterior commissure.
Figure 20:
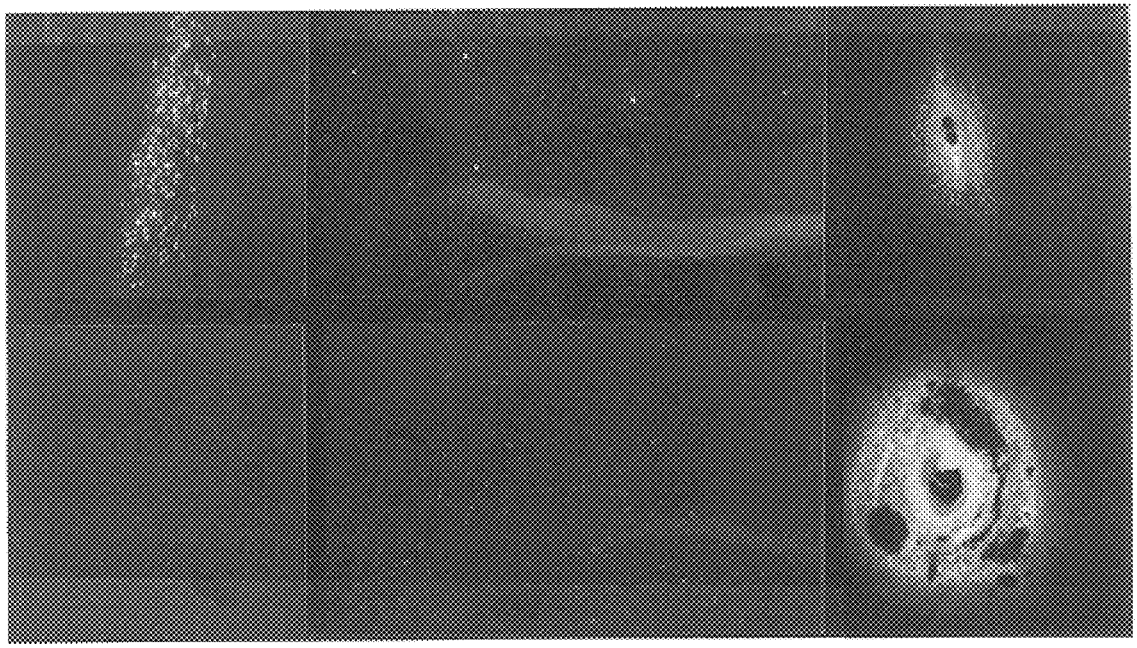
FIG. 20 shows horizontal sections taken through the brains of Nuk$^1$/Nuk$^1$ (bottom) and Nuk$^1$/+ (top) mice injected in one frontal lobe with a fluorescent dye, fast blue.

In homozygous Nuk$^1$/Nuk$^1$ null mice the pars posterior medial tract was found to be absent as shown in FIGS. 19B, 19C and 19F. Absence of the medial tract was confirmed by the inability of dye injected into one frontal lobe to cross to the opposite frontal lobe as shown in FIG. 20 (bottom). Absolutely no label was detected in the opposite frontal lobe, even when large amounts of dye were injected to maximize labelling. In Nuk$^1$/+ mice, however, small amounts of dye were sufficient to produce visible labelling in the opposite frontal lobe, as shown in FIG. 20 (top). Labeling was detected in the medial tract of Nuk$^1$/+ mice but not in Nuk$^1$/Nuk$^1$ mice. This directly shows that expression of Nuk protein is required for the formation of the medial tract.

In homozygous Nuk$^2$/Nuk$^2$ mice the medial tract was found to be present, as shown in FIG. 19D and was shown by dye injection to form a continuous connection between the frontal lobes, as in the wild type and Nuk$^1$/+ heterozygotes. This surprisingly indicates that the extracellular domain of Nuk, in the absence of the catalytic kinase domain, is sufficient for formation of the medial tract. This is believed to be the first showing of a functional role for the extracellular domain of a receptor tyrosine kinase which is independent of the catalytic kinase domain. A role for the transmernbrane and juxtamembrane domains of Nuk protein can not be ruled out as the chimeric Nuk-β-galactosidase fusion protein has these domains in addition to the extracellular domain.

In view of the importance of Nuk protein in the formation of the pars posterior medial tract, a detailed study of the expression of Nuk in this region of the brain was made by examining serial sections from the brains of Nuk$^2$/Nuk$^2$ homozygous mice, which express a fusion protein comprising the Nuk extracellular transmembrane and juxtamembrane domains and μ-galactosidase, which can readily be detected in sections based on the a blue green coloration, as described in Example 9 herein and shown in FIGS. 11A, 11B and 12A and 12B. Sections were taken from the brains of Nuk$^2$/Nuk$^2$ mice and newborn pupsand from embryos at various stages of gestation.

Figure 21A:
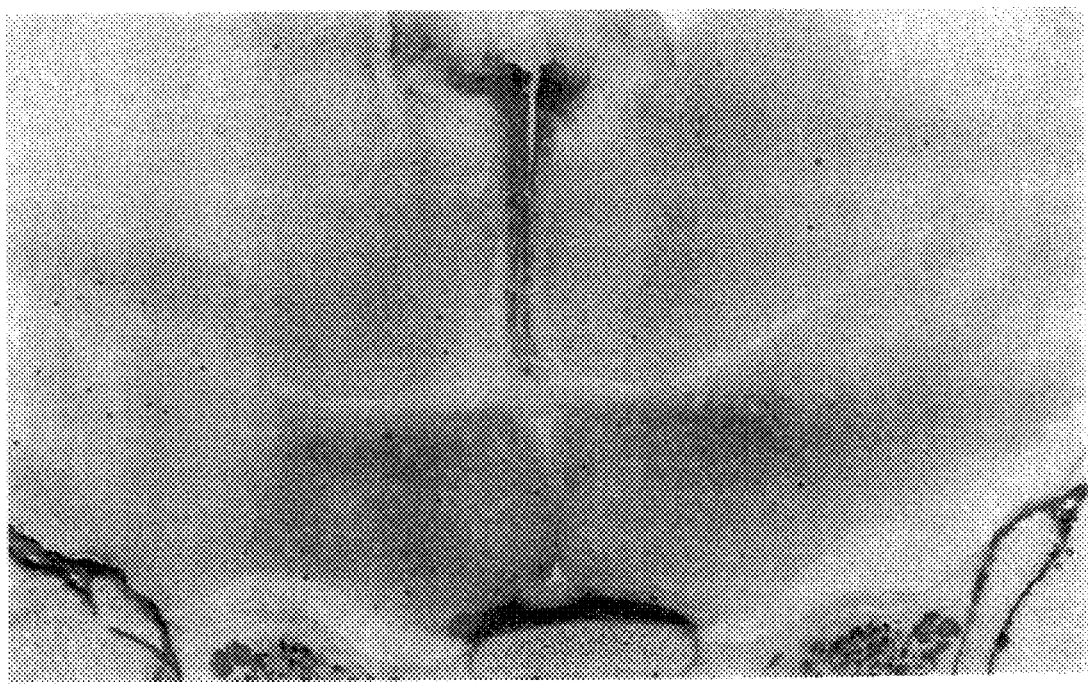
FIG. 21A shows a coronal section through the brain of a Nuk$^2$/Nuk$^2$ mouse embryo, showing lack of expression of Nuk-lac Z in the medial tract of the anterior commissure.
Figure 21B:
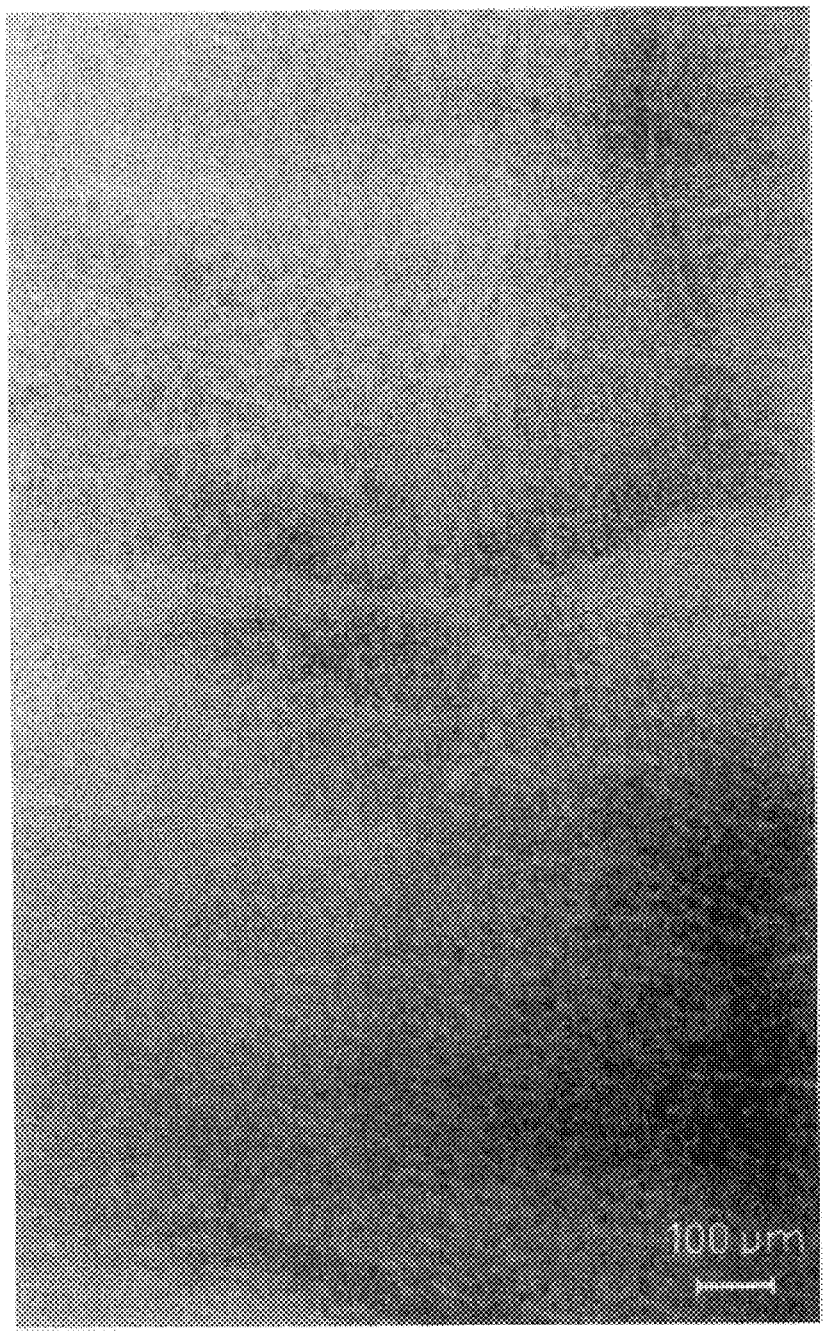
FIG. 21B shows a coronal section through the brain of a Nuk$^2$/Nuk$^2$ newborn mouse, showing lack of expression of Nuk-lac Z in the medial tract of the anterior commissure.

Nuk was not found to be expressed in the pars posterior medial tract of embryonic or adult Nuk$^2$/Nuk$^2$ mice. Nuk expression was absent dorsal to the medial tract but apparent in the cells ventral to and underlying the medial tract as shown in FIGS. 21A and 21B. FIGS. 21A and 21B show the apparent lack of expression of Nuk-lac Z in the medial tract of the anterior commissure in E16.5 embryos and newborn mice respectively. FIG. 21A also shows intense staining of the optic nerve/optic chiasma and trigeminal ganglia.

Nuk was generally found to be widely expressed in the brain, with an apparent increase in level posteriorly. Peripheral axons were found to express high levels of Nuk. In particular, the retinal ganglia cells of the eyes exhibited intense blue/green staining. The olfactory receptor neurons, the trigeminal ganglia and associated sensory whisker roots were also found to express Nuk. The corpus callosum, the thick stratum of transversely-directed nerve fibres which connects the two hemispheres of the brain, was also stained for Nuk expression.

Figure 22A:
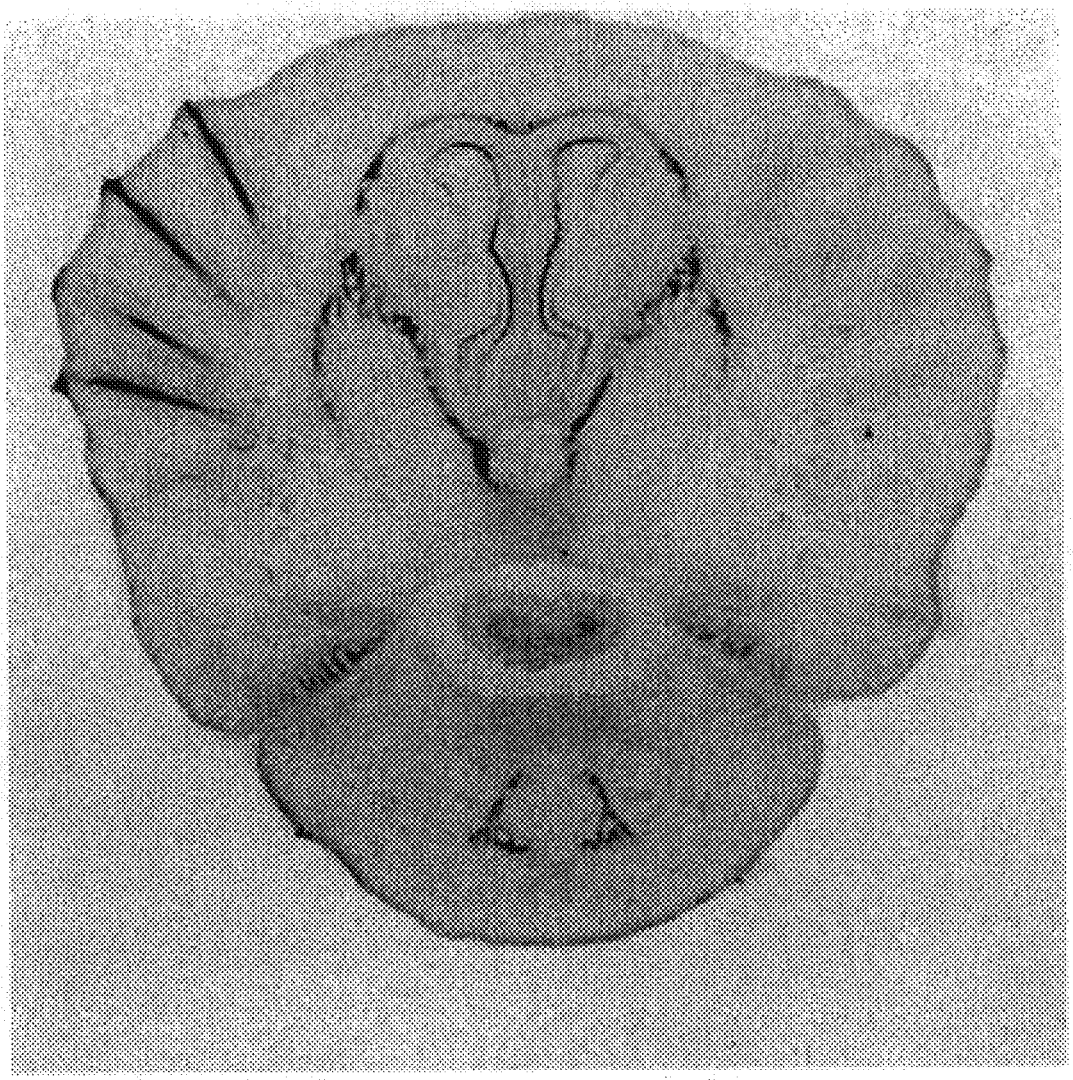
FIG. 22A shows a coronal section through the anterior brain region of an E16.5 Nuk$^2$/Nuk$^2$ embryo, showing staining of the sensory neurons surrounding the whiskers and presumptive sensory structures in the gum/teeth and tongue regions.
Figure 22B:
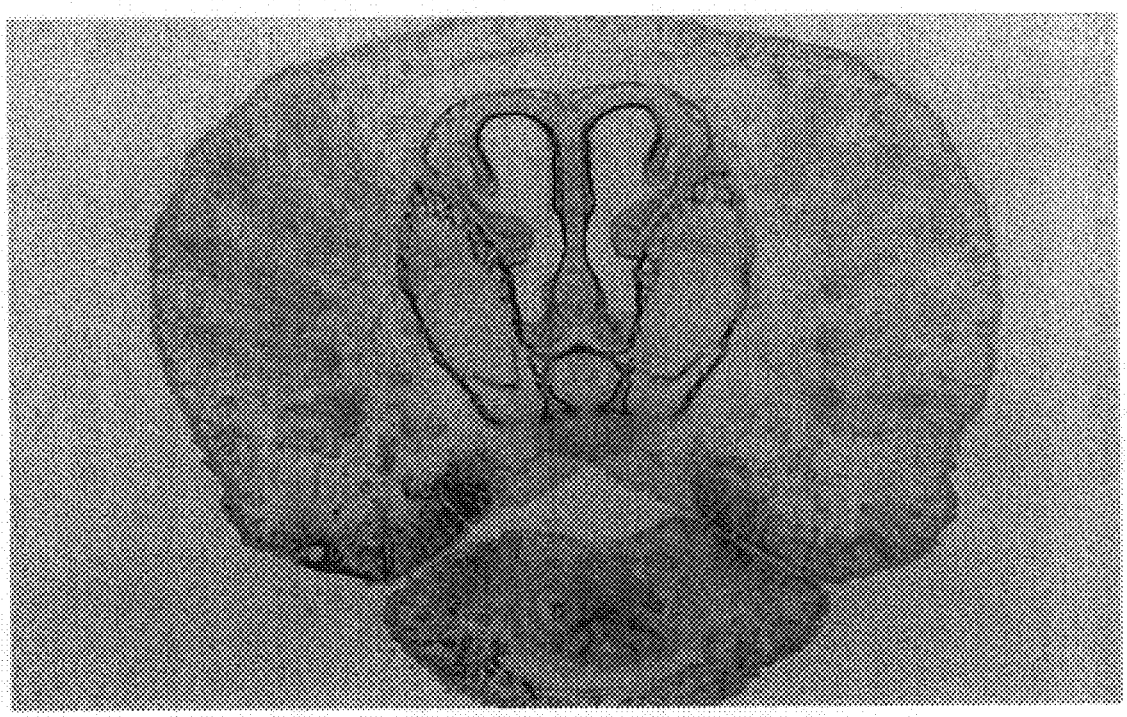
FIG. 22B shows a coronal section through the anterior brain region of a Nuk$^2$/Nuk$^2$ newborn mouse showing staining of the sensory neurons surrounding the whiskers.
Figure 22C:
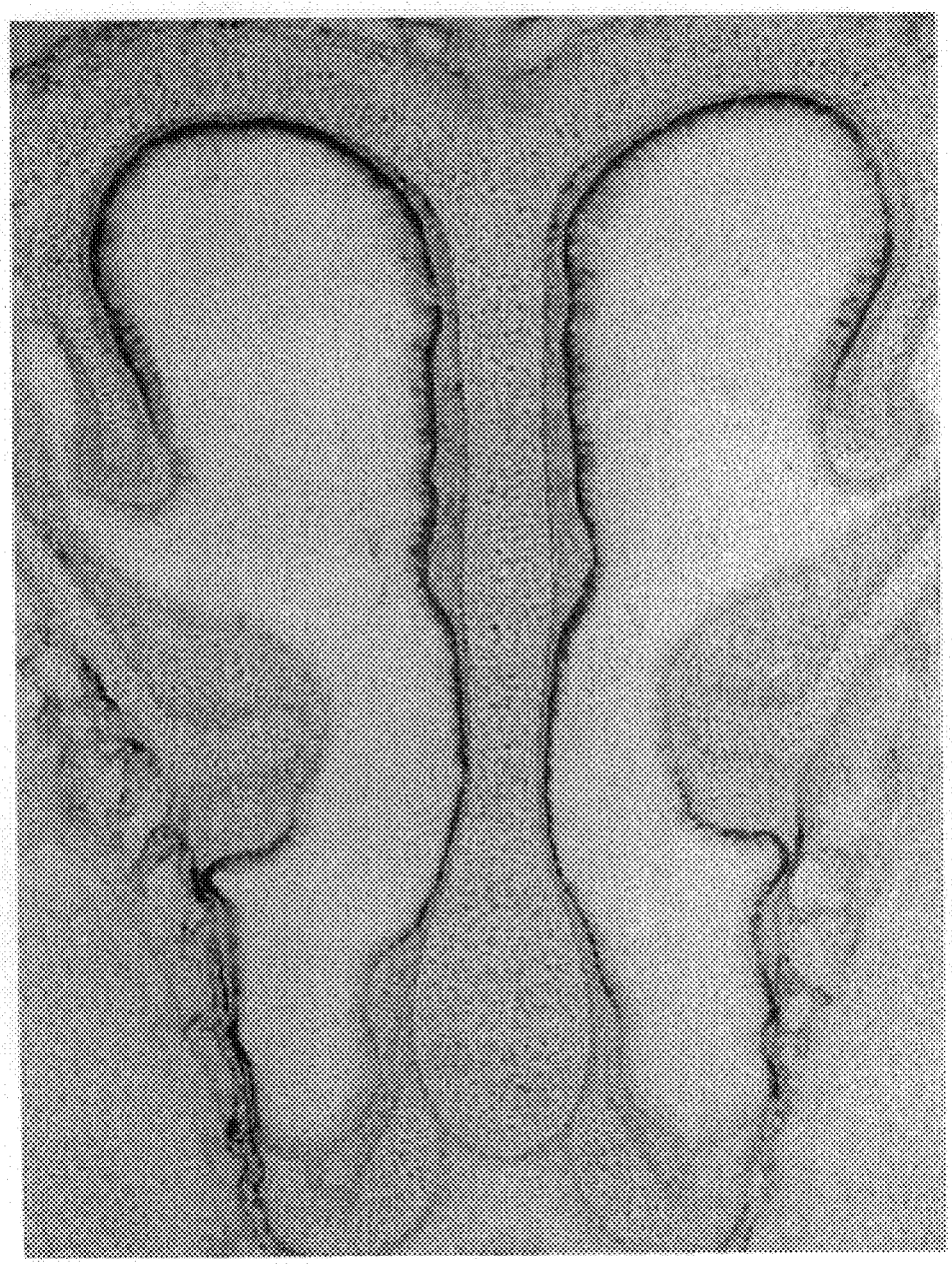
FIG. 22C shows a coronal section through the anterior brain region of a Nuk$^2$/Nuk$^2$ newborn mouse showing staining of the olfactory receptor neurons.
Figure 22D:
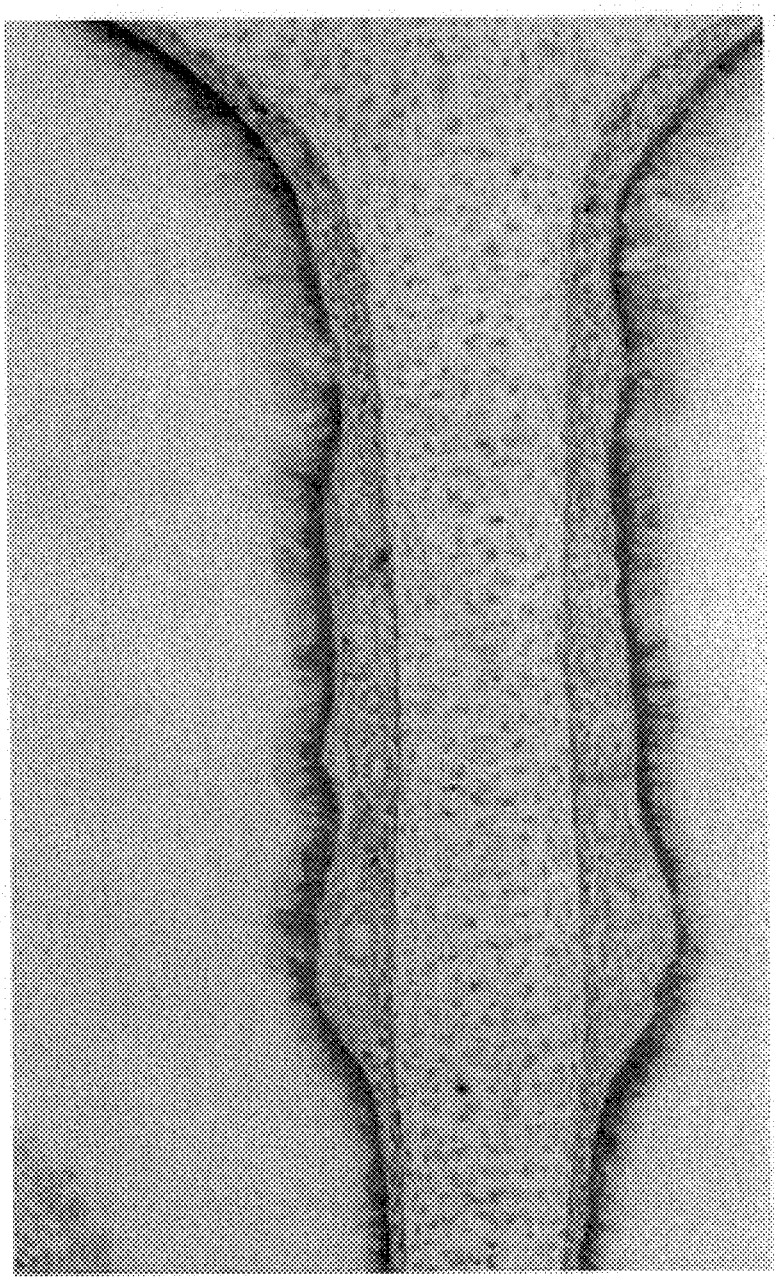
FIG. 22D shows a coronal section through the anterior brain region of a Nuk$^2$/Nuk$^2$ newborn mouse showing staining of the olfactory receptor neurons.

Nuk-lacZ expression in the anterior region of the brain of an E16.5 embryo is shown in FIG. 22A. The sensory neurons surrounding the whiskers, putative sensory structures in the gums/teeth region, the nose and tongue were also stained. FIGS. 22B, 22C and 22D show coronal sections through the anterior of the brain of newborn mice. FIG. 22B shows staining of the sensory neurons surrounding the whiskers. FIGS. 22C and 22D are higher magnifications of the olfactory epithelium showing the very intense staining of the olfactory receptor neurons.

Figure 23A:
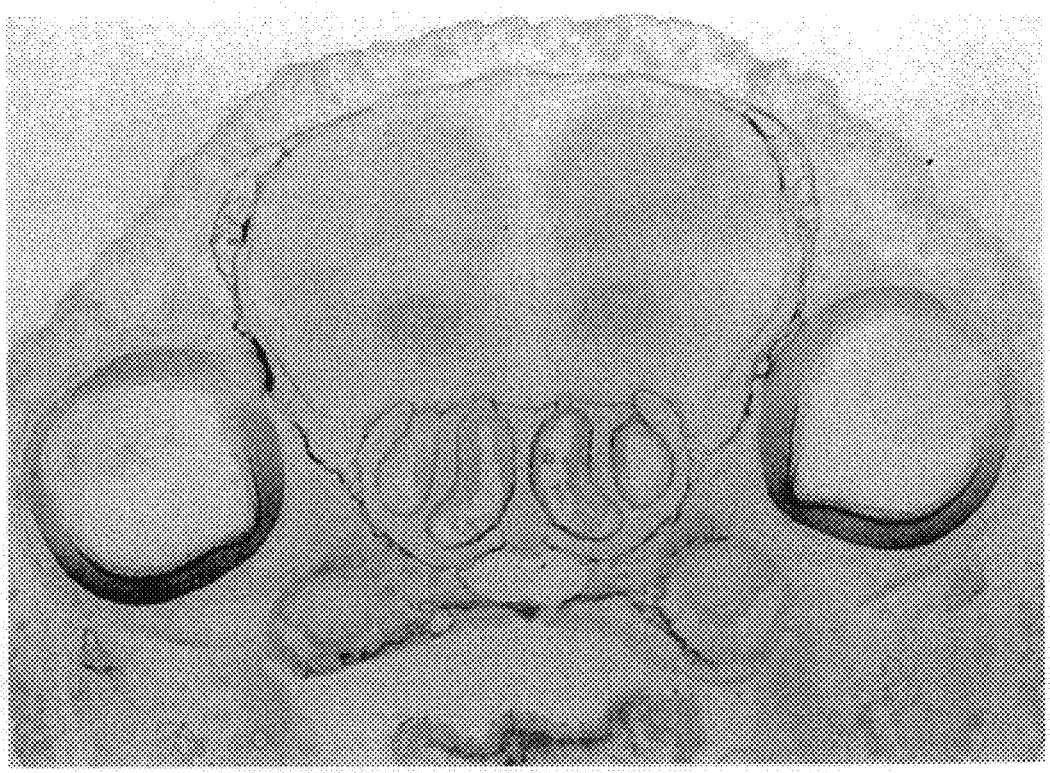
FIG. 23A shows a coronal section through the anterior brain region of an E16.5 Nuk$^2$/Nuk$^2$ mouse embryo showing staining of the ventral retinal cells.
Figure 23B:
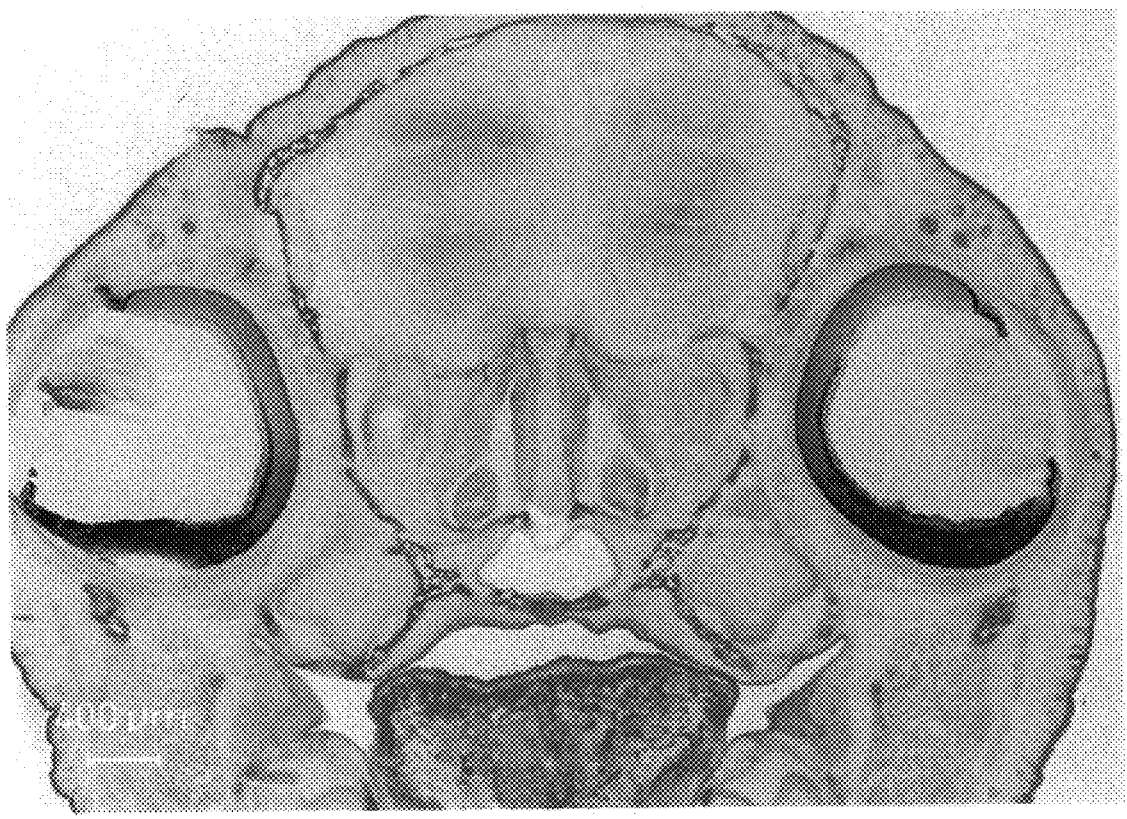
FIG. 23B shows a coronal section through the anterior brain region of an E16.5; Nu k$^2$/Nuk$^2$ mouse embryo showing staining of the ventral retinal cells
Figure 23C:
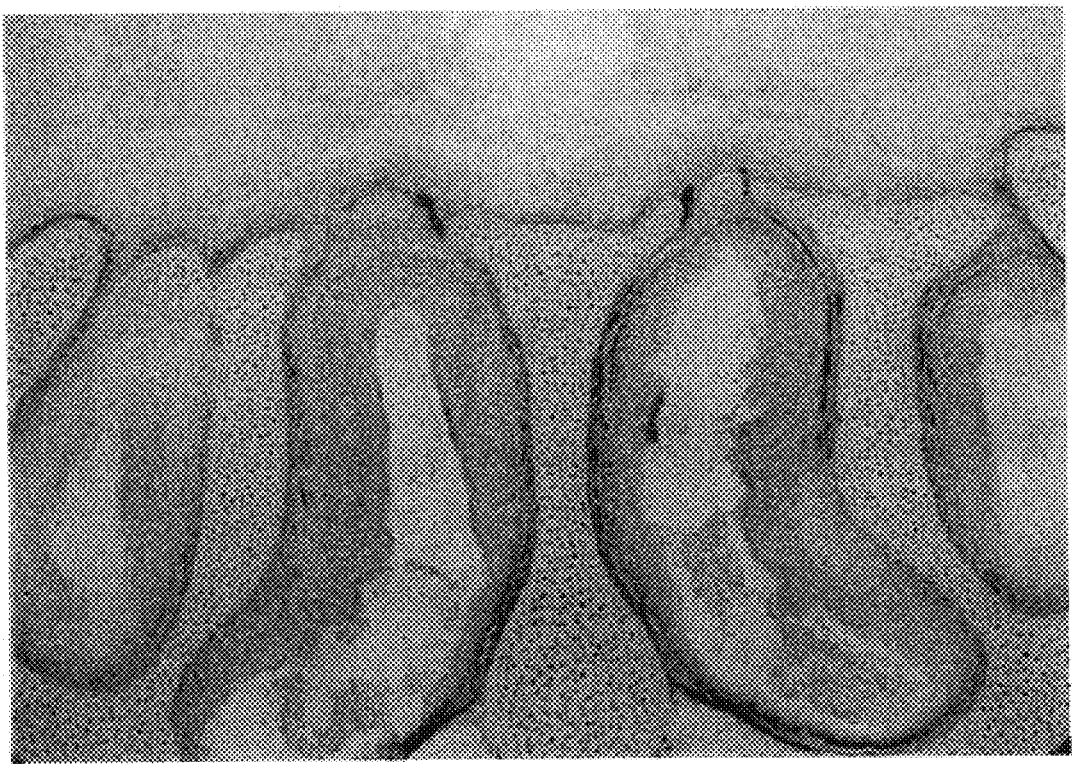
FIG. 23C shows a coronal section through the anterior brain region of an E16.5 Nuk$^2$/Nuk$^2$ mouse embryo showing staining of the axons of olfactory receptor neurons as they enter the olfactory bulbs.
Figure 23D:
FIG. 23D shows a coronal section through the anterior brain region of an E16.5 Nuk$^2$/Nuk$^2$ mouse embryo showing staining of the ventral retinal cells.

Nuk-lacZ expression at the level of the eyes and olfactory bulbs in E16.5 day embryos is shown in FIGS. 23A, 23B, 23C and 23D. FIGS. 23C and 23D are higher magnifications of areas shown in FIGS. 23A and 23B respectively. Little or no staining was detected in the olfactory bulbs, but the axons entering the olfactory bulbs were stained, as shown in FIG. 23C. Intense staining was found in the ventral cells of the retina, with decreasing staining toward the dorsal cells of the retina as shown in FIGS. 23A, 23B and 23C.

Figure 24A:
FIG. 24A shows a sagittal section through the brain of a newborn Nuk$^2$/Nuk$^2$ mouse showing staining of the hypothalamus, thalamus, midbrain, hindbrain and cerebellum.
Figure 24B:
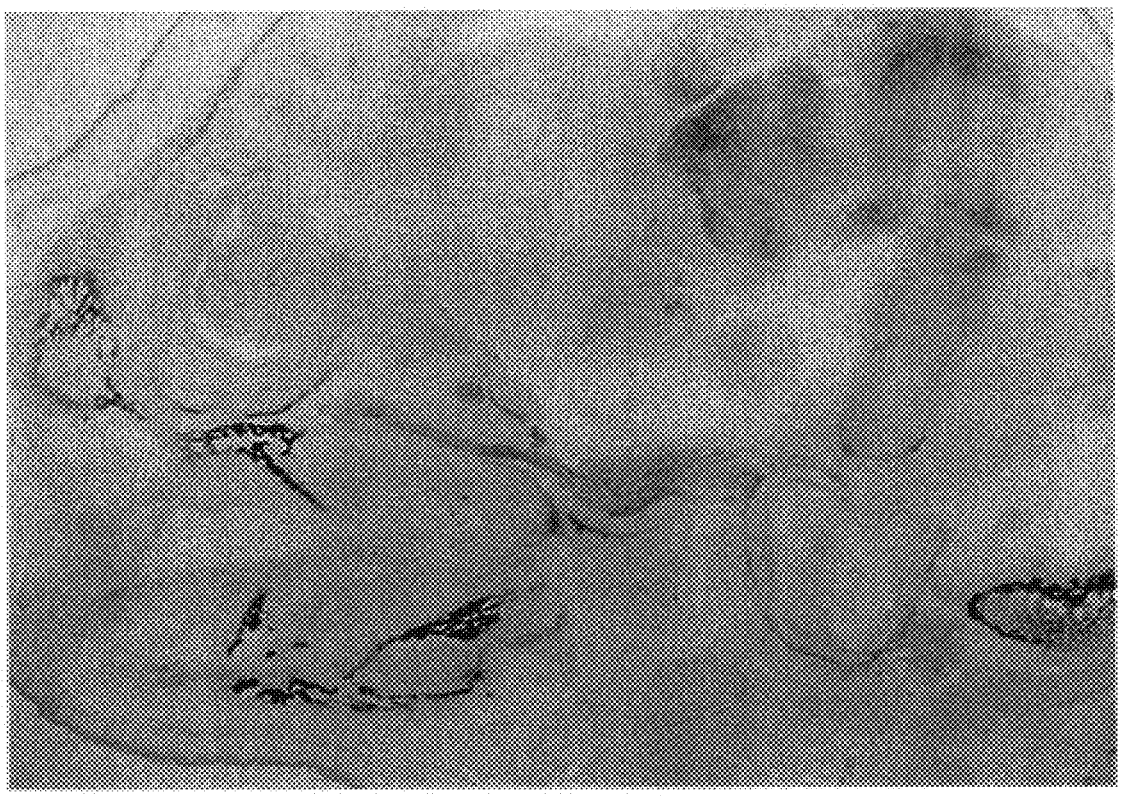
FIG. 24B shows a sagittal section through the brain of a newborn Nuk$^2$/Nuk$^2$ mouse showing staining of the optic nerve.
Figure 24C:
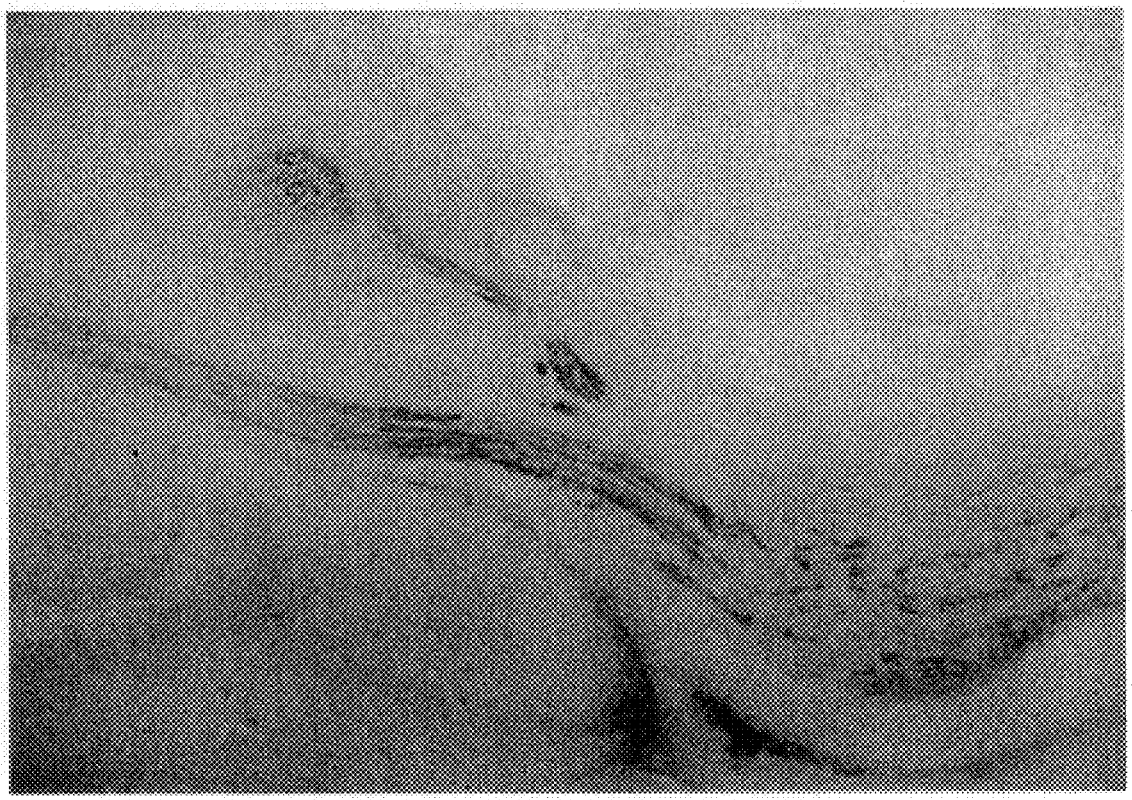
FIG. 24C shows a sagittal section through the brain of a newborn Nuk$^2$/Nuk$^2$ mouse showing staining of the optic nerve, trigeminal ganglion and trigeminal nerve roots.

Nuk-lacZ expression in sagittal sections of the brain of newborn mice is shown in FIGS. 24A, 24B and 24C. High levels of Nuk-lacZ expression were detected in the thalamus, hypothalamus, midbrain, hindbrain and cerebellum (FIG. 24A). FIG. 24C is a higher magnification view, showing staining of the optic nerve, trigeminal ganglion, and trigeminal nerve roots, at least some of which are from whisker sensory neurons.

Further information about the role of Nuk protein in axonal pathfinding was obtained from examining the brains of mice having double mutations in Nuk and in Sek4, another member of the Eph subfamily of receptor tyrosine kinases. Mice bearing a Sck4 null mutation were prepared (Klein and Orioloi, European Molecular Biology Laboratory, Heidelberg, Germany). The Sek4 null mice, similar to the Nuk null mice, exhibited no obvious morphological or behavioral defects. However, Nuk$^1$/Sek4 double homozygous mutants died at birth. Nuk$^2$/Sek$^4$ mice survived up to 3 months, confirming that Nuk protein plays a crucial role which is independent of its catalytic kinase domain.

Figure 26:
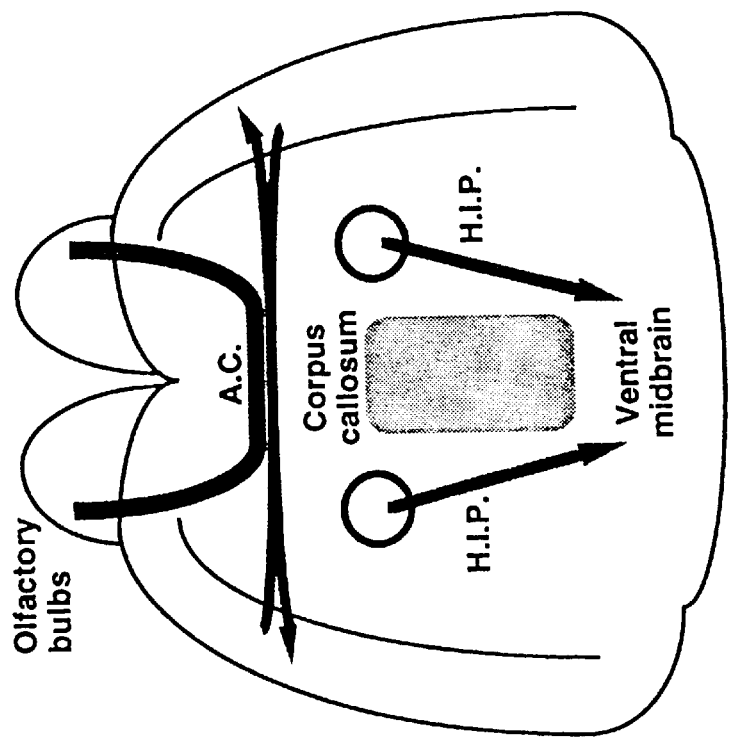
FIG. 26 is a diagram illustrating the axon pathways affected in Nuk/Sek4 double homozygotes.

An examination of coronal sections of the brains of newborn Nuk$^1$/Sek$^4$ mice showed that, in addition to the anterior commissure defect found in Nuk$^1$/– mice, the corpus callosum and habenular interpeduncle tracts were severly affected and failed to develop properly. The axon pathways affected in the Nuk/Sek double homozygotes is illustrated in FIG. 26. The fibres of the anterior commissure appeared to be misdirected and oriented to the ventral-most floor of the brain. In addition, the fibres of the corpus callosum had not joined up across the midline, but had piled up against the lateral ventricles. Nuk,-Lac Z expression, based on blue/green staining, was detected in the mid line of the corpus callosum. The habenular interpeduncle tract which connects the thalamus to the ventral midbrain, was defective in Nuk$^2$/Sek$^4$ and Nuk$^1$/Sek4. Careful analysis of Nuk protein using anti-Nuk antibodies and lac Z staining of Nuk$^2$/Nuk$^2$ embryos showed that, during development, Nuk expression appears in the ventral midbrain and progresses towards the thalamus and axon migration occurred in the opposite direction, i.e. from the thalamus toward the ventral mid brain. This axon migration was dependent on the expression of Nuk protein having a catalytic kinase domain.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

All publications, patents and patent applications referred to herein are incorporated by reference in their entirety to the same extent as if each individual publication, patent or patent application was specifically and individually indicated to be incorporated by reference in its entirety.

The following sequence listings form part of the application.

We claim:

1. A composition which comprises a purified and isolated protein consisting of the amino acid sequence as shown in SEQ ID NO: 2 from amino acid number 26 to 548 effective for inhibiting axonogenesis and a pharmaceutically acceptable carrier, diluent or excipient.